(12) United States Patent
Bashiardes et al.

(10) Patent No.: US 6,288,066 B1
(45) Date of Patent: Sep. 11, 2001

(54) POLYHYDROXYBUTYLPYRAZINES, THEIR PREPARATION AND MEDICAMENTS COMPRISING THEM

(75) Inventors: Georges Bashiardes, Poitiers; Jean-Christophe Carry, Meudon; Michel Evers, La Queue en Brie; Bruno Filoche, Creteil; Serge Mignani, Chatenay-Malabry, all of (FR)

(73) Assignee: Aventis Pharma S.A., Antiony (FR)

( * ) Notice: Subject to any disclaimer, the term of this patent is extended or adjusted under 35 U.S.C. 154(b) by 0 days.

(21) Appl. No.: 09/484,342

(22) Filed: Jan. 18, 2000

Related U.S. Application Data

(63) Continuation of application No. PCT/FR98/01543, filed on Jul. 15, 1998.

(30) Foreign Application Priority Data

Jul. 17, 1997 (FR) .................................................. 97 09059

(51) Int. Cl.⁷ .......................... A61K 31/4965; A61P 3/10; C07D 241/12
(52) U.S. Cl. ......................................... 514/252.1; 544/336
(58) Field of Search .......................... 544/336; 514/252.1

(56) References Cited

FOREIGN PATENT DOCUMENTS

WO9728813    8/1997  (WO) .

OTHER PUBLICATIONS

Chemical Abstracts, Columbus, Ohio, US., vol. 121, No. 1, 1994, Abstract No. 9331h, p. 990.

Chemical Abstracts, Columbus, Ohio, vol. 90, No. 11, 1979, Abstracts No. 1927z, p. 329.

Eitelman, Decomposition reactions of amino sugars., Carbohydrate Research, 77:205–211 (1979).

*Primary Examiner*—Mukund J. Shah
*Assistant Examiner*—Venkataraman Balasubramanian
(74) *Attorney, Agent, or Firm*—Irving Newman

(57) ABSTRACT

Disclosed are polyhydroxybutylpyrazines of the general formula

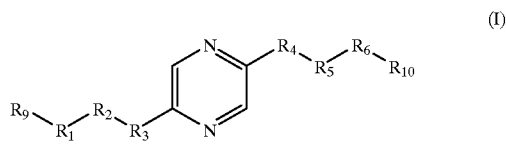

(I)

Including their isomers, racemates, enantioners and salts thereof, as well as processes for preparing these compounds and medicaments containing them.

13 Claims, No Drawings

POLYHYDROXYBUTYLPYRAZINES, THEIR PREPARATION AND MEDICAMENTS COMPRISING THEM

This application is a continuation of PCT/FR98/01543 Jul. 15, 1998.

The present invention relates to medicaments comprising, as active principle, at least one compound of formula:

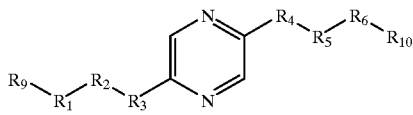

(I)

or one of its stereoisomers or one of its salts, to novel compounds of formula (I), their stereoisomers and their salts, and to their process of preparation.

In the formula (I) either (A) $R_9$ and $R_{10}$ each represent a —$CH_2OH$ radical, and either a) $R_3$ represents a methylene radical, $R_4$ represents a —CHOH— radical and one of the $R_1$, $R_2$, $R_5$ and $R_6$ radicals represents a carbonyl, methylene, —CHF—, —CH($NHR_7$)— or —CH($OR_8$) radical and the others each represent a —CHOH— radical, b) $R_2$ and $R_5$ each represent a —CHOH— radical, $R_3$ represents a methylene radical and $R_1$, $R_4$ and $R_6$ are identical and each represent a carbonyl, methylene, —CHF—, —CH($NHR_7$)— or —CH($OR_8$) radical, c) $R_1$ and $R_6$ each represent a —CHOH— radical, $R_3$ represents a methylene radical and $R_2$, $R_4$ and $R_5$ are identical and each represent a carbonyl, methylene, —CHF—, —CH($NHR_7$)— or —CH($OR_8$) radical, d) $R_1$, $R_4$, $R_5$ and $R_6$ each represent a —CHOH— radical and —$R_2$—$R_3$— represents a —CH=CH— radical, or (B) $R_1$, $R_2$, $R_4$, $R_5$ and $R_6$ each represent a —CHOH— radical, $R_3$ represents a methylene radical, $R_9$ represents a —$CH_2F$ or —$CH_2OH$ radical, $R_{10}$ represents a —$CH_2F$ or —$CH_2OH$ radical, $R_9$ and $R_{10}$ not both being a —$CH_2OH$ radical, $R_7$ represents a hydrogen atom or an alkyl, —CO—alk, —CO—Ar or —CO—Het radical, $R_8$ represents an alkyl, —alk—COOH or —alk—OH radical, alk represents an alkyl radical, Ar represents a phenyl radical or a phenyl radical substituted by one or more substituents chosen from a halogen atom or an alkyl, alkoxy, alkoxycarbonyl, amino, monoalkylamino or dialkylamino radical, Het represents a saturated or unsaturated, mono-, di- or tricyclic heterocycle comprising 1 to 9 carbon atoms and one or more heteroatoms chosen from oxygen, sulphur and nitrogen.

In the preceding and succeeding definitions, the alkyl and alkoxy radicals and portions comprise 1 to 6 carbon atoms in a straight or branched chain and the halogen atoms are chlorine, fluorine, iodine and bromine atoms.

As the compounds of formula (I) comprise several asymmetric carbons, [lacuna] exhibit stereoisomeric forms. These various stereoisomers form part of the invention. In addition, the compounds in which —$R_2$—$R_3$— represents a —CH=CH— radical can exist in the cis or trans form; these forms also form part of the invention.

Het preferably represents a heterocycle chosen from 2-, 3- or 4-pyridyl, imidazolyl, thiazolyl and oxazolyl rings.

In other words, the compounds of formula (I) correspond to the following formulae: in which R represents represents a carbonyl, methylene, —CHF—, —CH($NHR_7$)— or —CH($OR_8$) radical, $R_7$, $R_8$, $R_9$ and $R_{10}$ having the same meanings as above, their stereoisomeric forms and the cis and trans forms of the compounds comprising a CH=CH chain.

The preferred medicaments are those which comprise, as active principle, at least one compound of formula (I) chosen from the following compounds:

1-[5-(3R,4-Dihydroxy-2-oxobutyl)pyrazin-2-yl]butane-1R,2S,3R,4-tetraol,

1-[5-(3S,4-Dihydroxybutyl)pyrazin-2-yl]butane-1R,2S,3R,4-tetraol,

1-[5-(2S-Fluoro-3R,4-dihydroxybutyl)pyrazin-2-yl]butane-1R,2S,3R,4-tetraol,

1-[5-(2R-Fluoro-3R,4-dihydroxybutyl)pyrazin-2-yl]butane-1R,2S,3R,4-tetraol,

1-[5-(2S-Amino-3S,4-dihydroxybutyl)pyrazin-2-yl]butane-1R,2S,3R,4-tetraol,

1-[5-(2R-Amino-3S,4-dihydroxybutyl)pyrazin-2-yl]butane-1R,2S,3R,4-tetraol,

1-[5-(2S-(N-Methyl)amino-3S,4-dihydroxybutyl)pyrazin-2-yl]butane-1R,2S,3R,4-tetraol, 1-[5-(2R-(N-Methyl)amino-3S,4-dihydroxybutyl)pyrazin-2-yl]butane-1R,2S,3R,4-tetraol, 1-[5-(2S-(N-Ethyl)amino-3S,4-dihydroxybutyl)pyrazin-2-yl]butane-1R,2S,3R,4-tetraol, 1-[5-(2R-(N-Ethyl)amino-3S,4-dihydroxybutyl)pyrazin-2-yl]butane-1R,2S,3R,4-tetraol, 1-[5-(2S-(N-n-Butyl)amino-3S,4-dihydroxybutyl)pyrazin-2-yl]butane-1R,2S,3R,4-tetraol, 1-[5-(2R-(N-n-Butyl)amino-3S,4-dihydroxybutyl)pyrazin-2-yl]butane-1R,2S,3R,4-tetraol, 1-[5-(2S-(N-Benzyl)amino-3S,4-dihydroxybutyl)pyrazin-2-yl]butane-1R,2S,3R,4-tetraol, 1-[5-(2R-(N-Benzyl)amino-3S,4-dihydroxybutyl)pyrazin-2-yl]butane-1R,2S,3R,4-tetraol, 1-[5-(2S-(N-Acetyl)amino-3S,4-dihydroxybutyl)pyrazin-2-yl]butane-1R,2S,3R,4-tetraol, 1-[5-(2R-(N-Acetyl)amino-3S,4-dihydroxybutyl)pyrazin-2-yl]butane-1R,2S,3R,4-tetraol, 1-[5-(2S-(N-Butanoyl)amino-3S,4-dihydroxybutyl)pyrazin-2-yl]butane-1R,2S,3R,4-tetraol, 1-[5-(2R-(N-Butanoyl)amino-3S,4-dihydroxybutyl)pyrazin-2-yl]butane-1R,2S,3R,4-tetraol, 1-[5-(2S-(N-Benzoyl)amino-3S,4-dihydroxybutyl)pyrazin-2-yl]butane-1R,2S,3R,4-tetraol, 1-[5-(2R-(N-Benzoyl)amino-3S,4-dihydroxybutyl)pyrazin-2-yl]butane-1R,2S,3R,4-tetraol, 1-[5-(2S-Methoxy-3R,4-dihydroxybutyl)pyrazin- 2-yl]butane-1R,2S,3R,4-tetraol, 1-[5-(2R-Methoxy-3R,4-dihydroxybutyl)pyrazin-2-yl]butane-1R,2S,3R,4-tetraol, 1-[5-(2S-Ethoxy-3R,4-dihydroxybutyl)pyrazin-2-yl]butane-1R,2S,3R,4-tetraol, 1-[5-(2R-Ethoxy-3R,4-dihydroxybutyl)pyrazin-2-yl]butane-1R,2S,3R,4-tetraol, 1-[5-(2S-n-Butoxy-3S,4-dihydroxybutyl)pyrazin-2-yl]butane-1R,2S,3R,4-tetraol, 1-[5-(2R-n-Butoxy-3R,4-dihydroxybutyl)pyrazin-2-yl]butane-1R,2S,3R,4-tetraol, 1-[5-(2S-(2-Hydroxyethyl)oxy-3R,4-dihydroxybutyl)pyrazin-2-yl]butane-1R,2S,3R,4-tetraol, 1-[5-(2R-(2-Hydroxyethyl)oxy-3R,4-dihydroxybutyl)pyrazin-2-yl]butane-1R,2S,3R,4-tetraol, 1-[5-(2S-(3-Hydroxy-n-propyl)oxy-3R,4-dihydroxybutyl)pyrazin-2-yl]butane-1R,2S,3R,4-tetraol, 1-[5-(2R-(3-Hydroxy-n-propyl)oxy-3R,4-dihydroxybutyl)pyrazin-2-yl]butane-1R,2S,3R,4-tetraol, 1-[5-(2S-(Carboxymethyl)oxy-3R,4-dihydroxybutyl) pyrazin-2-yl]butane-1R,2S,3R,4-tetraol,
1-[5-(2R-(Carboxymethyl)oxy-3R,4-dihydroxybutyl) pyrazin-2-yl]butane-1R,2S,3R,4-tetraol,
1-[5-(2S-(3-Carboxy-n-propyl)oxy-3R,4-dihydroxybutyl) pyrazin-2-yl]butane-1R,2S,3R,4-tetraol,
1-[5-(2R-(3-Carboxy-n-propyl)oxy-3R,4-dihydroxybutyl) pyrazin-2-yl]butane-1R,2S,3R,4-tetraol,
1-[5-(2S,4-Dihydroxy-3-oxobutyl)pyrazin-2-yl]butane-1R, 2S,3R,4-tetraol,
1-[5-(2S,4-Dihydroxybutyl)pyrazin-2-yl]butane-1R,2S,3R, 4-tetraol,
1-[5-(3R-Fluoro-2S,4-dihydroxybutyl)pyrazin-2-yl]butane-1R,2S,3R,4-tetraol,
1-[5-(3S-Fluoro-2S,4-dihydroxybutyl)pyrazin-2-yl]butane-1R,2S,3R,4-tetraol,
1-[5-(3R-Amino-2R,4-dihydroxybutyl)pyrazin-2-yl]butane-1R,2S,3R,4-tetraol,
1-[5-(3S-Amino-2R,4-dihydroxybutyl)pyrazin-2-yl]butane-1R,2S,3R,4-tetraol,
1-[5-(3R-(N-Methyl)amino-2R,4-dihydroxybutyl)pyrazin-2-yl]butane-1R,2S,3R,4-tetraol,
1-[5-(3S-(N-Methyl)amino-2R,4-dihydroxybutyl)pyrazin-2-y]butane-1R,2S,3R,4-tetraol,
1-[5-(3R-(N-Ethyl)amino-2R,4-dihydroxybutyl)pyrazin-2-yl]butane-1R,2S,3R,4-tetraol,
1-[5-(3S-(N-Ethyl)amino-2R,4-dihydroxybutyl)pyrazin-2-yl]butane-1R,2S,3R,4-tetraol,
1-[5-(3R-(N-n-Butyl)amino-2R,4-dihydroxybutyl)pyrazin-2-yl]butane-1R,2S,3R,4-tetraol,
1-[5-(3S-(N-n-Butyl)amino-2R,4-dihydroxybutyl)pyrazin-2-yl]butane-1R,2S,3R,4-tetraol,
1-[5-(3R-(N-Benzyl)amino-2R,4-dihydroxybutyl)pyrazin-2-yl]butane-1R,2S,3R,4-tetraol,
1-[5-(3S-(N-Benzyl)amino-2R,4-dihydroxybutyl)pyrazin-2-yl]butane-1R,2S,3R,4-tetraol,
1-[5-(3R-(N-Acetyl)amino-2R,4-dihydroxybutyl)pyrazin-2-yl]butane-1R,2S,3R,4-tetraol,
1-[5-(3S-(N-Acetyl)amino-2R,4-dihydroxybutyl)pyrazin-2-yl]butane-1R,2S,3R,4-tetraol,
1-[5-(3R-(N-Butanoyl)amino-2R,4-dihydroxybutyl) pyrazin-2-yl]butane-1R,2S,3R,4-tetraol,
1-[5-(3S-(N-Butanoyl)amino-2R,4-dihydroxybutyl) pyrazin-2-yl]butane-1R,2S,3R,4-tetraol,
1-[5-(3R-(N-Benzoyl)amino-2R,4-dihydroxybutyl)pyrazin-2-yl]butane-1R,2S,3R,4-tetraol,
1-[5-(3S-(N-Benzoyl)amino-2R,4-dihydroxybutyl)pyrazin-2-yl]butane-1R,2S,3R,4-tetraol,
1-[5-(3R-Methoxy-2S,4-dihydroxybutyl)pyrazin-2-yl] butane-1R,2S,3R,4-tetraol,
1-[5-(3S-Methoxy-2S,4-dihydroxybutyl)pyrazin-2-yl] butane-1R,2S,3R,4-tetraol,
1-[5-(3R-Ethoxy-2S,4-dihydroxybutyl)pyrazin-2-yl]butane-1R,2S,3R,4-tetraol,
1-[5-(3S-Ethoxy-2S,4-dihydroxybutyl)pyrazin-2-yl]butane-1R,2S,3R,4-tetraol,
1-[5-(3R-n-Butoxy-2S,4-dihydroxybutyl)pyrazin-2-yl] butane-1R,2S,3R,4-tetraol,
1-[5-(3S-n-Butoxy-2S,4-dihydroxybutyl)pyrazin-2-yl] butane-1R,2S,3R,4-tetraol,
1-[5-(3R-(2-Hydroxyethyl)oxy-2S,4-dihydroxybutyl) pyrazin-2-yl]butane-1R,2S,3R,4-tetraol,
1-[5-(3S-(2-Hydroxyethyl)oxy-2S,4-dihydroxybutyl) pyrazin-2-yl]butane-1R,2S,3R,4-tetraol,
1-[5-(3R-(3-Hydroxy-n-propyl)oxy-2S,4-dihydroxybutyl) pyrazin-2-yl]butane-1R,2S,3R,4-tetraol,
1-[5-(3S-(3-Hydroxy-n-propyl)oxy-2S,4-dihydroxybutyl) pyrazin-2-yl]butane-1R,2S,3R,4-tetraol,
1-[5-(3R-(Carboxymethyl)oxy-2S,4-dihydroxybutyl) pyrazin-2-yl]butane-1R,2S,3R,4-tetraol,
1-[5-(3S-(Carboxymethyl)oxy-2S,4-dihydroxybutyl) pyrazin-2-yl]butane-1R,2S,3R,4-tetraol,
1-[5-(3R-(3-Carboxy-n-propyl)oxy-2S,4-dihydroxybutyl) pyrazin-2-yl]butane-1R,2S,3R,4-tetraol,
1-[5-(3S-(3-Carboxy-n-propyl)oxy-2S,4-dihydroxybutyl) pyrazin-2-yl]butane-1R,2S,3R,4-tetraol,
4-[5-(2S,3R,4-Trihydroxybutyl)pyrazin-2-yl]-1,3S,4R-trihydroxybutane-2-one,
1-[5-(2S,3R,4-Trihydroxybutyl)pyrazin-2-yl]butane-1R,2R, 4-triol,
1-[5-(2S,3R,4-Trihydroxybutyl)pyrazin-2-yl]-3R-fluorobutane-1R,2S,4-triol,
1-[5-(2S,3R,4-Trihydroxybutyl)pyrazin-2-yl]-3S-fluorobutane-1R,2S,4-triol,
1-[5-(2S,3R,4-Trihydroxybutyl)pyrazin-2-yl]-3R-aminobutane-1R,2R,4-triol,
1-[5-(2S,3R,4-Trihydroxybutyl)pyrazin-2-yl]-3S-aminobutane-1R,2R,4-triol,
1-[5-(2S,3R,4-Trihydroxybutyl)pyrazin-2-yl]-3R-(N-methyl)aminobutane-1R,2R,4-triol,
1-[5-(2S,3R,4-Trihydroxybutyl)pyrazin-2-yl]-3 S-(N-methyl)aminobutane-1R,2R,4-triol,
1-[5-(2S,3R,4-Trihydroxybutyl)pyrazin-2-yl]-3R-(N-ethyl) aminobutane-1R,2R,4-triol,
1-[5-(2S,3R,4-Trihydroxybutyl)pyrazin-2-yl]-3S-(N-ethyl) aminobutane-1R,2R,4-triol,
1-[5-(2S,3R,4-Trihydroxybutyl)pyrazin-2-yl]-3R-(N-n-butyl)aminobutane-1R,2R,4-triol,
1-[5-(2S,3R,4-Trihydroxybutyl)pyrazin-2-yl]-3S-(N-n-butyl)aminobutane-1R,2R,4-triol,
1-[5-(2S,3R,4-Trihydroxybutyl)pyrazin-2-yl]-3R-(N-benzyl)aminobutane-R,2R,4-triol,
1-[5-(2S,3R,4-Trihydroxybutyl)pyrazin-2-yl]-3S-(N-benzyl)aminobutane-1R,2R,4-triol,
1-[5-(2S,3R,4-Trihydroxybutyl)pyrazin-2-yl]-3R-(N-acetyl)aminobutane-1R,2R,4-triol,
1-[5-(2S,3R,4-Trihydroxybutyl)pyrazin-2-yl]-3S-(N-acetyl) aminobutane-1R,2R,4-triol,
1-[5-(2S,3R,4-Trihydroxybutyl)pyrazin-2-yl]-3R-(N-butanoyl)aminobutane-1R,2R,4-triol,
1-[5-(2S,3R,4-Trihydroxybutyl)pyrazin-2-yl]-3S-(N-butanoyl)aminobutane-1R,2R,4-triol,
1-[5-(2S,3R,4-Trihydroxybutyl)pyrazin-2-yl]-3 R-(N-benzoyl)aminobutane-1R,2R,4-triol,
1-[5-(2S,3R,4-Trihydroxybutyl)pyrazin-2-yl]-3S-(N-benzoyl)aminobutane-1R,2R,4-triol,
1-[5-(2S,3R,4-Trihydroxybutyl)pyrazin-2-yl]-3R-methoxybutane-1R,2S,4-triol,
1-[5-(2S,3R,4-Trihydroxybutyl)pyrazin-2-yl]-3S-methoxybutane-1R,2S,4-triol,
1-[5-(2S,3R,4-Trihydroxybutyl)pyrazin-2-yl]-3R-ethoxybutane-1R,2S,4-triol,
1-[5-(2S,3R,4-Trihydroxybutyl)pyrazin-2-yl]-3S-ethoxybutane-1R,2S,4-triol,
1-[5-(2S,3R,4-Trihydroxybutyl)pyrazin-2-yl]-3R-n-butoxybutane-1R,2S,4-triol,
1-[5-(2S,3R,4-Trihydroxybutyl)pyrazin-2-yl]-3S-n-butoxybutane-1R,2S,4-triol,
1-[5-(2S,3R,4-Trihydroxybutyl)pyrazin-2-yl]-3R-[(2-hydroxyethyl)oxy]butane-1R,2S,4-triol,
1-[5-(2S,3R,4-Trihydroxybutyl)pyrazin-2-yl]-3S-[(2-hydroxyethyl)oxy]butane-1R,2S,4-triol,
1-[5-(2S,3R,4-Trihydroxybutyl)pyrazin-2-yl]-3R-[(3-hydroxy-n-propyl)oxy]butane-1R,2S,4-triol,
1-[5-(2S,3R,4-Trihydroxybutyl)pyrazin-2-yl]-3S-[(3-hydroxy-n-propyl)oxy]butane-1R,2S,4-triol, 1-[5-(2S,3R,4-Trihydroxybutyl)pyrazin-2-yl]-3R-[(carboxymethyl)oxy]butane-1R,2S,4-triol,
1-[5-(2S,3R,4-Trihydroxybutyl)pyrazin-2-yl]-3S-[(carboxymethyl)oxy]butane-1R,2S,4-triol,
1-[5-(2S,3R,4-Trihydroxybutyl)pyrazin-2-yl]-3R-[(3-carboxy-n-propyl)oxy]butane-1R,2S,4-triol,
1-[5-(2S,3R,4-Trihydroxybutyl)pyrazin-2-yl]-3S-[(3-carboxy-n-propyl)oxy]butane-1R,2S,4-triol,
1-[5-(2S,3R,4-Trihydroxybutyl)pyrazin-2-yl]-1R,3R,4-trihydroxybutane-2-one,
1-[5-(2S,3R,4-Trihydroxybutyl)pyrazin-2-yl]butane-1-R,3R,4-triol,
1-[5-(2S,3R,4-Trihydroxybutyl)pyrazin-2-yl]-2R-fluorobutane-1R,3R,4-triol,
1-[5-(2S,3R,4-Trihydroxybutyl)pyrazin-2-yl]-2S-fluorobutane-1R,3R,4-triol,
1-[5-(2S,3R,4-Trihydroxybutyl)pyrazin-2-yl]-2R-aminobutane-1S,3S,4-triol,
1-[5-(2S,3R,4-Trihydroxybutyl)pyrazin-2-yl]-2S-aminobutane-1S,3S,4-triol,
1-[5-(2S,3R,4-Trihydroxybutyl)pyrazin-2-yl]-2 R-(N-methyl)aminobutane-1S,3S,4-triol,
1-[5-(2S,3R,4-Trihydroxybutyl)pyrazin-2-yl]-2S-(N-methyl)aminobutane-1S,3S,4-triol,
1-[5-(2S,3R,4-Trihydroxybutyl)pyrazin-2-yl]-2R-(N-ethyl)aminobutane-1S,3S,4-triol,
1-[5-(2S,3R,4-Trihydroxybutyl)pyrazin-2-yl]-2S-(N-ethyl)aminobutane-1S,3S,4-triol,
1-[5-(2S,3R,4-Trihydroxybutyl)pyrazin-2-yl]-2R-(N-n-butyl)aminobutane-1S,3S,4-triol,
1-[5-(2S,3R,4-Trihydroxybutyl)pyrazin-2-yl]-2S-(N-n-butyl)aminobutane-1S,3S,4-triol,
1-[5-(2S,3R,4-Trihydroxybutyl)pyrazin-2-yl]-2R-(N-benzyl)aminobutane-1S,3S,4-triol,
1-[5-(2S,3R,4-Trihydroxybutyl)pyrazin-2-yl]-2S-(N-benzyl)aminobutane-1S,3S,4-triol,
1-[5-(2S,3R,4-Trihydroxybutyl)pyrazin-2-yl]-2R-(N-acetyl)aminobutane-1S,3S,4-triol,
1-[5-(2S,3R,4-Trihydroxybutyl)pyrazin-2-yl]-2S-(N-acetyl)aminobutane-1S,3S,4-triol,
1-[5-(2S,3R,4-Trihydroxybutyl)pyrazin-2-yl]-2R-(N-butanoyl)aminobutane-1S,3S,4-triol,
1-[5-(2S,3R,4-Trihydroxybutyl)pyrazin-2-yl]-2 S-(N-butanoyl)aminobutane-1S,3S,4-triol,
1-[5-(2S,3R,4-Trihydroxybutyl)pyrazin-2-yl]-2R-(N-benzoyl)aminobutane-1S,3S,4-triol,
1-[5-(2S,3R,4-Trihydroxybutyl)pyrazin-2-yl]-2S-(N-benzoyl)aminobutane-1S,3S,4-triol,
1-[5-(2S,3R,4-Trihydroxybutyl)pyrazin-2-yl]-2R-methoxybutane-1R,3R,4-triol,
1-[5-(2S,3R,4-Trihydroxybutyl)pyrazin-2-yl]-2S-methoxybutane-1R,3R,4-triol,
1-[5-(2S,3R,4-Trihydroxybutyl)pyrazin-2-yl]-2R-ethoxybutane-1R,3R,4-triol,
1-[5-(2S,3R,4-Trihydroxybutyl)pyrazin-2-yl]-2S-ethoxybutane-1R,3R,4-triol,
1-[5-(2S,3R,4-Trihydroxybutyl)pyrazin-2-yl]-2R-n-butoxybutane-1R,3R,4-triol,
1-[5-(2S,3R,4-Trihydroxybutyl)pyrazin-2-yl]-2S-n-butoxybutane-1R,3R,4-triol,
1-[5-(2S,3R,4-Trihydroxybutyl)pyrazin-2-yl]-2R-[(2-hydroxyethyl)oxy]butane-1R,3R,4-triol,
1-[5-(2S,3R,4-Trihydroxybutyl)pyrazin-2-yl]-2S-[(2-hydroxyethyl)oxy]butane-1R,3R,4-triol,
1-[5-(2S,3R,4-Trihydroxybutyl)pyrazin-2-yl]-2R-[(3-hydroxy-n-propyl)oxy]butane-1R,3R,4-triol,
1-[5-(2S,3R,4-Trihydroxybutyl)pyrazin-2-yl]-2S-[(3-hydroxy-n-propyl)oxy]butane-1R,3R,4-triol,
1-[5-(2S,3R,4-Trihydroxybutyl)pyrazin-2-yl]-2R-[(carboxymethyl)oxy]butane-1R,3R,4-triol,
1-[5-(2S,3R,4-Trihydroxybutyl)pyrazin-2-yl]-2S-[(carboxymethyl)oxy]butane-1R,3R,4-triol,
1-[5-(2S,3R,4-Trihydroxybutyl)pyrazin-2-yl]-2R-[(3-carboxy-n-propyl)oxy]butane-1R,3R,4-triol,
1-[5-(2S,3R,4-Trihydroxybutyl)pyrazin-2-yl]-2S-[(3-carboxy-n-propyl)oxy]butane-1R,3R,4-triol,
1-[5-(2S,4-Dihydroxy-3-oxobutyl)pyrazin-2-yl]-2S,4-dihydroxybutane-1,3-dione,
4-[5-(2S,4-Dihydroxybutyl)pyrazin-2-yl]butane-1,3S-diol,
4-[5-(3R-Fluoro-2S,4-dihydroxybutyl)pyrazin-2-yl]-2R,4R-difluorobutane-1,3S-diol,
4-[5-(3S-Fluoro-2S,4-dihydroxybutyl)pyrazin-2-yl]-2S,4S-difluorobutane-1,3S-diol,
1-[5-(3R-Amino-2S,4-dihydroxybutyl)pyrazin-2-yl]-2R,4R-diaminobutane-1,3S-diol,
1-[5-(3S-Amino-2S,4-dihydroxybutyl)pyrazin-2-yl]-2S,4S-diaminobutane-1,3S-diol,
1-[5-(3R-(N-Methyl)amino-2S,4-dihydroxybutyl)pyrazin-2-yl]-2R,4R-di[(N-methyl)amino]butane-1,3S-diol,
1-[5-(3S-(N-Methyl)amino-2S,4-dihydroxybutyl)pyrazin-2-yl]-2S,4S-di[(N-methyl)amino]butane-1,3S-diol,
1-[5-(3R-(N-Ethyl)amino-2S,4-dihydroxybutyl)pyrazin-2-yl]-2R,4R-di[(N-ethyl)amino]butane-1,3S-diol,
1-[5-(3S-(N-Ethyl)amino-2S,4-dihydroxybutyl)pyrazin-2-yl]-2S,4S-di[(N-ethyl)amino]butane-1,3S-diol,
1-[5-(3R-(N-n-Butyl)amino-2S,4-dihydroxybutyl)pyrazin-2-yl]-2R,4R-di[(N-n-butyl)amino]butane-1,3S-diol,
1-[5-(3S-(N-n-Butyl)amino-2S,4-dihydroxybutyl)pyrazin-2-yl]-2S,4S-di[(N-n-butyl)amino]butane-1,3S-diol,
1-[5-(3R-(N-Benzyl)amino-2S,4-dihydroxybutyl)pyrazin-2-yl]-2R,4R-di[(N-benzyl)amino]butane-1,3S-diol,
1-[5-(3S-(N-Benzyl)amino-2S,4-dihydroxybutyl)pyrazin-2-yl]-2S,4S-di[(N-benzyl)amino]butane-1,3S-diol,
1-[5-(3R-(N-Acetyl)amino-2S,4-dihydroxybutyl)pyrazin-2-yl]-2R,4R-di[(N-acetyl)amino]butane-1,3S-diol,
1-[5-(3S-(N-Acetyl)amino-2S,4-dihydroxybutyl)pyrazin-2-yl]-2S,4S-di[(N-acetyl)amino]butane-1,3S-diol,
1-[5-(3R-(N-Butanoyl)amino-2S,4-dihydroxybutyl)pyrazin-2-yl]-2R,4R-di[(N-butanoyl)amino]butane-1,3S-diol,
1-[5-(3S-(N-Butanoyl)amino-2S,4-dihydroxybutyl)pyrazin-2-yl]-2S,4S-di[(N-butanoyl)amino]butane-1,3S-diol,
1-[5-(3R-(N-Benzoyl)amino-2S,4-dihydroxybutyl)pyrazin-2-yl]-2R,4R-di[(N-benzoyl)amino]butane-1,3S-diol,
1-[5-(3S-(N-Benzoyl)amino-2S,4-dihydroxybutyl)pyrazin-2-yl]-2S,4S-di[(N-benzoyl)amino]butane-1,3S-diol,
1-[5-(3R-Methoxy-2S,4-dihydroxybutyl)pyrazin-2-yl]-2R,4R-dimethoxybutane-1,3S-diol,
1-[5-(3S-Methoxy-2S,4-dihydroxybutyl)pyrazin-2-yl]-2S,4S-dimethoxybutane-1,3S-diol,
1-[5-(3R-Ethoxy-2S,4-dihydroxybutyl)pyrazin-2-yl]-2R,4R-diethoxybutane-1,3S-diol,
1-[5-(3S-Ethoxy-2S,4-dihydroxybutyl)pyrazin-2-yl]-2S,4S-diethoxybutane-1,3S-diol,
1-[5-(3R-n-Butoxy-2S,4-dihydroxybutyl)pyrazin-2-yl]-2R,4R-di-n-butoxybutane-1,3S-diol,
1-[5-(3S-n-Butoxy-2S,4-dihydroxybutyl)pyrazin-2-yl]-2S,4S-di-n-butoxybutane-1,3S-diol,
1-[5-(3R-(2-Hydroxyethyl)oxy-2S,4-dihydroxybutyl)pyrazin-2-yl]-2R,4R-di[(2-hydroxyethyl)oxy]butane-1,3S-diol,
1-[5-(3S-(2-Hydroxyethyl)oxy-2S,4-dihydroxybutyl)pyrazin-2-yl]-2S,4S-di[(2-hydroxyethyl)oxy]butane-1,3S-diol,
1-[5-(3R-(3-Hydroxy-n-propyl)oxy-2S,4-dihydroxybutyl)pyrazin-2-yl]-2R,4R-di[(3-hydroxy-n-propyl)oxy]butane-1,3S-diol, 1-[5-(3S-(3-Hydroxy-n-propyl)oxy-2S,4-dihydroxybutyl)
pyrazin-2-yl]-2S,4S-di[(3-hydroxy-n-propyl)oxy]butane-
1,3S-diol,
1-[5-(3R-(Carboxymethyl)oxy-2S,4-dihydroxybutyl)
pyrazin-2-yl]-2R,4R-di[(carboxymethyl)oxy]butane-1,
3S-diol,
1-[5-(3S-(Carboxymethyl)oxy-2S,4-dihydroxybutyl)
pyrazin-2-yl]-2S,4S-di[(carboxymethyl)oxy]butane-1,
3S-diol,
1-[5-(3R-(3-Carboxy-n-propyl)oxy-2S,4-dihydroxybutyl)
pyrazin-2-yl]-2R,4R-di [(3-carboxy-n-propyl)oxy]
butane-1,3S-diol,
1-[5-(3S-(3-Carboxy-n-propyl)oxy-2S,4-dihydroxybutyl)
pyrazin-2-yl]-2S,4S-di[(3-carboxy-n-propyl)oxy]butane-
1,3S-diol,
1-[5-(3R,4-Dihydroxy-2-oxobutyl)pyrazin-2-yl]-3R,4
-dihydroxybutane-1,2-dione,
4-[5-(2S,4-Dihydroxybutyl)pyrazin-2-yl]butane-1,3S-diol,
4-[5-(3R-Fluoro-2S,4-dihydroxybutyl)pyrazin-2-yl]-2R,4R-
difluorobutane-1,3S-diol,
4-[5-(3S-Fluoro-2S,4-dihydroxybutyl)pyrazin-2-yl]-2S,4S-
difluorobutane-1,3S-diol,
4-[5-(3R-Amino-2S,4-dihydroxybutyl)pyrazin-2-yl]-2R,
4R-diaminobutane-1,3S-diol,
4-[5-(3S-Amino-2S,4-dihydroxybutyl)pyrazin-2-yl]-2S,4S-
diaminobutane-1,3S-diol,
4-[5-(3R-(N-Methyl)amino-2S,4-dihydroxybutyl)pyrazin-
2-yl]-2R,4R-di[(N-methyl)amino]butane-1,3S-diol,
4-[5-(3S-(N-Methyl)amino-2S,4-dihydroxybutyl)pyrazin-2-
yl]-2S,4S-di[(N-methyl)amino]butane-1,3S-diol,
4-[5-(3R-(N-Ethyl)amino-2S,4-dihydroxybutyl)pyrazin-2-
yl]-2R,4R-di[(N-ethyl)amino]butane-1,3S-diol,
4-[5-(3S-(N-Ethyl)amino-2S,4-dihydroxybutyl)pyrazin-2-
yl]-2S,4S-di[(N-ethyl)amino]butane-1,3S-diol,
4-[5-(3R-(N-n-Butyl)amino-2S,4-dihydroxybutyl)pyrazin-
2-yl]-2R,4R-di[(N-n-butyl)amino]butane-1,3S-diol,
4-[5-(3S-(N-n-Butyl)amino-2S,4-dihydroxybutyl)pyrazin-
2-yl]-2S,4S-di[(N-n-butyl)amino]butane-1,3S-diol,
4-[5-(3R-(N-Benzyl)amino-2S,4-dihydroxybutyl)pyrazin-
2-yl]-2R,4R-di[(N-benzyl)amino]butane-1,3S-diol,
4-[5-(3S-(N-Benzyl)amino-2S,4-dihydroxybutyl)pyrazin-2-
yl]-2S,4S-di[(N-benzyl)amino]butane-1,3S-diol,
4-[5-(3R-(N-Acetyl)amino-2S,4-dihydroxybutyl)pyrazin-2-
yl]-2R,4R-di[(N-acetyl)amino]butane-1,3S-diol,
4-[5-(3S-(N-Acetyl)amino-2S,4-dihydroxybutyl)pyrazin-2-
yl]-2S,4S-di[(N-acetyl)amino]butane-1,3S-diol,
4-[5-(3R-(N-Butanoyl)amino-2S,4-dihydroxybutyl)
pyrazin-2-yl]-2R,4R-di[(N-butanoyl)amino]butane-1,3S-
diol,
4-[5-(3S-(N-Butanoyl)amino-2S,4-dihydroxybutyl)pyrazin-
2-yl]-2S,4S-di[(N-butanoyl)amino]butane-1,3S-diol,
4-[5-(3R-(N-Benzoyl)amino-2S,4-dihydroxybutyl)pyrazin-
2-yl]-2R,4R-di[(N-benzoyl)amino]butane-1,3S-diol,
4-[5-(3S-(N-Benzoyl)amino-2S,4-dihydroxybutyl)pyrazin-
2-yl]-2S,4S-di[(N-benzoyl)amino]butane-1,3S-diol,
4-[5-(3R-Methoxy-2S,4-dihydroxybutyl)pyrazin-2-yl]-2R,
4R-dimethoxybutane-1,3S-diol,
4-[5-(3S-Methoxy-2S,4-dihydroxybutyl)pyrazin-2-yl]-2S,
4S-dimethoxybutane-1,3S-diol,
4-[5-(3R-Ethoxy-2S,4-dihydroxybutyl)pyrazin-2-yl]-2R,
4R-diethoxybutane-1,3S-diol,
4-[5-(3S-Ethoxy-2S,4-dihydroxybutyl)pyrazin-2-yl]-2S,4S-
diethoxybutane-1,3S-diol,
4-[5-(3R-n-Butoxy-2S,4-dihydroxybutyl)pyrazin-2-yl]-2R,
4R-di-n-butoxybutane-1,3S-diol,
4-[5-(3S-n-Butoxy-2S,4-dihydroxybutyl)pyrazin-2-yl]-2S,
4S-di-n-butoxybutane-1,3S-diol,
4-[5-(3R-(2-Hydroxyethyl)oxy-2S,4-dihydroxybutyl)
pyrazin-2-yl]-2R,4R-di[(2-hydroxyethyl)oxy]butane-1,
3S-diol,
4-[5-(3S-(2-Hydroxyethyl)oxy-2S,4-dihydroxybutyl)
pyrazin-2-yl]-2S,4S-di[(2-hydroxyethyl)oxy]butane-1,
3S-diol,
4-[5-(3R-(3-Hydroxy-n-propyl)oxy-2S,4-dihydroxybutyl)
pyrazin-2-yl]-2R,4R-di[(3-hydroxy-n-propyl)oxy]
butane-1,3S-diol,
4-[5-(3S-(3-Hydroxy-n-propyl)oxy-2S,4-dihydroxybutyl)
pyrazin-2-yl]-2S,4S-di[(3-hydroxy-n-propyl)oxy]butane-
1,3S-diol,
4-[5-(3R-(Carboxymethyl)oxy-2S,4-dihydroxybutyl)
pyrazin-2-yl]-2R,4R-di[(carboxymethyl)oxy]butane-1,
3S-diol,
4-[5-(3S-(Carboxymethyl)oxy-2S,4-dihydroxybutyl)
pyrazin-2-yl]-2S,4S-di[(carboxymethyl)oxy]butane-1,
3S-diol,
4-[5-(3R-(3-Carboxy-n-propyl)oxy-2S,4-dihydroxybutyl)
pyrazin-2-yl]-2R,4R-di[(3-carboxy-n-propyl)oxy]butane-
1,3S-diol,
4-[5-(3S-(3-Carboxy-n-propyl)oxy-2S,4-dihydroxybutyl)
pyrazin-2-yl]-2S,4S-di[(3-carboxy-n-propyl)oxy]butane-
1,3S-diol,
1-[5-(3S,4-Dihydroxy-1E-butenyl)pyrazin-2-yl]butane-1R,
2S,3R,4-tetraol,
4-Fluoro-1-[5-(2S,3R,4-trihydroxybutyl)pyrazin-2-yl]
butane-1R,2S,3S-triol,
1-[5-(4-Fluoro-2S,3S-dihydroxybutyl)pyrazin-2-yl]butane-
1R,2S,3R,4-tetraol
and their salts with a pharmaceutically acceptable inorganic
or organic acid.

The particularly preferred medicaments are those which
comprise, as active principle, at least one compound of
formula (I) in which:
either (A) $R_9$ and $R_{10}$ each represent a —CH$_2$OH radical and
either
  a) $R_3$ represents a methylene radical, $R_4$ represents a
     —CHOH— radical and one of the $R_1$, $R_2$, $R_5$ and $R_6$
     radicals represents a —CHF or —CH(OR$_8$) radical and
     the others each represent a —CHOH— radical,
  b) $R_2$ and $R_5$ each represent a —CHOH— radical, $R_3$
     represents a methylene radical and $R_1$, $R_4$ and $R_6$ are
     identical and each represent a —CH(OR$_8$) radical,
  c) $R_1$ and $R_6$ each represent a —CHOH— radical, $R_3$
     represents a methylene radical and $R_2$, $R_4$ and $R_5$ are
     identical and each represent a —CH(OR$_8$) radical,
  d) $R_1$, $R_4$, $R_5$ and $R_6$ each represent a —CHOH— radical
     and —R$_2$—R$_3$— represents a —CH=CH— radical,
or (B) $R_1$, $R_2$, $R_4$, $R_5$ and $R_6$ each represent a —CHOH—
radical, $R_3$ represents a methylene radical, $R_9$ represents a
—CH$_2$OH radical, $R_{10}$ represents a —CH$_2$F radical,
$R_8$ represents an alkyl radical,
their stereoisomers, the cis and trans forms of the compounds in which —R$_2$—R$_3$— represents a —CH=CH—
chain and their salts with a pharmaceutically acceptable
inorganic or organic acid.

The even more preferred medicaments are those which
comprise, as active principle, at least one compound of
formula (I) chosen from the following compounds:
1-[5-(3S,4-Dihydroxybutyl)pyrazin-2-yl]butane-1R,2S,3R,
4-tetraol,
1-[5-(3S,4-Dihydroxy-1E-butenyl)pyrazin-2-yl]butane-1R,
2S,3R,4-tetraol,
1-[5-(2S-Methoxy-3R,4-dihydroxybutyl)pyrazin-2-yl]
butane-1R,2S,3R,4-tetraol,
1-[5-(2R-Fluoro-3R,4-dihydroxybutyl)pyrazin-2-yl]butane-
1R,2S,3R,4-tetraol, 1-[5-(2S,4-Dihydroxy-3R-methoxybutyl)pyrazin-2-yl]butane-1R,2S,3R,4-tetraol, 4-[5-(3R,4-Dihydroxy-2S-methoxybutyl)]pyrazin-2-yl]-3R,4R-dimethoxybutane-1,2-diol 4-Fluoro-1-[5-(2S,3R,4-trihydroxybutyl)pyrazin-2-yl]butane-1R,2S,3R-triol and their salts with a pharmaceutically acceptable inorganic or organic acid.

The compound of formula:

(A)

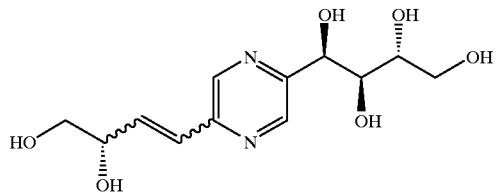

is known (Carbohydr. Res., 77, 205 (1979)) but no pharmacological property is described for this.

The other compounds of formula (I), their stereoisomers and their salts are novel and form part of the invention as such.

The preferred compounds of formula (I) are the compounds mentioned in the lists of the preferred medicaments, with the exception of the compound of formula (A).

The compounds of formula (I) in which $R_9$ and $R_{10}$ each represent a —$CH_2OH$ radical and either $R_3$ represents a methylene radical, $R_4$ represents a —CHOH— radical and one of the $R_1$, $R_2$, $R_5$ and $R_6$ radicals represents a carbonyl radical and the others each represent a —CHOH— radical, or $R_1$ and $R_6$ each represent a —CHOH— radical, $R_3$ represents a methylene radical and $R_2$, $R_4$ and $R_5$ are identical and each represent a carbonyl radical, or $R_2$ and $R_5$ each represent a —CHOH— radical, $R_3$ represents a methylene radical and $R_1$, $R_4$ and $R_6$ are identical and each represent a carbonyl radical can be prepared by oxidation of a derivative chosen from the formulae:

(II)

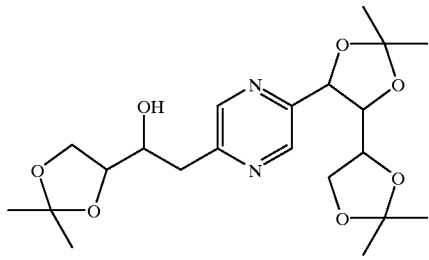

(III)

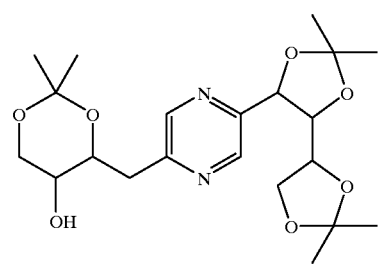

(IV)

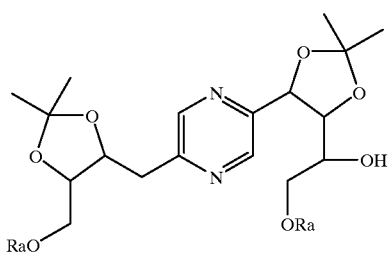

(V)

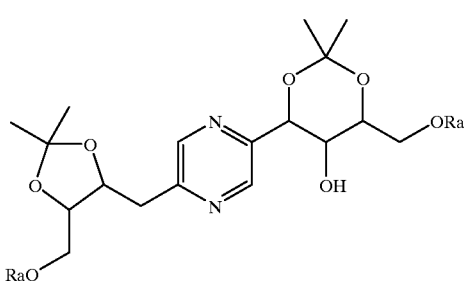

(VI)

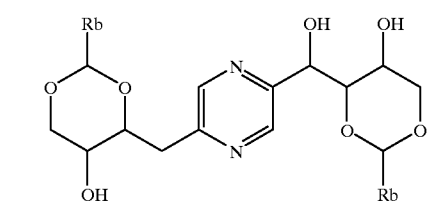

(VII)

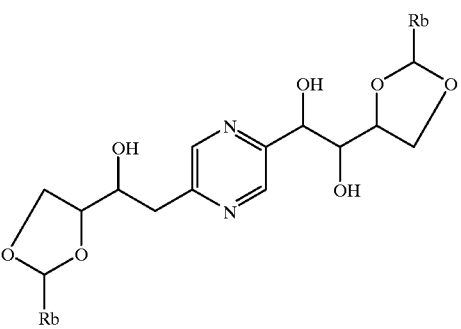

(VIII)

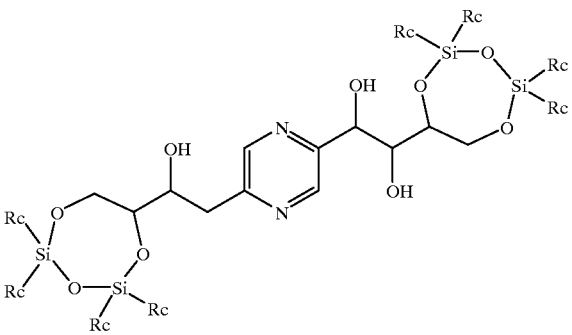

-continued (IX)

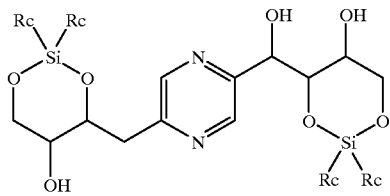

in which Ra represents a trialkylsilyl, alkyldiphenylsilyl or dialkylphenylsilyl radical, Rb represents a phenyl radical optionally substituted by at least one alkoxy radical and Rc represents an alkyl or phenyl radical, or a stereoisomer of such a derivative, followed by deprotection of the hydroxyls.

The preferred trialkylsilyl, alkyldiphenylsilyl or dialkylphenylsilyl radicals are the trimethylsilyl, tert-butyldiphenylsilyl and dimethylphenylsilyl radicals.

The oxidation reaction is carried out by any method known for the oxidation of alcohol functional groups and in particular those described by D. Swern et al., Synthesis, 165 (1981) and T. T. Tidwell, Synthesis, 857 (1990). This oxidation is preferably carried out in dimethyl sulphoxide, in the presence of oxalyl chloride and triethylamine, at a temperature of between −78✠ C. and 0✠ C.

The deprotection of the hydroxyls is carried out by any known deprotection method and in particular those described by T. W. Greene, Protective Groups in Organic Synthesis, J. Wiley-Interscience Publication (1991) or by S. V. Ley et al., Tetrahedron, 46, 4995 (1990). Use is preferably made of trifluoroacetic acid, at a temperature of between 0✠ C. and 100✠ C., or of tetra(n-butyl)ammonium fluoride, in tetrahydrofuran, at a temperature in the region of 25✠ C.

The derivatives of formulae (II) and (III) can be obtained by reaction of 2,2-dimethoxypropane with 2-(1,2,3,4-tetrahydroxybutyl)-5-(2,3,4-trihydroxybutyl)pyrazine or one of its stereoisomers and separation of the (II) and (III) derivatives.

This reaction is generally carried out according to the reaction conditions described by T. W. Greene, Protective Groups in Organic Synthesis, J. Wiley-Interscience Publication (1991). The reaction is preferably carried out in the presence of an acid, such as para-toluenesulphonic acid, in an inert solvent, such as dimethylformamide, at a temperature of between 0✠ C.and 100✠ C.

The derivatives of formula (IV) and (V) can be obtained by reaction of 2,2-dimethoxypropane with 2-(1,2,3,4-tetrahydroxybutyl)-5-(2,3,4-trihydroxybutyl)pyrazine, the chain-end hydroxyls of which were blocked beforehand by means of trialkylsilyl chloride or alkyldiphenylsilyl chloride or dialkylphenylsilyl chloride, or a stereoisomer of such a derivative, and then separation of the (IV) and (V) derivatives.

This reaction is generally carried out according to the reaction conditions described by T. W. Greene, Protective Groups in Organic Synthesis, J. Wiley-Interscience Publication (1991). The reaction is preferably carried out in the presence of an acid, such as para-toluenesulphonic acid, in an inert solvent, such as dimethylformamide, at a temperature of between 0✠ C. and 100✠ C.

The protection of the chain-end hydroxyls is generally carried out according to the reaction conditions described by T. W. Greene, Protective Groups in Organic Synthesis, J. Wiley-Interscience Publication (1991). The reaction is preferably carried out in pyridine, at a temperature of between 0✠ C. and 30✠ C.

The derivatives of formula (VI) and (VII) can be obtained by reaction of a benzaldehyde, the phenyl of which is optionally substituted by at least one alkoxy radical, or a dialkyl acetal derivative of the benzaldehyde, the phenyl of which is optionally substituted by at least one alkoxy radical (benzaldehyde dimethyl acetal, for example), with 2-(1,2,3,4-tetrahydroxybutyl)-5-(2,3,4-trihydroxybutyl)pyrazine or one of its stereoisomers.

This reaction is generally carried out according to the reaction conditions described by R. S. Coleman et al., J. Org. Chem., 57, 3732 (1992). The reaction is preferably carried out in the presence of an acid, such as D-camphorsulphonic acid, in an inert solvent, such as dimethylformamide, at a temperature of between 0✠ C. and 100✠ C.

The derivatives of formula (VIII) and (IX) can respectively be obtained by reaction of 1,3-dichloro-1,1,3,3-tetraalkyldisiloxane or 1,3-dichloro-1,1,3,3-tetraphenyldisiloxane, on the one hand, or of dialkylsilyl bischloride or dialkylsilyl bis(trifluoromethanesulphonate) or diphenylsilyl bischloride or diphenylsilyl bis(trifluoromethanesulphonate), on the other hand, with 2-(1,2,3,4-tetrahydroxybutyl)-5-(2,3,4-trihydroxybutyl)pyrazine or one of its stereoisomers, generally according to the reaction conditions described by T. W. Greene, Protective Groups in Organic Synthesis, J. Wiley—Interscience Publication (1991). The reaction is preferably carried out in pyridine, in the presence respectively of 1,3-dichloro-1,1,3,3-tetraisopropyldisiloxane or diisopropylsilyl bis(trifluoromethanesulphonate), at a temperature of between 0✠ C. and 30✠ C.

2-(1,2,3,4-Tetrahydroxybutyl)-5-(2,3,4-trihydroxybutyl)pyrazine and its stereoisomers can be obtained either from one or two aminoaldoses $OHC—CH(NH_2)—(CHOH)_3—CH_2OH$ or one of its stereoisomers, in acidic medium and more particularly in acetic acid medium, the reaction preferably being carried out at a temperature of between 150✠ C. and 100✠ C. or from one or two ketoses $HOCH_2—CO—(CHOH)_3—CH_2OH$ or one of its stereoisomers, by reaction with ammonium formate, the reaction preferably being carried out at a temperature of between 15✠ C. and 100✠ C. and preferably in aqueous medium.

The aminoaldose $OHC—CH(NH_2)—(CHOH)_3—CH_2OH$ and its stereoisomers are commercially available or can be prepared by application or adaptation of the methods described in, for example:

(a) Methods Carbohydr. Chem., 7, 29 (1976), which consist in converting the aldehyde functional group of the corresponding aldose to a nitroethylene group using nitromethane in basic medium (for example, sodium ethoxide), in then successively treating the product obtained with a saturated aqueous ammonia solution, at a temperature of between 20✠ C. and 30✠ C., with $Ba(OH)_2$ in aqueous solution, at a temperature of between 20✠ C. and 30✠ C., and finally [lacuna] dilute sulphuric acid (10 to 15%), at a temperature of between 20✠ C. and 20✠ C., (b) "The Amino Sugar", edited by R. W. Jeanloz, Academic Press, New York, 1969, page 1 or "The Carbohydrates", edited by W. Pigman and D. Horton, Academic Press, New York, Volume IB, 1980, page 664, which consist in converting the aldehyde functional group of the corresponding aldose to an imino group from a primary aromatic amine (for example aniline) and subsequently in successively reacting [lacuna] hydrocyanic acid, at a temperature of between 0° C. and 20° C., and [lacuna] hydrogen in the presence of palladium in a solvent, such as an ether (for example tetrahydrofuran) or an aliphatic alcohol (for example, ethanol or methanol), at a temperature of between 20° C. and 50° C.

The ketose $HOCH_2$—CO—$(CHOH)_3$—$CH_2OH$ and its stereoisomers are commercially available or can be prepared by application or adaptation of the methods described in, for example:

a) Adv. Carbohydr. Chem., 13, 63 (1958), which consist in reacting the corresponding aldose either with a base, such as calcium hydroxide, sodium hydroxide, pyridine or quinoline, or with an acid, such as sulphuric acid, in aqueous solution or in the pure phase, at a temperature of between 20 and 50° C., b) Tetrahedron Asymmetry, 7(8), 2185, (1996), J. Am. Chem. Soc., 118(33), 7653 (1996), J. Org. Chem., 60(13), 4294 (1995), Tetrahedron Lett., 33(36), 5157 (1992), J. Am. Chem. Soc., 113(17), 6678 (1991), Angew. Chem., 100(5), 737, (1988), J. Org. Chem., 57, 5899 (1992), which consist, for example, in condensing either hydroxypyruvaldehyde, 1,3-dihydroxyacetone, 1,3-dihydroxyacetone monophosphate or hydroxypyruvic acid with a 2-hydroxyacetaldehyde which is substituted in the 2 position and which is optionally optically pure, optionally in the presence of an enzyme, such as a transketolase. This reaction is generally carried out in aqueous solution, at a temperature of between 20 and 50° C., optionally in the presence of a base (sodium hydroxide, for example), barium chloride, magnesium chloride or zinc chloride. The derivatives possessing a 2-hydroxyacetaldehyde group are commercially available or can be prepared from aldoses by application or adaptation of the methods described in P. Collins and R. Ferrier, Monosaccharides, Their Chemistry and Their Roles in Natural Products, published by J. Wiley (1995), and M. Bols, Carbohydrate Building Blocks, published by J. Wiley (1996).

The corresponding aldoses and their stereoisomers are commercially available or can be obtained from:

a) commercially available aldoses:

by epimerization reactions, by application or adaptation of the methods described in Adv. Carbohydr. Chem., 13, 63, (1958), in particular in basic medium, by means of a dilute aqueous sodium hydroxide solution (0.03 to 0.05%), at a temperature of between 20 and 40° C.

by chain-extension reactions, by application or adaptation of the methods described in "The Carbohydrates", edited by W. Pigman and D. Horton, Academic Press, New York, Volume IA, 133 (1972), and in particular by forming the cyanohydrin of the starting aldose (for example, by reaction with sodium cyanide in aqueous solution, at a temperature of between 10 and 30° C. and in the presence of sodium hydroxide, at a pH in the region of 9), then hydrolysis of the nitrile functional group thus formed to the corresponding acid by application or adaptation of the methods described in Organic Synthesis, Volume I, page 436 and Volume III, page 85 (for example, using concentrated sulphuric acid or hydrochloric acid, in aqueous solution, at a temperature of between 20° C. and the boiling temperature of the reaction mixture), and then reduction of the carboxylic acid functional group to the corresponding aldehyde by application or adaptation of the methods described in J. Am. Chem. Soc., 71, 122 (1949), in particular using an alkali metal borohydride (for example, sodium borohydride), in aqueous solution, at a temperature of between 20° C. and the boiling temperature of the reaction mixture, by chain-shortening reactions, by application or adaptation of the methods described in "The Carbohydrates", edited by W. Pigman and D. Horton, Academic Press, New York, Volume IB, 1980, page 929 or Chem. Ber., 83, 559 (1950) and in particular by converting the aldehyde functional group of the aldose to the corresponding hydroxylamine by application or adaptation of the methods described in organic Synthesis, Volume II, page 314 (for example, using hydroxylamine hydrochloride, in aqueous solution and in the presence of a base, such as sodium carbonate, at a temperature of between 20 and 50° C.) and then reaction with 3,4-dinitrofluorobenzene in the presence of carbon dioxide and a base, such as sodium hydrogencarbonate, in aqueous solution, and an aliphatic alcohol (for example, isopropyl alcohol), at a temperature of between 50 and 80° C., b) corresponding allyl alcohols, by application or adaptation of the methods described in Science, 220, 949 (1983) and in particular using tert-butyl hydroperoxide in the presence of a titanium(IV) complex, such as the titanium(IV) isopropoxide and optically pure dialkyl tartrate (for example, diethyl tartrate) complex, followed by successive reaction with sodium thiophenolate, para-chloroperbenzoic acid in acetic anhydride, and diisopropylaluminium hydride.

The compounds of formula (I) in which $R_9$ and $R_{10}$ each represent a —$CH_2OH$ radical and either $R_3$ represents a methylene radical, $R_4$ represents a —CHOH— radical and one of the $R_1$, $R_2$, $R_5$ and $R_6$ radicals represents a methylene radical and the others each represent a —CHOH— radical or $R_1$ and $R_6$ each represent a —CHOH— radical, $R_3$ represents a methylene radical and $R_2$, $R_4$ and $R_5$ are identical and each represent a methylene radical or $R_2$ and $R_5$ each represent a —CHOH— radical and $R_1$, $R_3$, $R_4$ and $R_6$ each represent a methylene radical can be prepared by condensation of an alkyl or phenyl chlorothionocarbonate with a derivative of formula (II), (III), (IV), (V), (VI), (VII), (VIII) or (IX) in which Ra represents a trialkylsilyl, alkyldiphenylsilyl or dialkylphenylsilyl radical, Rb represents a phenyl radical optionally substituted by at least one alkoxy radical and Rc represents an alkyl or phenyl radical, or a stereoisomer of such a derivative, then reduction of the product obtained and deprotection of the hydroxyls.

The condensation and the reduction are generally carried out according to the reaction conditions described by D. H. R. Barton, J. Chem. Soc., Perkin I, 1574 (1975) and H. Paulsen et al., Liebigs Ann. Chem., 735 (1992). Preferably, for the condensation, the reaction is carried out in an inert solvent, such as a chlorinated solvent (for example dichloromethane) or an ether (for example, diethyl ether, tetrahydrofuran or dioxane), in the presence of an acid acceptor, such as an organic base, such as pyridine or 4-dimethylaminopyridine, at a temperature in the region of 20° C., and, for the reduction, the reaction is carried out by means of tributyltin hydride and azobis(2-methylpropionitrile) in an inert solvent, such as an aromatic solvent (for example, benzene or toluene), at a temperature of between 80° C. and 110° C. The deprotection is carried out as mentioned above.

The compounds of formula (I) in which (A) $R_9$ and $R_{10}$ each represent a —$CH_2OH$ radical and either $R_3$ represents a methylene radical, $R_4$ represents a —CHOH— radical and one of the $R_1$, $R_2$, $R_5$ and $R_6$ radicals represents a —CHF— radical and the others each represent a —CHOH— radical, or $R_1$ and $R_6$ each represent a —CHOH— radical, $R_3$ represents a methylene radical and $R_2$, $R_4$ and $R_5$ are identical and each represent a —CHF— radical, or $R_2$ and $R_5$ each represent a —CHOH— radical, $R_3$ represents a methylene radical and $R_1$, $R_4$ and $R_6$ are identical and each represent a —CHF— radical or (B) $R_1$, $R_2$, $R_4$, $R_5$ and $R_6$ each represent a —CHOH— radical, $R_3$ represent s a methylene radical, $R_9$ represents a —CH$_2$F or —CH$_2$OH radical, $R_{10}$ represents a —CH$_2$F or —CH$_2$OH radical, $R_9$ and $R_{10}$ not both being a —CH$_2$OH radical, can be prepared by fluorination of a derivative of formula (II), (III), (IV), (V), (VI), (VII), (VIII) or (IX) in which Ra represents a trialkylsilyl, alkyldiphenylsilyl or dialkylphenylsilyl radical, Rb represents a phenyl radical optionally substituted by at least one alkoxy radical and Rc represents an alkyl or phenyl radical, or a stereoisomer of such a derivative, followed by deprotection of the hydroxyls. The compounds in which $R_1$, $R_2$, $R_4$, $R_5$ and $R_6$ each represent a —CHOH— radical, $R_3$ represents a methylene radical, $R_9$ represents a —CH$_2$F or —CH$_2$OH radical, $R_{10}$ represents a —CH$_2$F or —CH$_2$OH radical but $R_9$ and $R_{10}$ not both being a —CH$_2$OH radical are obtained as a mixture with the compounds prepared from the intermediate (IV).

This fluorination is generally carried out according to the operating conditions described by W. J. Middleton, J. Org. Chem., 40, 574 (1975). The fluorination is preferably carried out by means of a dialkylaminosulphide trifluoride (diethylaminosulphide trifluoride, for example) in an inert solvent, such as a chlorinated solvent (for example dichloromethane) or an ether (for example tetrahydrofuran), at a temperature of between −78° C. and 20° C. The deprotection is carried out as mentioned above.

The compounds of formula (I) in which $R_9$ and $R_{10}$ each represent a —CH$_2$OH radical and either $R_3$ represents a methylene radical, $R_4$ represents a —CHOH— radical and one of the $R_1$, $R_2$, $R_5$ and $R_6$ radicals represents a —CH(NHR$_7$)— radical and the others each represent a —CHOH— radical or $R_1$ and $R_6$ each represent a —CHOH— radical, $R_3$ represents a methylene radical and $R_2$, $R_4$ and $R_5$ are identical and each represent a —CH(NHR$_7$)— radical or $R_2$ and $R_5$ each represent a —CHOH— radical, $R_3$ represents a methylene radical and $R_1$, $R_4$ and $R_6$ are identical and each represent a —CH(NHR$_7$)— radical can be prepared by reduction of a derivative chosen from the formulae:

(IIa)

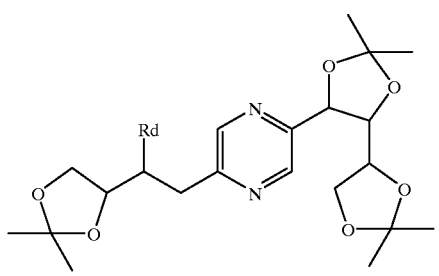

(IIIa)

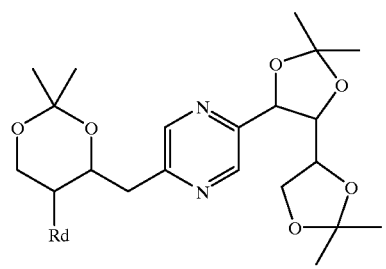

(IVa)

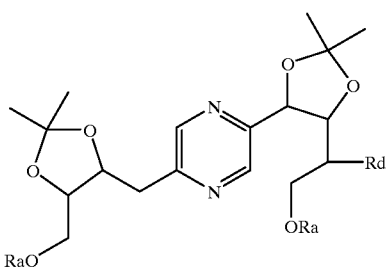

(Va)

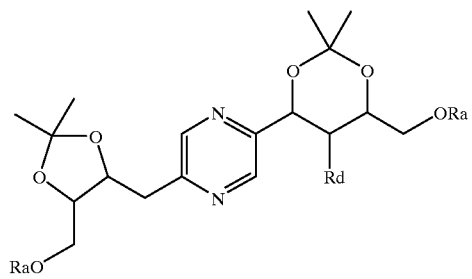

(VIa)

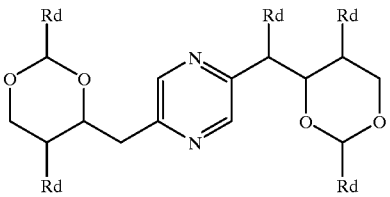

(VIIa)

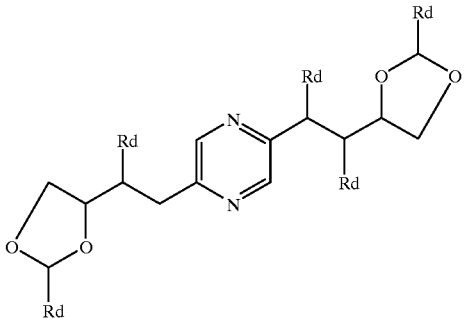

-continued

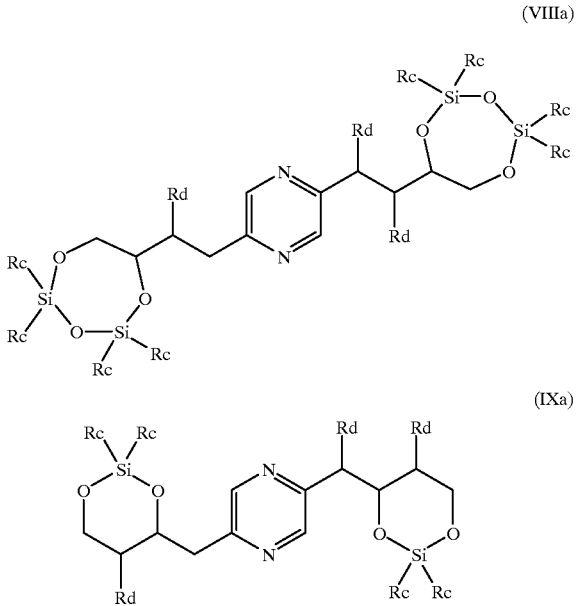

(VIIIa)

(IXa)

in which Ra represents a trialkylsilyl, alkyldiphenylsilyl or dialkylphenylsilyl radical, Rb represents a phenyl radical optionally substituted by at least one alkoxy radical, Rc represents an alkyl or phenyl radical and Rd represents an azido radical, or a stereoisomer of such a derivative, optionally followed by the reaction with a derivative of formula $HalR_7$, in which $R_7$ has the same meanings as in the formula (I), except hydrogen, and Hal represents a halogen atom, and followed by deprotection of the hydroxyls.

The reduction is generally carried out according to the reaction conditions described by R. C. Larock, Comprehensive Organic Transformations, VCH Publications (1989). The reaction is preferably carried out either by means of hydrogen in the presence of a catalyst, such as palladium, in an inert solvent, such as a 1–4C aliphatic alcohol (for example methanol), at a temperature in the region of 20° C., or else by means of an alkali metal hydride (alkali metal borohydride, such as sodium borohydride) or lithium aluminium hydride, in an inert solvent, such as an ether (for example, tetrahydrofuran or diethyl ether), at a temperature of between –78° C. and 100° C.

The reaction with the $HalR_7$ derivative is generally carried out according to the reaction conditions described by R. C. Larock, Comprehensive Organic Transformations, VCH Publications (1989). The reaction is preferably carried out in the presence of an organic base, such as an amine (trialkylamine, such as triethylamine, or pyridine), or an organometallic base, such as an alkali metal (sodium or lithium, for example) dialkylamide or an alkali metal hydride (sodium hydride, for example), or of an inorganic base, such as an alkali metal hydroxide (for example, sodium hydroxide or potassium hydroxide), in an inert solvent, such as an ether (for example, diethyl ether, tetrahydrofuran or dioxane), a 1–4C aliphatic alcohol (for example, methanol or ethanol), a chlorinated solvent (for example dichloromethane), dimethylformamide or dimethyl sulphoxide, at a temperature of between 0° C. and the boiling temperature of the reaction mixture.

The deprotection is carried out as mentioned above.

The derivatives of formulae (IIa), (IIIa), (IVa), (Va), (VIa), (VIIa), (VIIIa) and (IXa), in which Ra represents a trialkylsilyl, alkyldiphenylsilyl or dialkylphenylsilyl radical, Rb represents a phenyl radical optionally substituted by at least one alkoxy radical, Rc represents an alkyl or phenyl radical and Rd represents an azido radical, and their stereoisomers can be obtained by reaction of an alkali metal (preferably sodium) azide with a derivative of formula (IIa), (IIIa), (IVa), (Va), (VIa), (VIIa), (VIIIa) or (IXa), in which Ra represents a trialkylsilyl, alkyldiphenylsilyl or dialkylphenylsilyl radical, Rb represents a phenyl radical optionally substituted by at least one alkoxy radical, Rc represents an alkyl or phenyl radical and Rd represents an —$OSO_2$—Re radical in which Re represents a methyl, trifluoromethyl or 4-methylphenyl radical, or a stereoisomer of such a derivative.

This reaction is generally carried out according to the operating conditions described by A. C. Richardson, Methods Carbohydr. Chem., 6, 218 (1972). The reaction is preferably carried out in an inert solvent, such as dimethylformamide, at a temperature between 0° C. and 100° C.

The derivatives of formulae (IIa), (IIIa), (IVa), (Va), (VIa), (VIIa), (VIIIa) and (IXa), in which Ra represents a trialkylsilyl, alkyldiphenylsilyl or dialkylphenylsilyl radical, Rb represents a phenyl radical optionally substituted by at least one alkoxy radical, Rc represents an alkyl or phenyl radical and Rd represents an —$OSO_2$—Re radical, and their stereoisomers can be prepared by reaction of a $ClSO_2Re$ or $(ReSO_2)_2O$ derivative, in which Re has the same meanings as above, with a derivative of formula (II), (III), (IV), (V), (VI), (VII), (VIII) or (IX), in which Ra represents a trialkylsilyl, alkyldiphenylsilyl or dialkylphenylsilyl radical, Rb represents a phenyl radical optionally substituted by at least one alkoxy radical and Rc represents an alkyl or phenyl radical, or a stereoisomer of such a derivative.

This reaction is generally carried out according to the operating conditions described by A. C. Richardson, Methods Carbohydr. Chem., 6, 218, (1972) and H. Paulsen, Liebigs Ann. Chem., 735 (1992). The reaction is preferably carried out in an inert solvent, such as a chlorinated solvent (for example dichloromethane), in the presence of an organic base, such as pyridine, at a temperature of between –20° C. and 20° C.

The compounds of formula (I) in which $R_9$ and $R_{10}$ each represent a —$CH_2OH$ radical and either $R_3$ represents a methylene radical, $R_4$ represents a —CHOH— radical and one of the $R_1$, $R_2$, $R_5$ and $R_6$ radicals represents a —CH($OR_8$)— radical and the others each represent a —CHOH— radical or $R_1$ and $R_6$ each represent a —CHOH— radical, $R_3$ represents a methylene radical and $R_2$, $R_4$ and $R_5$ are identical and each represent a —CH($OR_8$)— radical or $R_2$ and $R_5$ each represent a —CHOH— radical, $R_3$ represents a methylene radical and $R_1$, $R_4$ and $R_6$ are identical and each represent a —CH($OR_8$)— radical can be prepared by reaction of a derivative of formula (II), (III), (IV), (V), (VI), (VII), (VIII) or (IX) or a stereoisomer of such a derivative with an $HalR_8$ derivative in which $R_8$ has the same meanings as in the formula (I).

This reaction is generally carried out according to the reaction conditions described [lacuna] R. C. Larock, Comprehensive Organic Transformations, VCH Publications (1989). The reaction is preferably carried out in the presence of an organic base, such as an amine (trialkylamine, such as triethylamine, or pyridine), an organometallic base, such as an alkali metal dialkylamide (lithium diisopropylamide, for example) or an alkali metal hydride (sodium hydride, for example), or an inorganic base (alkali metal hydroxide (for example, sodium hydroxide or potassium hydroxide)), in an inert solvent, such as an ether (for example, tetrahydrofuran or diethyl ether), an aliphatic alcohol (for example, methanol or ethanol), a chlorinated solvent (for example dichloromethane), dimethylformamide or dimethyl sulphoxide, at a temperature of between 0° C. and the boiling temperature of the reaction mixture.

The deprotection is carried out as mentioned above.

The compounds of formula (I) in which $R_1$, $R_4$, $R_5$ and $R_6$ each represent a —CHOH— radical and —$R_2$—$R_3$— represents a —CH═CH— radical can be prepared by dehydration of a derivative of formula (IIa), in which Rd represents an —OH or —$OSO_2$—Re radical in which Re represents a methyl, trifluoromethyl or 4-methylphenyl radical, or a stereoisomer of such a derivative, then deprotection of the hydroxyls.

This reaction is generally carried out according to the reaction conditions described [lacuna] R. C. Larock, Comprehensive Organic Transformations, VCH Publications (1989). The reaction is preferably carried out by means of an organic base, such as an amine (trialkylamine, such as triethylamine, or 1,8 -diazabicyclo[5.4.0]undec-7-ene), an organometallic base (alkali metal alkoxide, such as sodium ethoxide) or an alkali metal or alkaline earth metal dialkylamide (for example, lithium diisopropylamide), or of an inorganic base, such as an alkali metal hydroxide (for example, sodium hydroxide or potassium hydroxide), in an inert solvent, such as a 1–4C aliphatic alcohol (for example, methanol or ethanol), an ether (for example, diethyl ether or tetrahydrofuran), a chlorinated solvent (for example dichloromethane) or dimethylformamide, at a temperature of between 0° C. and the boiling temperature of the reaction mixture. This reaction can also be carried out according to the reaction conditions described by O. Mitsunobu, Synthesis, p.1 (1981). The reaction is preferably carried out in organic medium in an inert solvent, such as an ether (for example, diethyl ether or tetrahydrofuran), in the presence of trialkylphosphine (for example triphenylphosphine) and of dialkyl azodicarboxylate (for example, diethyl azocarboxylate), at a temperature of between 0° C. and the boiling temperature of the reaction mixture. The various stereoisomers of the compounds of formula (I) are obtained from the corresponding stereoisomers of the various intermediates (II), (III), (IV), (V), (VI), (VII), (VIII) or (IX). It is understood by a person skilled in the art that, for the implementation of the processes according to the invention described above, it may be necessary to introduce protective groups for the amino, hydroxyl and carboxyl functional groups, in order to avoid side reactions. These groups are those which can be removed without affecting the remainder of the molecule. Mention may be made, as examples of protective groups for the amino functional group, of tert-butyl or methyl carbamates which can be regenerated by means of iodotrimethylsilane. Mention may be made, as examples of protective groups for the hydroxyl functional group, of trialkylsilyl (for example triethylsilyl) or benzyl. Mention may be made, as protective groups for the carboxyl functional groups, of esters (for example, methoxymethyl ester, tetrahydropyranyl ester or benzyl ester), oxazoles and 2-alkyl-1,3-oxazolines. Other protective groups which can be used in these processes are also described by W. Greene et al., Protective Groups in Organic Synthesis, second edition, 1991, John Wiley & Sons, and P. J. Kocienski, Protecting Groups, published by Thieme Verlag (1994).

The reaction mixtures obtained by the various processes described above are treated according to conventional physical (evaporation, extraction, distillation, chromatography or crystallization, for example) or chemical (formation of salts, for example) methods.

The compounds of formula (I) can optionally be converted to addition salts with an inorganic or organic acid by the action of such an acid in an organic solvent, such as an alcohol, a ketone, an ether or a chlorinated solvent.

The compounds of formula (I) comprising an acid residue can optionally be converted to metal salts or to addition salts with nitrogenous bases according to methods known per se. These salts can be obtained by the action of a metal base (for example, alkali metal or alkaline earth metal base), of ammonia, of an amine or of a salt of an amine on a compound of formula (I) in a solvent. The salt formed is separated by the usual methods.

These salts also form part of the invention.

Mention may be made, as examples of pharmaceutically acceptable salts, of the addition salts with inorganic or organic acids (such as acetate, propionate, succinate, benzoate, fumarate, maleate, oxalate, methanesulphonate, isethionate, theophyllinacetate, salicylate, methylenebis(β-oxynaphthoate), hydrochloride, sulphate, nitrate and phosphate), the salts with alkali metals (sodium, potassium or lithium) or with alkaline earth metals (calcium or magnesium), the ammonium salt or the salts of nitrogenous bases (ethanolamine, trimethylamine, methylamine, benzylamine, N-benzyl-β-phenethylamine, choline, arginine, leucine, lysine or N-methylglucamine).

The following examples illustrate the invention:

EXAMPLE 1

50 $cm^3$ of an 80% aqueous trifluoroacetic acid solution are added to 349 mg of 2-[2,2-dimethyl-[1,3]dioxolan-4S-ylethyl]-5-[2,2,2',2'-tetramethyl-[4R,4'R]bi[[1,3]dioxolanyl]-5S-yl]pyrazine. The reaction mixture is stirred at a temperature of approximately 25° C. for 4 hours. After concentrating under reduced pressure (2.7 kPa) at a temperature of 50° C. the residual oil is taken up in 10 $cm^3$ of toluene and reconcentrated under the same conditions. The oil obtained is taken up in 2 $cm^3$ of absolute ethanol and placed in an ice bath for 2 hours. The precipitate obtained is filtered on sintered glass, pulled dry and then dried in a desiccator under reduced pressure (2.7 kPa) at a temperature of 25° C. A beige solid is obtained which is recrystallized from a water/absolute ethanol (1:8 by volume) mixture. The crystals are filtered on sintered glass, washed with 0.2 $cm^3$ of absolute ethanol, pulled dry and then dried under reduced pressure (2.7 kPa) at a temperature of 40° C. 158 mg of 1-[5-(3S,4-dihydroxybutyl)pyrazin-2-yl]butane-1R,2S,3R, 4-tetraol are thus isolated in the form of an ivory-coloured crystalline powder melting at 171° C. $^1$H N.M.R. spectrum (400 MHz, d6-$(CD_3)_2SO$, δ in ppm): 1.63 and 1.88 (2 mts, each 1H, 5β $CH_2$), 2.79 and 2.86 (2 mts, each 1H, 5α $CH_2$), from 3.20 to 3.70 (mt, 7H, 2β CH, 2γ CH, 5γ CH, 2δ $CH_2$ and 5δ $CH_2O$), 4.38 and 4.51 (respectively broad t and t, J=6 Hz, each 1H, OH at 2δ and OH at 5δ), 4.43 (d, J=7.5 Hz, 1H, OH), 4.58 (d, J=5 Hz, 1H, OH), 4.65 (d, J=5 Hz, 1H, OH), 4.95 (broad d, J=6 Hz, 1H, 2α CH), 5.31 (d, J=6 Hz, 1H, OH at 2α), 8.43 (s, 1H, ═CH at 6), 8.63 (s, 1H, ═CH at 3);

$$\alpha \frac{20}{D} = -55.9 \pm 1.5 (c = 0.36, water)].$$

2-[2,2-Dimethyl-[1,3]dioxolan-4R-ylethyl]-5-[2,2,2',2'-tetramethyl-[4R,4'R]bi[[1,3]dioxolanyl]-5S-yl] pyrazine is prepared according to the following method: A solution of 1.1 cm³ of tributyltin hydride and 13 mg of 2,2'-azobis(2-methylpropionitrile) in 14 cm³ of toluene is added under argon to a solution of 0.72 g of 1S-2,2-dimethyl-[1,3]dioxolan-4R-yl)-2-[5-(2,2,2', 2'-tetramethyl-[4R,4'R]bi[[1,3]dioxolanyl]-5S-yl) pyrazin-2-yl]ethyl phenyl thionocarbonate in 56 cm³ of toluene. The reaction mixture is heated at a temperature of 80° C. for 45 minutes and then at reflux at a temperature of approximately 110° C. for 70 hours. After filtering through a paper filter, the mixture is concentrated under reduced pressure (2.7 kPa) at a temperature of 40° C. The residual oil is chromatographed on a silica (0.020–0.045 mm) column eluted with an ethyl acetate/cyclohexane (1/4 by volume) mixture at a pressure of approximately 1.5★10⁵ Pa. The fractions containing the expected product are combined and concentrated under reduced pressure (2.7 kPa) at a temperature of 40° C. 0.36 g of 2-[2,2-dimethyl-[1,3]dioxolan-4S-ylethyl]-5-[2,2,2',2'-tetramethyl-[4R,4'R]bi[[1,3]dioxolanyl]-5S-yl] pyrazine is thus obtained in the form of a yellow oil (Rf=0.5; silica gel thin layer chromatography; eluent ethyl acetate/cyclohexane (1/1 by volume) mixture.

1S-(2,2-Dimethyl-[1,3]dioxolan-4R-yl)-2-[5-(2,2,2',2'-tetramethyl-[4R,4'R]bi[[1,3]dioxolanyl]-5S-yl)pyrazin-2-yl]ethyl phenyl thionocarbonate is prepared according to the following method: 2 cm³ of pyridine, 0.021 g of 4-dimethylaminopyridine and 0.35 cm³ of phenyl chlorothionocarbonate are successively added to a solution of 0.72 g of 1S-(2,2-dimethyl-[1,3]dioxolan-4R-yl)-2-[5-(2,2, 2',2'-tetramethyl-[4R,4'R]bi[[1,3]dioxolanyl]-5S-yl) pyrazin-2-yl]ethanol in 50 cm³ of dichloromethane. The reaction mixture is stirred at a temperature of approximately 25° C. for 1 day and is then diluted with a mixture of 20 cm³ of water and 20 cm³ of dichloromethane. After separation by settling, the organic phase is washed three times with 20 cm³ of water, dried over magnesium sulphate and then concentrated under reduced pressure (2.7 kPa) at a temperature in the region of 45° C. The residual oil is chromatographed on a silica (0.020–0.045 mm) column eluted with an ethyl acetate/cyclohexane (1/4 by volume) mixture at a pressure of approximately 1.5★10⁵ Pa. The fractions containing the expected product are combined and concentrated under reduced pressure (2.7 kPa) at a temperature of 40° C. 0.74 g of 1S-(2,2-dimethyl-[1,3]dioxolan-4R-yl)-2-[5-(2,2,2',2'-tetramethyl-[4R,4'R]bi[[1,3] dioxolanyl]-5S-yl)pyrazin-2-yl]ethyl phenyl thionocarbonate is thus obtained in the form of a yellow oil (Rf=0.2; silica gel thin layer chromatography; eluent ethyl acetate/cyclohexane (1/4 by volume) mixture).

1S-(2,2-Dimethyl-[1,3]dioxolan-4R-yl)-2-[5-(2,2,2',2'-tetramethyl-[4R,4'R]bi[[1,3]dioxolanyl]-5S-yl)pyrazin-2-yl]ethanol is prepared according to the following method: 81 cm³ of 2,2-dimethoxypropane and then 0.3 g of para-toluenesulphonic acid are added, with stirring, to a solution of 10 g of deoxyfructosazine in 250 cm³ of dimethylformamide. The reaction mixture is stirred at a temperature of approximately 25° C. for 20 hours, 10 cm³ of 2,2-dimethoxypropane are then added again and stirring is continued for 3 hours. The mixture is then heated at a temperature of 50° C. for 21 hours. After concentrating under reduced pressure (2.7 kPa) at a temperature of 60° C., the residual oil is dissolved in 300 cm³ of dichloromethane and washed twice with 100 cm³ of a 5% aqueous sodium bicarbonate solution and then twice with 200 cm³ of water. The organic phase is dried over magnesium sulphate and then concentrated under reduced pressure (2.7 kPa) at a temperature of 40° C. The oil obtained is chromatographed on a silica (0.020–0.045 mm) column eluted with an ethyl acetate/cyclohexane (1/1 by volume) mixture at a pressure of approximately 1.5★10⁵ Pa. The fractions containing the expected products are combined and concentrated under reduced pressure (2.7 kPa) at a temperature of 40° C. 5.2 g of 1S-(2,2-dimethyl-[1,3]dioxolan-4R-yl)-2-[5-(2,2,2',2'-tetramethyl- [4R,4'R]bi[[1,3]dioxolanyl]-5S-yl) pyrazin-2-yl]ethanol are thus obtained in the form of a white solid, as well as 2.4 g of the same impure product. The latter is recrystallized from a water/absolute ethanol (5/1 by volume) mixture. 0.6 g of 1S-(2,2-dimethyl-[1,3]dioxolan-4R-yl)-2-[5-(2,2,2',2'-tetramethyl-[4R,4'R]bi[[1,3] dioxolanyl]-5S-yl)pyrazin-2-yl]ethanol is thus isolated in the form of white crystals melting at 74° C. [¹H N.M.R. spectrum (400 MHz, d6-(CD₃)₂SO, δ in ppm): 1.04, 1.20, 1.28, 1.33 and 1.44 (5s, respectively 3H, 3H, 3H, 3H and 6H, the 6 CH₃), 2.79 (dd, J=13 and 9 Hz, 1H, 1H of the 5α CH₂), 3.06 (dd, J=13 and 2.5 Hz, 1H, the other H of the 5α CH₂), 3.79 (unresolved peak, 1H, 5β CH), from 3.80 to 3.90 (mt, 2H, 1H of the 2δ CH₂ and 1H of the 5δ CH₂), 3.91 (mt, 1H, 5γ CH), 4.00 (t, J=7 Hz, 1H, the other H of the 5δ CH₂), 4.06 (t, J=7.5 Hz, 1H, the other H of the 2δ CH₂), 4.28 (mt, 1H, 2γ CH), 4.33 (t, J=7 Hz, 1H, 2β CH), 4.99 (d, J=7.5 Hz, 1H, 2α CH), 5.07 (broad d, J=5 Hz, 1H, OH at 5β), 8.54 (s, 1H, =CH at 6), 8.66 (s, 1H, =CH at 3);

$$\alpha \frac{20}{D} = +6.7 \, \text{°} \, \text{1.1}(c = 0.5, \text{dichloromethane});$$

(Rf=0.36; silica gel thin layer chromatography; eluent ethyl acetate/cyclohexane 1/1 by volume mixture)].

1.4 g of 2,2-dimethyl-4S-[5-(2,2,2',2'-tetramethyl-[4R, 4'R]bi[[1,3]dioxolanyl]-5S-yl)pyrazin-2-ylmethyl]-[1,3] dioxan-5R-ol are also isolated from this column in the form of a yellow oil [¹H N.M.R. spectrum (400 MHz, d6-(CD₃)₂SO, δ in ppm): 0.95, 1.18, 1.28 and 1.44 (4 s, respectively 3H, 6H, 3H and 6H, the 6 CH₃), 2.83 (dd, J=13 and 9 Hz, 1H, 1H of the 5α CH₂), 3.29 (dd, J=13 and 2.5 Hz, 1H, the other H of the 5α CH₂), from 3.30 to 3.40 (mt, 1H, 5γ CH), 3.53 (t, J=11 Hz, 1H, 1H of the 5δ CH₂), 3.74 (dd, J=11 and 5.5 Hz, 1H, the other H of the 5δ CH₂), 3.84 (dd, J=9 and 4 Hz, 1H, 1H of the 2δ CH₂), from 3.95 to 4.15 (mt, 2H, the other H of the 2δ CH₂ and 5β CH), from 4.20 to 4.35 (mt, 2H, 2β CH and 2γ CH), 4.98 (d, J=7 Hz, 1H, 2α CH), 5.20 (d, J=6 Hz, 1H, OH at 5γ), 8.53 (s, 1H, =CH at 6), 8.66 (s, 1H, =CH at 3);

$$\alpha \frac{20}{D} = -23.8 \, \text{°} \, \text{1.1}(c = 0.5, \text{dichloromethane});$$

(Rf=0.28; silica gel thin layer chromatography; eluent ethyl acetate/cyclohexane 1/1 by volume mixture)].

Deoxyfructosazine can be prepared according to the method described by K. Sumoto et al. in Chem. Pharm. Bull., 39, 792 (1991).

EXAMPLE 2

100 cm³ of an 80% aqueous trifluoroacetic acid solution are added to 0.72 g of 2-(2,2,2',2'-tetramethyl-[4R,4'R]bi[[1, 3]dioxolanyl]-5S-yl)-5-(2-[2,2-dimethyl-[1,3]dioxolan-4S-yl]-E-ethenyl)pyrazine. The reaction mixture is stirred at a temperature of approximately 25° C. over 2.5 hours. After concentrating under reduced pressure (2.7 kPa) at a temperature of 50⁺ C., the residual brown paste is taken up in a mixture of 10 cm³ of ethanol and 1 cm³ of water and recrystallized. The precipitate obtained is filtered on sintered glass, rinsed with the same cold mixture, pulled dry and then dried in a desiccator under reduced pressure (2.7 kPa) at a temperature in the region of 60⁺ C. 200 mg of 1-[5-(3S, 4-dihydroxy-1E-butenyl)pyrazin-2-yl]butane-1R,2S,3R,4-tetraol are thus isolated in the form of off-white-coloured crystals melting at 192⁺ C. [¹H N.M.R. spectrum (400 MHz, d6-(CD₃)₂SO, δ in ppm): from 3.20 to 3.50 (mt, 3H, 1H of the 2δ CH₂O and 5δ CH₂O), from 3.55 to 3.70 (mt, 3H, the other H of the 2δ CH₂O, 2β CH and 2γ CH), 4.23 (mt, 1H, 5γ CH), 4.39 (t, J=6 Hz, 1H, OH at 2δ), 4.46 (d, J=7 Hz, 1H, OH), 4.66 (d, J=4 Hz, 1H, OH), 4.75 (t, J=6 Hz, 1H, OH at 5δ), 4.96 (broad d, J=6.5 Hz, 1H, 2α CH), 5.12 (d, J=5 Hz, 1H, OH at 5γ), 5.34 (d, J=6.5 Hz, 1H, OH at 2α), 6.74 (broad d, J=16 Hz, 1H, 5α =CH), 6.91 (dd, J=16 and 4.5 Hz, 1H, 5β =CH), 8.58 (s, 1H, =CH at 6), 8.66 (s, 1H, =CH at 3);

$$\alpha \frac{20}{D} = -29.7 \text{ } +/-1.0 (c = 0.5, \text{water})].$$

2-(2,2,2',2'-Tetramethyl-[4R,4'R]bi[[1,3]-dioxolanyl]-5S-yl)-5-(2-[2,2-dimethyl-[1,3]dioxolan-4S-yl]-E-ethenyl)pyrazine is prepared according to the following method: 132 mg of succinimide and 340 mg of triphenylphosphine are successively added to a solution of 0.5 g of 1S-(2,2-dimethyl-[1,3]dioxolan-4R-yl)-2-[5-(2,2,2',2'-tetramethyl-[4R,4'R]bi[[1,3]dioxolanyl]-5S-yl)pyrazin-2-yl]ethanol in 9.6 cm³ of tetrahydrofuran. A 40% solution of diethyl azodicarboxylate in toluene (0.62 cm³) is subsequently added dropwise and the reaction mixture is stirred at a temperature in the region of 25⁺ C. for 4 hours, on conclusion of which 396 mg of succinimide, 1.02 g of triphenylphosphine and 1.87 cm³ of 40% solution of diethyl azodicarboxylate in toluene are again added. After stirring for 48 hours, the reaction mixture is concentrated under reduced pressure (2.7 kPa) at a temperature in the region of 45⁺ C. The residue obtained is chromatographed on a silica (0.020–0.045 mm) column eluted with an ethyl acetate/cyclohexane (1/4 then 1/2.3 by volume) mixture at a pressure of approximately 1.5★10⁵ Pa. The fractions containing the expected product are combined and concentrated under reduced pressure (2.7 kPa) at a temperature of 45⁺ C. 340 mg of 2-(2,2,2',2'-tetramethyl-[4R,4'R]bi[[1,3]dioxolanyl]-5S-yl)-5-(2-[2,2-dimethyl-[1,3]dioxolan-4S-yl]-E-ethenyl)pyrazine are thus obtained in the form of a viscous whitish oil (Rf=0.7; silica gel thin layer chromatography; eluent ethyl acetate).

EXAMPLE 3

62 cm³ of an 80% aqueous trifluoroacetic acid solution are added to 0.45 g of 2-(2,2,2',2'-tetramethyl-[4R,4'R]bi[[1,3]dioxolanyl]-5S-yl)-5-(2S-[2,2-dimethyl-[1,3]dioxolan-4R-yl]-2-methoxyethyl)pyrazine. The reaction mixture is stirred at a temperature of approximately 25⁺ C. for 2 hours. After concentrating under reduced pressure (2.7 kPa) at a temperature of 25⁺ C., the residual brown lacquer is taken up 3 times in ether and then reconcentrated under reduced pressure (2.7 kPa) at a temperature of 45⁺ C. The residual paste is taken up in 4 cm³ of ethanol and recrystallized. The precipitate obtained is filtered on sintered glass, washed with ethanol, pulled dry and then dried under reduced pressure (2.7 kP) at a temperature of 40⁺ C. 100 mg of 1-[5-(2S-methoxy-3R,4-dihydroxybutyl)pyrazin-2-yl]butane-1R,2S,4-tetraol are thus isolated in the form of a beige crystalline powder melting at 144⁺ C. [¹H N.M.R. spectrum (400 MHz, d6-(CD₃)₂SO, δ in ppm): 2.92 and 3.02 (2 dd, respectively J=14 and 8 Hz and J=14 and 4 Hz, each 1H, 5α CH₂), 3.14 (s, 3H, OCH₃ at 5β), from 3.30 to 3.50 and from 3.50 to 3.60 (2 mts, respectively 2H and 6H, 2β CH, 2γ CH, 2δ CH₂O, 5β CH, 5γ CH and 5δ CH₂O), 4.39 and 4.53 (2 t, J=5.5 Hz, each 1H, OH at 2δ and OH at 5δ), 4.45 (d, J=7.5 Hz, 1H, OH), 4.65 (broad d, J=5 Hz, 1H, OH), 4.70 (d, J=5 Hz, 1H, OH), 4.95 (d, J=6.5 Hz, 1H, 2α CH), 5.31 (d, J=6.5 Hz, 1H, OH at 2α), 8.43 (broad s, 1H, =CH at 6), 8.65 (broad s, 1H, =CH at 3)].

2-(2,2,2',2'-Tetramethyl-[4R,4'R]bi[[1,3]-dioxolanyl]-5S-yl)-5-(2S-[2,2-dimethyl-[1,3]dioxolan-4R-yl]-2-methoxyethyl)pyrazine is prepared according to the following method: a suspension of 104 g of sodium hydride (at 60% in oil) in 5 cm³ of dimethylformamide is added to a solution of 1.0 g of 1S-(2,2-dimethyl-[1,3]dioxolan-4R-yl)-2-[5-(2,2,2',2'-tetramethyl-[4R,4'R]bi[[1,3]dioxolanyl]-5S-yl)pyrazin-2-yl]ethanol in 5 cm³ of dimethylformamide. The reaction mixture is stirred at a temperature in the region of 25⁺ C. for 30 minutes and then 0.15 cm³ of methyl iodide is added. After stirring for 48 hours, the reaction mixture is treated with 25 cm³ of water and 25 cm³ of ethyl acetate and then separated by settling. The aqueous phase is extracted twice with 25 cm³ of ethyl acetate and the organic extracts are combined, dried over magnesium sulphate and then concentrated under reduced pressure (2.7 kPa) at a temperature in the region of 45⁺ C. The residue obtained is chromatographed on on a silica (0.020–0.045 mm) column eluted with an ethyl acetate/cyclohexane (1/2.3 by volume) mixture. The fractions containing the expected product are combined and concentrated under reduced pressure (2.7 kPa) at a temperature in the region of 50⁺ C. 0.45 g of 2-(2,2,2',2'-tetramethyl-[4R,4'R]bi[[1,3]dioxolanyl]-5S-yl)-5-(2S-[2,2-dimethyl-[1,3]dioxolan-4R-yl]-2-methoxyethyl)pyrazine is thus obtained in the form of a beige solid (Rf=0.6; silica gel thin layer chromatography; eluent ethyl acetate/cyclohexane (1/1 by volume) mixture).

EXAMPLE 4

100 cm³ of an 80% aqueous trifluoroacetic acid solution are added to 0.58 g of 2-(2,2,2',2'-tetramethyl-[4R,4'R]bi[[1,3]dioxolanyl]-5S-yl)-5-(2R-[2,2-dimethyl-[1,3]dioxolan-4R-yl]-2-fluoroethyl)pyrazine. The reaction mixture is stirred at a temperature of approximately 25⁺ C. for 16 hours. After concentrating under reduced pressure (2.7 kpa) at a temperature of 25⁺ C., the residual oil is chromatographed on a silica (0.020–0.045 mm) column eluted with an ethanol/n-butanol/aqueous ammonia solution (8/1/1 by volume) mixture. The fractions containing the expected products are combined and concentrated under reduced pressure (2.7 kPa) at a temperature of 50⁺ C. 1-[5-(2R-Fluoro-3R,4-dihydroxybutyl)pyrazin-2-yl]butane-1R,2S,3R,4-tetraol is thus obtained in the form of a sand-coloured solid which is taken up in a mixture of 1.2 cm³ of ethanol and 0.2 cm³ of water and recrystallized. The precipitate obtained is filtered on sintered glass, washed with diethyl ether, pulled dry and then dried under reduced pressure (2.7 kPa) at a temperature of 60⁺ C. 62 mg of 1-[5-(2R-fluoro-3R,4-dihydroxybutyl)pyrazin-2-yl]butane-1R,2S,3R,4- tetraol are thus isolated in the form of white crystals melting at 172° C. [$^1$H N.M.R. spectrum (400 MHz, d6-(CD$_3$)$_2$SO, at a temperature of 303 K, δ in ppm): from 3.00 to 3.40 (mt, 2H, 5α CH$_2$), from 3.40 to 3.70 (mt, 7H, 2β CH, 2γ CH, 2δ CH$_2$O, 5γ CH and 5δ CH$_2$O), 4.38 and 4.73 (2 broad t, J=5 Hz, each 1H, OH at 2δ and OH at 5δ), 4.46 (d, J=7 Hz, 1H, OH), 4.66 (d, J=5 Hz, 1H, OH), 4.96 (broad d, J=5.5 Hz, 1H, 2α CH), 5.02 (decoupled d, J$_{HF}$=44 Hz, 1H, 5β CH), 5.35 (d, J=5.5 Hz, 1H, OH at 2α), 8.47 (broad s, 1H, =CH at 6), 8.69 (broad s, 1H, =CH at 3)].

2-(2,2,2',2'-Tetramethyl-[4R,4'R]bi[[1,3]-dioxolanyl]-5S-yl)-5-(2R-[2,2-dimethyl-[1,3]dioxolan-4R-yl]-2-fluoroethyl)pyrazine is prepared according to the following method: 1.25 cm$^3$ of diethylaminosulphide trifluoride are added dropwise to a solution, cooled to a temperature in the region of −78° C. and under nitrogen, of 2.0 g of 1S-(2,2-dimethyl-[1,3]dioxolan-4R-yl)-2-[5-(2,2,2',2'-tetramethyl-[4R,4'R]bi[[1,3]-dioxolanyl]-5S-yl)pyrazin-2-yl]ethanol in 40 cm$^3$ of tetrahydrofuran. The reaction mixture is allowed to return to a temperature of approximately −10° C. After 4 hours at this temperature of −10° C., the reaction mixture is treated with 60 cm$^3$ of methanol, then stirred for 30 minutes and concentrated under reduced pressure (2.7 kPa) at a temperature in the region of 40° C. The residual brown oil is chromatographed on a silica (0.020–0.045 mm) column eluted with an ethyl acetate/cyclohexane (1/3 by volume) mixture. The fractions containing the expected products are combined and concentrated under reduced pressure (2.7 kPa) at a temperature in the region of 40° C. 0.67 g of a mixture of 2-(2,2,2',2'-tetramethyl-[4R,4'R]bi[[1,3]-dioxolanyl]-5S-yl)-5-(2R-[2,2-dimethyl-[1,3]dioxolan-4R-yl]-2-fluoroethyl)pyrazine and 2-(2,2,2',2'-tetramethyl-[4R,4'R]bi[[1,3]dioxolanyl]-5S-yl)-5-{2S-[2,2-dimethyl-[1,3]dioxolan-4R-yl]-2-(4-fluorobutoxy)ethyl}pyrazine in the approximate proportions 1:1 is thus obtained in the form of a colourless oil (Rf=0.3 for the 2 products; silica gel thin layer chromatography; eluent ethyl acetate/cyclohexane (1/1 by volume) mixture).

EXAMPLE 5

51 cm$^3$ of an 80% aqueous trifluoroacetic acid solution are added to 0.36 g of 2-(2,2,2',2'-tetramethyl-[4R,4'R]bi[[1,3]dioxolanyl]-5S-yl)-5-([5R-methoxy-2,2-dimethyl-[1,3]dioxan-4S-yl]methyl)pyrazine. The reaction mixture is stirred at a temperature of approximately 25° C. for 18 hours. After concentrating under reduced pressure (2.7 kPa) at a temperature in the region of 60° C., the orange residual oil is taken up in 4 cm$^3$ of ethanol and recrystallized. The precipitate obtained is filtered on sintered glass, washed with ethanol, pulled dry and then dried under reduced pressure (2.7 kPa) at a temperature in the region of 40° C. 88 mg of 1-[5-(2S,4-dihydroxy-3R-methoxybutyl)pyrazin-2-yl]butane-1R,2S,3R,4-tetraol are thus isolated in the form of a beige crystalline powder melting at 96° C. [$^1$H N.M.R. spectrum (400 MHz, d6-(CD$_3$)$_2$SO, with addition of a few drops of d4—CD$_3$COOD, δ in ppm): 2.79 and 2.97 (2 dd, respectively J=14 and 9 Hz and J=14 and 3 Hz, each 1H, 5α CH$_2$), 3.10 (mt, 1H, 5γ CH), 3.38 (s, 3H, OCH$_3$ at 5γ), from 3.40 to 3.70 (mt, 4H, 2β CH, 2γ CH and 2δ CH$_2$O), 3.50 and 3.64 (respectively dd, J=5 and 12 Hz and mt, each 1H, 5δ CH$_2$O), 3.93 (mt, 1H, 5β CH), 4.95 (broad s, 1H, 2α CH), 8.40 (s, 1H, =CH at 6), 8.64 (s, 1H, =CH at 3)].

2-(2,2,2',2'-Tetramethyl-[4R,4'R]bi[[1,3]-dioxolanyl]-5S-yl)-5-([5R-methoxy-2,2-dimethyl-[1,3]-dioxan-4S-yl] methyl)pyrazine is prepared according to the following method: a solution of 1.24 g of 2,2-dimethyl-4S-[5-(2,2,2',2'-tetramethyl-[4R,4'R]-bi[[1,3]dioxolanyl]-5S-yl)pyrazin-2-ylmethyl]-[1,3]-dioxan-5R-ol in 15 cm$^3$ of dimethylformamide is added to a suspension, cooled to a temperature in the region of 0° C. and under nitrogen, of 0.14 g of sodium hydride (at 60% in oil) in 10 cm$^3$ of diemethylformamide. The reaction mixture is stirred at a temperature in the region of 0° C. for 30 minutes and then 0.19 cm$^3$ of methyl iodide is added. The reaction mixture is left to return to a temperature in the region of 25° C. After stirring for 16 hours, the reaction mixture is treated with 25 cm$^3$ of water and 25 cm$^3$ of ethyl acetate and then separated by settling. The aqueous phase is extracted twice with 25 cm$^3$ of ethyl acetate and the organic extracts are combined, dried over magnesium sulphate and then concentrated under reduced pressure (2.7 kPa) at a temperature of 50° C. The residue obtained is chromatographed on a silica (0.020–0.045 mm) column eluted with an ethyl acetate/cyclohexane (1/2.3 by volume) mixture. The fractions containing the expected product are combined and concentrated under reduced pressure (2.7 kPa) at a temperature of 50° C. 0.36 g of 2-(2,2,2',2'-tetramethyl-[4R,4'R]bi[[1,3]-dioxolanyl]-5S-yl)-5-([5R-methoxy-2,2-dimethyl-[1,3]-dioxan-4S-yl]methyl)pyrazine is thus obtained in the form of a colourless oil (Rf=0.5; silica gel thin layer chromatography; eluent ethyl acetate/cyclohexane (1/1 by volume) mixture).

EXAMPLE 6

I-12.5 cm$^3$ of an 80% aqueous trifluoroacetic acid solution are added to 573 mg of 2-(1R,2S)-2-[(2R)-1,4-dioxaspiro[4.5]dec-2-yl]-1,2-dimethoxyethyl-5-[(2S)-2-[(2R)-1,4-dioxaspiro[4.5]dec-2-yl]-2-methoxyethyl]pyrazine. The reaction mixture is stirred at a temperature of approximately 25° C. for 5.5 hours. After concentrating under reduced pressure (2.7 kPa) at a temperature of 45° C., the residual oil is taken up in 10 cm$^3$ of toluene and reconcentrated under the same conditions. The oil obtained is chromatographed on a silica (0.040–0.063 mm) column eluted with a dichloromethane/methanol (95/5 by volume) mixture and then with an ethanol/n-butanol/aqueous ammonia solution (8/2/1 by volume) mixture at a pressure of 1.6★10$^5$ Pa. The fractions containing the expected product are combined and concentrated under reduced pressure (2.7 kPa) at a temperature of 50° C. The oil thus obtained is taken up in ethanol, the solvent is evaporated, the residue is then triturated several times in dichloromethane and then taken up in toluene. The solvent is evaporated and the precipitate is filtered to give a yellowish solid, which is again triturated in dichloromethane. 135 mg of 4-[5-(3R,4-dihydroxy-2S-methoxybutyl)]pyrazin-2-yl]-3R,4R-dimethoxybutane-1,2-diol are thus obtained in the form of a pale yellow solid which melts at 84° C. $^1$H N.M.R. spectrum (400 MHz, d6-(CD$_3$)$_2$SO, δ in ppm): 2.82, 3.08 and 3.33 (3 s, each 3H, OCH$_3$), 2.93 and 3.05 (2 dd, respectively J=14 and 9 Hz and J=14 and 4 Hz, each 1H, 5α CH$_2$), from 3.30 to 3.50 (mt, the 3H corresponding to the 5δ CH$_2$O and 2β CH), from 3.50 to 3.70 (mt, 5H, 2γ CH, 2δ CH$_2$O, 5β CH and 5γ CH), 4.46 (t, J=5.5 Hz, 1H, OH at 2δ), 4.55 (t, J=5.5 Hz, 1H, OH at 5δ), 4.62 (d, J=2.5 Hz, 1H, 2α CH), 4.81 (mt, 2H, OH at 2γ and OH at 5γ), 8.52 (s, 1H, =CH at 6), 8.56 (s, 1H, =CH at 3)].

2-(1R,2S)-2-[(2R)-1,4-Dioxaspiro[4.5]dec-2-yl]-1,2-dimethoxyethyl-5-[(2S)-2-[(2R)-1,4-dioxaspiro[4.5]dec-2- yl]-2-methoxyethyl]pyrazine can be prepared in the following way: a solution of 0.5 g of 2-(1R,2S)-2-[(2R)-1,4-dioxaspiro[4.5]dec-2-yl]-1,2-dihydroxyethyl-5-[(2S)-2-[(2R)-1,4-dioxaspiro[4.5]dec-2-yl]-2-dihydroxyethyl]pyrazine in 7 cm³ of dimethylformamide is added to a suspension, under argon and at 0+C, of 150 mg of sodium hydride in 5 cm³ of dimethylform amide. The yellowish suspension is thus kept stirring for 0.5 hour and then 0.21 cm³ of methyl iodide is slowly added. The temperature is subsequently raised to 15+ C. and 25 cm³ of water are added dropwise. The reaction mixture is extracted with 3 times 25 cm³ of ethyl acetate. The organic phase is dried over magnesium sulphate, filtered and then concentrated under reduced pressure (2.7 kPa) at a temperature of 45+ C. 0.58 g of 2-(1R,2S)-2-[(2R)-1,4-dioxaspiro[4.5]-dec-2-yl]-1,2-dimethoxyethyl-5-[(2S)-2-[(2R)-1,4-dioxaspiro[4.5]dec-2-yl]-2-methoxyethyl]pyrazine is thus obtained in the form of a yellow oil used as is in the following stage.

2-(1R,2S)-2-[(2R)-1,4-Dioxaspiro[4.5]dec-2-yl]-1,2-dihydroxyethyl-5-[(2S)-2-[(2R)-1,4-dioxaspiro-[4.5]dec-2-yl]-2-dihydroxyethyl]pyrazine can be obtained in the following way: 2.54 cm³ of cyclohexanone and 31 mg of para-toluenesulphonic acid monohydrate are successively added, at a temperature in the region of 20+ C., to 500 mg of 2-[(1R,2S,3R)-(1,2,3,4-tetrahydroxybutyl)]-5-[(2'S,3'R)-(2',3',4'-trihydroxybutyl)]-pyrazine in suspension in 12 cm³ of dimethylformamide. The solution obtained after stirring for 15 min at a temperature in the region of 20+ C. is again stirred for 2 hours 30 minutes at a temperature in the region of 20+ C. Magnesium sulphate is subsequently added and the reaction mixture is stirred for an additional 16 hours at a temperature in the region of 20+ C. The mixture is subsequently heated at a temperature in the region of 60+ C. for a few minutes and becomes milky, white. The reaction mixture is allowed to return to a temperature in the region of 20+ C. and is diluted with a mixture of 10 cm³ of distilled water and 10 cm³ of ethyl acetate. The organic phase, after separation by settling, is washed with two times 10 cm³ of distilled water. The aqueous phases are recombined and extracted with one times 10 cm³ of ethyl acetate. The combined organic phases are dried over magnesium sulphate, filtred on sintered glass and then concentrated to dryness under reduced pressure (0.27 kPa) at a temperature in the region of 30+ C. 910 mg of a pale yellow foam are thus obtained, which foam is taken up in 10 cm³ of ethyl ether. After stirring for 10 minutes at a temperature in the region of 20+ C., the insoluble material is filtred on sintered glass and rinsed with 5 cm³ of ethyl ether to give a fluffy white product which is dried at a temperature in the region of 40+ C. under reduced pressure (0.27 kPa). 417 mg of 2-(1R,2S)-2-[(2R)-1,4-dioxaspiro[4.5]dec-2-yl]-1,2-dihydroxyethyl-5-[(2S)-2-[(2R)-1,4-dioxaspiro[4.5]dec-2-yl]-2-dihydroxyethyl]-pyrazine are thus obtained in the form of a white solid [¹H N.M.R. spectrum (400 MHz, d6-(CD₃)₂SO, δ in ppm): from 1.25 to 1.65 (unresolved peak, 20 H, the 10 CH₂ of the 2 cyclohexyls), 2.76 (dd, J=14 and 9 Hz, 1H, 1H of the 5α CH₂), 3.04 (dd, J=14 and 3.5 Hz, 1H, the other H of the 5α CH₂), 3.61 (dt, J=7 and 1.5 Hz, 1H, 2β CH), 3.77 (mt, 1H, 5β CH), from 3.80 to 3.95 and from 3.95 to 4.10 (2 mts, respectively 3H and 2H, 5γ CH, 2d CH₂O and 5δ CH₂O), 4.18 (mt, 1H, 2γ CH), 4.80 (mt, 2H, 2α CH and OH at 2β), 5.02 (d, J=7 Hz, 1H, OH at 5β), 5.54 (d, J=6.5 Hz, 1H, OH at 2α), 8.43 (s, 1H, =CH at 6), 8.65 (s, 1H, =CH at 3). II-4-[5-(3R,4-Dihydroxy-2S-methoxybutyl)] pyrazin-2-yl]-3R,4R-dimethoxybutane-1,2-diol can also be prepared in a similar way but from 1-{5-[2(S)-hydroxy-2-(2,2,4,4-tetraisopropyl-[1,3,5,2,4]trioxadisilepan-6(R)-yl)ethyl]pyrazin-2-yl}- 2-(2,2,4,4-tetraisopropyl-[1,3,5,2,4]trioxadisilepan-6(R)-yl)ethane-1(R),2(S)-diol.

1-{5-[2(S)-Hydroxy-2-(2,2,4,4-tetraisopropyl-[1,3,5,2,4]trioxadisilepan-6(R)-yl)ethyl]pyrazin-2-yl}-2-(2,2,4,4-tetraisopropyl-[1,3,5,2,4]trioxadisilepan-6(R)-yl)ethane-1(R),2(S)-diol can be obtained in the following way: 2.3 cm³ of 1,3-dichloro-1,1,3,3-tetraisopropyldisiloxane are added, with stirring, and under nitrogen, to a solution of 1 g of deoxyfructosazine in 27 cm³ of pyridine. The reaction mixture is stirred at a temperature of approximately 25+ C. for 41 hours. After concentrating under reduced pressure (2.7 kPa) at a temperature in the region of 60+ C., the residual oil is taken up 3 times in 30 cm³ of pentane and then reconcentrated under the same conditions. The solid residue obtained is dissolved in 50 cm³ of dichloromethane and washed successively twice with 30 cm³ of a 1N aqueous hydrochloric acid solution, twice with 30 cm³ of water and then twice with 30 cm³ of a saturated aqueous sodium chloride solution. The organic phase is dried over magnesium sulphate and then concentrated under reduced pressure (2.7 kPa) at a temperature of 40+ C. The oil obtained is chromatographed on a silica (0.020–0.045 mm) column eluted with an ethyl acetate/cyclohexane (as a gradient from 1/4 to 1/2 by volume) mixture at a pressure of approximately 1.5★10⁵ Pa. The fractions containing the expected product are combined and concentrated under reduced pressure (2.7 kPa) at a temperature of 40+ C. 1.5 g of 1-{5-[2(S)-hydroxy-2-(2,2,4,4-tetraisopropyl-[1,3,5,2,4] trioxadisilepan-6(R)-yl)ethyl]pyrazin-2-yl}-2-(2,2,4,4-tetraisopropyl-[1,3,5,2,4]trioxadisilepan-6(R)-yl)ethane-1 (R),2(S)-diol are thus obtained in the form of a white foam melting at 87+ C. [¹H N.M.R. spectrum (250 MHz, d6-(CD₃)₂SO, δ in ppm): from 0.80 to 1.30 (mt, 56H, 8 CH(CH₃)₂), 2.78 (dd, J=14 and 9 Hz, 1H, 1H of the 5α CH₂), 3.17 (dd, J=14 and 3.5 Hz, 1H, the other H of the 5α CH₂), 3.53 (broad t, J=9 Hz, 1H, 2β CH), from 3.60 to 3.70 (mt, 4H, 5β CH, 5γ CH, 1H of the 2δ CH₂O and 1H of the 5δ CH₂O), from 4.05 to 4.30 (mt, 3H, 2γ CH, the other H of the 2δ CH₂O and the other H of the 5δ CH₂O), 4.82 (d, J=8 Hz, 1H, OH at 2β), from 4.90 to 5.05 (mt, 2H, 2α CH and 5β OH), 5.46 (d, J=6 Hz, 1H, 2α OH), 8.43 (s, 1H, =CH at 6), 8.66 (s, 1H, =CH at 3);

$$\alpha \frac{20}{D} = -11.1 \oplus \text{K } 0.5 (c = 0.5, \text{dichloromethane})].$$

III-4-[5-(3R,4-Dihydroxy-2S-methoxybutyl)]-pyrazin-2-yl]-3R,4R-dimethoxybutane-1,2-diol can also be prepared in a similar way from 1-[5-(3,4-O-benzylidene-2S,3R,4-trihydroxybutyl)pyrazin-2-yl]butane-3,4-O-benzylidene-1R,2S,3R,4-tetraol.

1-[5-(3,4-O-Benzylidene-2S,3R,4-trihydroxybutyl) pyrazin-2-yl]butane-3,4-O-benzylidene-1R,2S,3R,4-tetraol can be obtained in the following way: 20 mg of D-camphorsulphonic acid are added at a temperature in the region of 20+ C., under argon, to a solution of 2.0 g of deoxyfructosazine in 24 cm³ of dimethylformamide. The white suspension is heated to 50+ C., to give a colourless solution, and then 5 cm³ of benzaldehyde dimethyl acetal are added. The yellow solution is maintained at 50+ C. with stirring for 20 hours, then allowed to cool to room temperature and 60 cm³ of water are added. The mixture is extracted with ethyl acetate (2 times) and washed with 20 cm³ of a saturated sodium hydrogencarbonate solution, then dried over magnesium sulphate and filtered. The organic phases are concentrated under reduced pressure (2.7 kPa) at a temperature of 40° C. to give an orangey oily residue which is chromatographed on a silica (0.040–0.063 mm) column, elution being carried out with a dichloromethane/methanol (95/5 by volume) mixture. The fractions containing the expected product are combined and concentrated under reduced pressure (2.7 kPa) at a temperature of 40° C. to give 1.2 g of pure 1-[5-(3,4-O-benzylidene-2S,3R,4-trihydroxybutyl)pyrazin-2-yl]butane-3,4-O-benzylidene-1R,2S,3R,4-tetraol as a 4/6 diastereoisomeric mixture in the form of a pale yellow oil. The latter gives a white solid product which melts at 70° C. after trituration in diethyl ether [¹H N.M.R. spectrum (400 MHz, d6-(CD₃)₂SO, δ in ppm). The mixture of two diastereoisomers is observed in approximate proportions 40/60: 2.34 (broad dd, J=14 and 10 Hz, 1H, 1H of the 5α CH₂), 3.09 (broad d, J=14 Hz, 1H, the other H of the 5α CH₂), from 3.70 to 4.50 (mts, 8H, 2β CH, 2γ CH, 2δ CH₂O, 5δ CH, 5γ CH and 5δ CH₂O), 4.83 (broad s, 1H, 2α CH), 5.00 (broad d, J=5 Hz, 1H, OH at 2γ), 5.21 (broad d, J=3 Hz, 1H, OH at 5β), 5.69 (mt, 1H, OH at 2α), 5.77, 5.79 and 5.90 (3 s, 2H in all, the 2 OCHO), 8.46 and 8.49 (2 s, 1H in all, =CH at 6), 8.70 (s, 1H, =CH at 3)].

Another series of fractions from the chromatography gives 1-[5-(2,4-O-benzylidine-2S,3R,4-trihydroxybutyl)pyrazin-2-yl]butane-2,4,O-benzylidene-1R,2S,3R,4-tetraol.

EXAMPLE 7

By carrying out the preparation in the same way as in the preceding examples, but from (2,2-diisopropyl-[1,3,2]dioxasilinan-5R-ol-4S-yl)-{5-[(2,2-diisopropyl-[1,3,2]dioxasilinan-5R-ol-4S-yl)methyl]pyrazin-2-yl}methane-1R-ol, 4-[5-(3R-methoxy-2S,4-dihydroxybutyl)pyrazin-2-yl]-2R,4-dimethoxybutane-1,3S-diol is obtained.

(2,2-Diisopropyl-[1,3,2]dioxasilinan-5R-ol-4S-yl)-{5-[(2,2-diisopropyl-[1,3,2]dioxasilinan-5R-ol-4S-yl)methyl]pyrazin-2-yl}methane-1R-ol can be obtained in the following way: 2.1 cm³ of diisopropylsilyl bis(trifluoromethanesulphonate) are added with stirring and under nitrogen to a solution of 1 g of deoxyfructosazine in 27 cm³ of pyridine. The reaction mixture is stirred at a temperature of approximately 25° C. for 71 hours. After concentrating under reduced pressure (2.7 kPa) at a temperature of 50° C., the residual oil is taken up 3 times in 30 cm³ of pentane and then reconcentrated under the same conditions. The residual oil obtained is dissolved in 50 cm³ of dichloromethane and washed successively twice with 30 cm³ of a 1N aqueous hydrochloric acid solution, twice with 30 cm³ of water and then twice with 30 cm³ of a saturated aqueous sodium chloride solution. The organic phase is dried over magnesium sulphate and then concentrated under reduced pressure (2.7 kPa) at a temperature of 40° C. The foam obtained is chromatographed on a silica (0.020–0.045 mm) column eluted with an ethyl acetate/cyclohexane (1/1 by volume) mixture at a pressure of approximately 1.5★10⁵ Pa. The fractions containing the expected product are combined and concentrated under reduced pressure (2.7 kpa) at a temperature of 40° C. The foam obtained is chromatographed on a silica (0.020–0.045 mm) column eluted with an ethyl acetate/cyclohexane (1/1 by volume) mixture at a pressure of approximately 1.5★10⁵ Pa. The fractions containing the expected product are combined and concentrated under reduced pressure (2.7 kPa) at a temperature of 40° C. 60 mg of (2,2-diisopropyl-[1,3,2]dioxasilinan-5R-ol-4S-yl)-{5-[(2,2-diisopropyl-[1,3,2]dioxasilinan-5R-ol-4S-yl)methyl]pyrazin-2-yl}methane-1R-ol are thus isolated in the form of a white foam melting at 54° C. [¹H N.M.R. spectrum (400 MHz, d6-(CD₃)₂SO, δ in ppm): from 0.65 to 1.15 (mt, 28H, 4 CH(CH₃)₂), 2.80 (dd, J=14 and 9 Hz, 1H, 1H of the 5a CH₂), 3.28 (mt, the other H of the 5α CH₂), 3.40 (mt, 1H, 5γ CH), 3.68 (mt, 2H, 1H of the 2d CH₂O and 1H of the 5δ CH₂O), 3.83 (mt, 1H, 2γ CH), from 3.90 to 4.05 (mt, 3H, 2β CH, the other H of the 2δ CH₂O and the other H of the 5δ CH₂O), 4.13 (broad t, J=9.5 Hz, 1H, 5β CH), 4.99 (broad d, J=6.5 Hz, 1H, 2α CH), 5.22 (d, J=6.5 Hz, 1H, OH at 2γ), 5.34 (d, J=6 Hz, 1H, 5γ OH), 5.39 (d, J=6.5 Hz, 1H, OH at 2α), 8.41 (s, 1H, =CH at 6), 8.70 (s, 1H, =CH at 3);

$$\alpha \frac{20}{D} = -38.3 \Phi \text{\ding{58}} 0.8 (c = 0.5, \text{dichloromethane})].$$

EXAMPLE 8

8 cm³ of an 80% aqueous trifluoroacetic acid solution are added to 54 mg of 2-fluoro-1S-[5R-(5-{[5R-(hydroxymethyl)-2,2-dimethyl-[1,3]dioxolan-4S-yl]methyl}pyrazin-2-yl)-2,2-dimethyl-[1,3]dioxolan-4R-yl]ethanol. The reaction mixture is stirred at a temperature of approximately 25° C. for 1.5 hours. After concentrating under reduced pressure (2.7 kPa) at a temperature of 45° C. the residue is taken up in toluene and then reconcentrated under the same conditions (operation repeated once). The brown residual oil is dissolved in 5 cm³ of methanol, filtered through paper and then reconcentrated under the same conditions. The yellow residual oil is taken up in 0.4 cm³ of ethanol and recrystallized. The precipitate obtained is filtered on sintered glass, washed with 0.1 cm³ of ethanol, pulled dry and then dried under reduced pressure (2.7 kPa) at a temperature of 25° C. 31 mg of 4-fluoro-1-[5-(2S,3R,4-trihydroxybutyl)pyrazin-2-yl]butane-1R,2S,3R-triol are thus isolated in the form of a beige crystalline powder melting at 141° C. ¹H N.M.R. spectrum (400 MHz, d6-(CD₃)₂SO, δ in ppm): 2.76 and 3.08 (2 dd, respectively J=14 and 9 Hz and J=14 and 2 Hz, each 1H, 5α CH₂), from 3.30 to 3.45 (mt, 2H, 1H of the 5δ CH₂O and 5γ CH), from 3.50 to 3.70 (mt, 1H, the other H of the 5δ CH₂O), 3.64 (broad d, J=9 Hz, 1H, 2β CH), 3.80 (mt, 1H, 5β CH), from 3.70 to 3.90 (mt, 1H, 2γ CH), from 4.35 to 4.70 (mt, J_{HF}=48 Hz, 2H, 2δ CH₂F), 4.97 (broad s, 1H, 2α CH), 8.44 (broad s, 1H, =CH at 6), 8.67 (broad s, 1H, =CH at 3).

2-Fluoro-1S-[5R-(5-{[5R-(hydroxymethyl)-2,2-dimethyl-[1,3]dioxolan-4S-yl]methyl}pyrazin-2-yl)-2,2-dimethyl-[1,3]dioxolan-4R-yl]ethanol is prepared according to the following method: 0.84 cm³ of a 1.0M solution of tetra(n-butyl)ammonium fluoride in tetrahydrofuran is added dropwise, under argon, to a solution of 210 mg of 2-fluoro-1S-[5R-(5-{[5R-(tertbutyldiphenylsilanyloxymethyl)-2,2-dimethyl-[1,3]-dioxolan-4S-yl]methyl}pyrazin-2-yl)-2,2-dimethyl-[1,3]dioxolan-4R-yl]ethanol in 20 cm³ of tetrahydrofuran. The reaction mixture is stirred at a temperature in the region of 25° C. for 1.5 hours. After concentrating under reduced pressure (2.7 kpa) at a temperature in the region of 40° C., the amber residual oil is chromatographed on a silica (0.040–0.063 mm) column eluted with an ethyl acetate/ cyclohexane 9/1 by volume mixture at a pressure of approximately 1.5★10⁵ Pa. The fractions containing the expected product are combined and concentrated under reduced pressure (2.7 kPa) at a temperature of 40 C. 54 mg of 2-fluoro-1S-[5R-(5-{[5R-(hydroxymethyl)-2,2-dimethyl-[1,3]dioxolan-4S-yl]methyl}pyrazin-2-yl)-2,2-dimethyl-[1,3]dioxolan-4R-yl]ethanol are thus isolated in the form of a yellow oil; (Rf=0.2; silica gel thin layer chromatography; eluent ethyl acetate/cyclohexane 9/1 by volume mixture).

2-Fluoro-1S-[5R-(5-{[5R-(tert-butyldiphenylsilanyloxymethyl)-2,2-dimethyl-[1,3]dioxolan-4S-yl]-methyl}pyrazin-2-yl)-2,2-dimethyl-[1,3]dioxolan-4R-yl]-ethanol is prepared according to the following method: 0.32 cm³ of diethylaminosulphide trifluoride is added dropwise to a solution, cooled to a temperature of −45 C. and under argon, of 1.0 g of 2-(tert-butyldiphenylsilanyloxy)-1R-(5R-{5-[5R-(tert-butyldiphenylsilanyloxymethyl)-2,2-dimethyl-[1,3]dioxolan-4S-yl-methyl]pyrazin-2-yl}-2,2-dimethyl-[1,3]dioxolan-4S-yl)ethanol in 6 cm³ of tetrahydrofuran. The reaction mixture is stirred at a temperature of −45 C. for 2 hours and is then treated dropwise with 0.2 cm³ of methanol. It is subsequently allowed to rise to a temperature of 25 C. and then concentrated under reduced pressure (2.7 kPa) at a temperature of 40 C. The brown residual oil is dissolved in 50 cm³ of dichloromethane and extracted 3 times with 5 cm³ of water. The organic phase is dried over magnesium sulphate and then concentrated under reduced pressure (2.7 kPa) at a temperature of 40 C. The brown residual oil is chromatographed on a silica (0.020–0.045 mm) column eluted with an ethyl acetate/cyclohexane 1/9 by volume mixture at a pressure of approximately 1.5★10⁵ Pa. The fractions containing the expected product are combined and concentrated under reduced pressure (2.7 kPa) at a temperature of 40 C. 0.17 g of 2-fluoro-1S-[5R-(5-{[5R-(tert-butyldiphenylsilanyloxymethyl)-2,2-dimethyl-[1,3]dioxolan-4S-yl]methyl}pyrazin-2-yl)-2,2-dimethyl-[1,3]dioxolan-4R-yl]ethanol is thus obtained in the form of a viscous yellow oil; (Rf=0.3, silica gel thin layer chromatography; eluent ethyl acetate/cyclohexane 1/2.3 by volume mixture).

2-(tert-Butyldiphenylsilanyloxy)-1R-(5R-{5 -[5R-(tert-butyldiphenylsilanyloxymethyl)-2,2-dimethyl-[1,3]dioxolan-4S-ylmethyl]pyrazin-2-yl}-2,2-dimethyl-[1,3]dioxolan-4S-yl)ethanol is prepared according to the following method: 5 cm³ of 2,2-dimethoxypropane and then 0.01 g of para-toluenesulphonic acid are added, with stirring, to a solution of 1 g of 1-[5-(4-(tert-butyldiphenylsilanyloxy)-2S,3R-dihydroxybutyl)pyrazin-2-yl]-4-[tert-butyldiphenylsilanyloxy]butane-1R,2S,3R-triol in 50 cm³ of dimethylformamide. The reaction mixture is stirred at a temperature of 60 C. for 42 hours. After concentrating under reduced pressure (2.7 kPa) at a temperature of 60 C., the residual oil is dissolved in 60 cm³ of dichloromethane and washed twice with 20 cm³ of a 5% aqueous sodium bicarbonate solution and then twice with 20 cm³ of water. The organic phase is dried over magnesium sulphate and then concentrated under reduced pressure (2.7 kPa) at a temperature of 40 C. The oil obtained is chromatographed on a silica (0.020–0.045 mm) column eluted with an ethyl acetate/cyclohexane (1/9 by volume) mixture at a pressure of approximately 1.5★10⁵ Pa. The fractions containing the expected products are combined and concentrated under reduced pressure (2.7 kPa) at a temperature of 40 C. 0.3 g of 2-(tert-butyldiphenylsilanyloxy)-1R-(5R-{5-[5R-(tert-butyldiphenylsilanyloxymethyl)-2,2-dimethyl-[1,3]dioxolan-4S-yl-methyl]pyrazin-2-yl}-2,2-dimethyl-[1,3]dioxolan-4S-yl)ethanol is thus obtained in the form of a viscous yellow oil [¹H N.M.R. spectrum (400 MHz, d6-(CD₃)₂SO, δ in ppm): 0.90 and 1.01, (2 s, each 9H, the 2 C(CH₃)₃), 1.22, 1.35, 1.44 and 1.46 (4 s, each 3H, the 4 CH₃), 3.08 (dd, J=14 and 9 Hz, 1H, 1H of the 5α CH₂), 3.15 (dd, J=14 and 3.5 Hz, 1H, the other H of the 5α CH₂), 3.60 (limit AB, 2H, 2δ CH₂O), 3.71 (dd, J=11 and 5 Hz, 1H, 1H of the 5δ CH₂O), from 3.80 to 3.95 (mt, 2H, the other H of the 5δ CH₂ and 2γ CH), 4.32 (q, J=5 Hz, 1H, 5γ CH), 4.48 (dd, J=7 and 5 Hz, 1H, 2β CH), 4.70 (mt, 1H, 5β CH), 5.14 (d, J=7 Hz, 1H, 2α CH), 5.19 (d, J=5 Hz, 1H, OH at 2γ), from 7.35 to 7.80 (mt, 20H, aromatic H of the 4 phenyls), 8.53 (s, 1H, =CH at 6), 8.68 (s, 1H, =CH at 3), $$\alpha\frac{20}{D} = -32.6 \quad 0.8 (c = 0.5, \text{dichloromethane});$$

(Rf=0.30; silica gel thin layer chromatography; eluent ethyl acetate/cyclohexane 1/4 by volume mixture)].

0.2 g of 4R-(tert-butyldiphenylsilanyloxymethyl)-6R-{5-[5R-(tert-butyldiphenylsilanyloxymethyl)-2,2-dimethyl-[1,3]dioxolan-4S-ylmethyl]pyrazin-2-yl}-2,2-dimethyl-[1,3]dioxan-5S-ol is also isolated from this column in the form of a yellow oil [¹H N.M.R. spectrum (400 MHz, d6-(CD₃)₂SO, δ in ppm): 1.01 and 1.05 (2s, each 9H, the 2 C(CH₃)₃), 1.24, 1.36 and 1.50 (3 s, respectively 3H, 6H and 3H, the 4 CH₃), 3.03 (dd, J=14 and 9 Hz, 1H, 1H of the 5α CH₂), 3.12 (dd, J=14 and 3.5 Hz, 1H, the other H of the 5α CH₂), 3.70 (dd, J=11 and 5.5 Hz, 1H, 1H of the 5δ CH₂O), from 3.75 to 3.95 (mt, 4H, 2γ CH, 2γ CH₂O and the other H of the 5δ CH₂O), 4.03 (mt, 1H, 2β CH), 4.32 (mt, 1H, 5γ CH), 4.70 (mt, 1H, 5β CH), from 4.95 to 5.05 (mt, 2H, 2α CH and 2β OH), from 7.35 to 7.55 and from 7.60 to 7.80 (2 mts, respectively 12H and 8H, aromatic H of the 4 phenyls); 8.46 (s, 1H, =CH at 6), 8.53 (s, 1H, =CH at 3);

$$\alpha\frac{20}{D} = -47.5 \quad 1.5 (c = 0.5, \text{dichloromethane});$$

(Rf=0.24; silica gel thin layer chromatography; eluent ethyl acetate/cyclohexane (1/4 by volume) mixture).

1-[5-(4-(tert-Butyldiphenylsilanyloxy)-2S,3R-dihydroxybutyl)pyrazin-2-yl]-4-[tert-butyldiphenylsilanyloxy]butane-1R,2S,3R-triol is prepared according to the following method: 4.3 cm³ of tert-butyldiphenylchlorosilane are added, with stirring, to a solution of 2 g of deoxyfructosazine in 55 cm³ of pyridine. The reaction mixture is stirred at a temperature of approximately 25 C. for 68 hours, 0.5 cm³ of terbutyldiphenylchlorosilane is then added and stirring is continued for 8 days. After concentrating under reduced pressure (2.7 kPa) at a temperature of 60 C., the residual oil is dissolved in 100 cm³ of dichloromethane and washed 3 times with 30 cm³ of water. The organic phase is dried over magnesium sulphate and then concentrated under reduced pressure (2.7 kPa) at a temperature of 4 The oil obtained is chromatographed on a silica (0.020–0.045 mm) column eluted with a methanol/dichloromethane (1/49 by volume) mixture at a pressure of approximately 1.5★10⁵ Pa. The fractions containing the expected product are combined and concentrated under reduced pressure (2.7 kPa) at a temperature of 40 C. 4 g of 1-[5-(4 -(tert)-butyldiphenylsilanyloxy)-2(S),3(R)-dihydroxybutyl)pyrazin-2-yl]-4-[tert-butyldiphenylsilanyloxy]butane-1(R),2(S),3(R)-triol are thus obtained in the form of a yellow foam (Rf=0.13; silica gel thin layer chromatography; eluent methanol/dichloromethane (1/19 by volume) mixture).

The compounds of formula (I) exhibit advantageous pharmacological properties. They are of hypoglycaemic type.

The hypoglycaemic activity of the compounds of formula (I) was determined with respect to the hyperglycaemic response to the oral administration of glucose in the normoglycaemic mouse, according to the following protocol: Swiss albino mice weighing between 22 and 26 g are left without nourishment for 2 hours. At the end of this period, the glycaemia is measured and, immediately after, a dose of glucose (2 g/kg) is administered orally. 30 minutes later, the glycaemia is once again measured. The mice which respond by a hyperglycaemia greater than 170 mg/dl are selected and used to detect the hypoglycaemic activity of the compounds according to the invention.

The mice thus chosen are divided into groups of at least 10 animals. Separate groups receive a solution of 3 to 50 mg/kg of the test product in a vehicle, such as water or a mixture of methylcellulose/tween and water, or vehicle once daily by gastric intubation. The treatment lasts 4 days. On the 4th day, after the final treatment, the animals receive a dose of glucose (2 g/kg) and the glycaemia is measured 20 to 40 minutes later. The percentage of inhibition of the hyperglycaemic response to the administration of glucose is calculated with respect to the response measured in the group treated with the vehicle.

In this test, the compounds according to the invention exhibit a percentage of inhibition of glycaemia of greater than or equal to 10%.

The compounds of general formula (I) according to the invention exhibit a low toxicity. Their $LD_{50}$ is greater than 2000 mg/kg via the oral route in the mouse.

In human therapeutics, these products are useful in the prevention and treatment of diabetes and in particular type II diabetes (NID diabetes), obese diabetes, diabetes at the age of about fifty, metaplethoric diabetes, diabetes affecting the elderly and mild diabetes. They can be used as a supplement to insulin therapy in insulin-dependent diabetes where they make it possible to gradually reduce the dose of insulin, unstable diabetes, insulin-resistant diabetes, and as a supplement to hypoglycaemic sulphamides when these do not provide a sufficient decrease in glycaemia. These products can also be used in complications of diabetes, such as hyperlipaemias, lipid metabolism disorders, dyslipaemias and obesity. They are also useful in the prevention and treatment of lesions of atherosclerosis and their complications (coronopathies, myocardial infarction, cardiomyopathies, progression of these three complications into left ventricular insufficiency, various arteriopathies, arterites of the lower limbs with claudication and progression into ulcers and gangrene, cerebral vascular insufficiency and its complications and sexual impotence of vascular origin), diabetic retinopathy and all its manifestations (increase in capillary permeability, capillary thrombosis and dilation, microaneurysms, arteriovenous shunt, venous dilation, punctiform and macular haemorrhages, exudates, macular oedemas, manifestations of proliferative retinopathy: neovessels, proliferative retinitis scars, haemorrhages of the vitreous body, retinal detachment), diabetic cataract, diabetic neuropathy in its various forms (peripheral polyneuropathies and its manifestations, such as paraesthesias, hyperaesthesias and pain, mononeuropathies, radiculopathies, autonomous neuropathies, diabetic amyotrophies), manifestations of diabetic foot (ulcers of the lower extremities and of the foot), diabetic nephropathy in its two diffuse and nodular forms, atheromatosis (rise in HDL lipoproteins promoting the elimination of cholesterol from the atheroma plaques, decrease in the LDL lipoproteins, decrease in the LDL/HDL ratio, inhibition of oxidation of the LDLs, decrease in plaque adhesiveness), hyperlipaemias and dyslipaemias (hypercholesterolaemias, hypertriglyceridaemias, ormalization of the fatty acid level, normalization of uricaemia, normalization of the A and B apoproteins), cataracts, arterial hypertension and its consequences.

The medicaments according to the invention are composed of a compound according to the invention or a combination of these products, in the pure state or in the form of a composition in which it is combined with any other pharmaceutically compatible product, which can be inert or physiologically active. The medicaments according to the invention can be employed orally, parenterally, rectally or topically.

As solid compositions for oral administration, there can be used tablets, pills, powders (gelatin capsules, cachets) or granules. In these compositions, the active principle according to the invention is mixed with one or more inert diluents, such as starch, cellulose, sucrose, lactose or silica, under an argon stream. These compositions can also comprise substances other than the diluents, for example one or more lubricants such as magnesium stearate or talc, a colorant, a coating (dragees) or a glaze.

As liquid compositions for oral administration, there can be used pharmaceutically acceptable solutions, suspensions, emulsions, syrups and elixirs containing inert diluents, such as water, ethanol, glycerol, vegetable oils or liquid paraffin. These compositions can comprise substances other than the diluents, for example wetting, sweetening, thickening, flavouring or stabilizing products.

The sterile compositions for parenteral administration can preferably be solutions in aqueous or nonaqueous form, suspensions or emulsions. As solvent or vehicle, there can be employed water, propylene glycol, a polyethylene glycol, vegetable oils, in particular olive oil, injectable organic esters, for example ethyl oleate, or other suitable organic solvents. These compositions can also contain adjuvants, in particular wetting, isotonizing, emulsifying, dispersing and stabilizing agents. Sterilization can be performed in several ways, for example by aseptizing filtration, by incorporating sterilizing agents into the composition, by irradiation or by heating. They can also be prepared in the form of sterile solid compositions which can be dissolved at the time of use in sterile water or any other injectable sterile medium.

The compositions for rectal administration are suppositories or rectal capsules which contain, in addition to the active product, excipients such as cocoa butter, semisynthetic glycerides or polyethylene glycols.

The compositions for topical administration can be, for example, creams, lotions, collyria, collutoria, nose drops or aerosols.

The doses depend on the desired effect, the duration of treatment and the administration route used; they are generally between 150 mg and 600 mg per day via the oral route for an adult with unit doses ranging from 50 mg to 200 mg of active substance.

In general, the doctor will determine the appropriate dosage according to the age, weight and all the other factors specific to the subject to be treated.

The following examples illustrate compositions according to the invention:

EXAMPLE A

Hard gelatin capsules, with doses of 50 mg of active product, having the following composition are prepared according to the usual technique:

| | |
|---|---|
| Active product | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE B

Tablets, with doses of 50 mg of active product, having the following composition are prepared according to the usual technique:

| | |
|---|---|
| Active product | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Hydroxymethylcellulose, glycerol, titanium oxide (72/3.5/24.5) mixture qs for 1 finished film-coated tablet containing | 245 mg |

EXAMPLE C

An injectable solution containing 50 mg of active product having the following composition is prepared:

| | |
|---|---|
| Active product | 50 mg |
| Benzoic acid | 80 mg |
| Benzyl alcohol | 0.06 ml |
| Sodium benzoate | 80 mg |
| Ethanol at 95% | 0.4 ml |
| Sodium hydroxide | 24 mg |
| Propylene glycol | 1.6 ml |
| Water | qs for 4 ml |

The invention also relates to the use of the compounds of general formula (I) in the preparation of pharmaceutical compositions of use in the treatment or prevention of diabetes and complications of diabetes.

What is claimed is:

1. A pharmaceutical composition comprising a compound of formula:

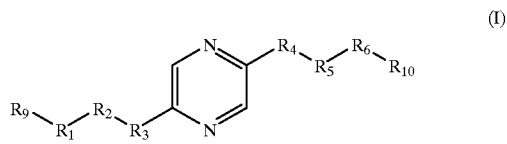

in which either (A) $R_9$ and $R_{10}$ are identical and each is a —$CH_2OH$ radical and either a) $R_3$ is a methylene radical, $R_4$ is a —CHOH— radical and one of the $R_1$, $R_2$, $R_5$ and $R_6$ radicals is a carbonyl, methylene, —CHF—, —CH($NHR_7$)— or —CH($OR_8$) radical and each of the others is a —CHOH— radical, or b) $R_2$ and $R_5$ each is a —CHOH— radical, $R_3$ is a methylene radical and $R_1$, $R_4$ and $R_6$ are identical and each is a carbonyl, methylene, —CHF—, —CH($NHR_7$)— or —CH($OR_8$) radical, or c) $R_1$, and $R_6$ each is a —CHOH— radical, $R_3$ is a methylene radical and $R_2$, $R_4$ and $R_5$ are identical and each is a carbonyl, methylene, —CHF—, —CH($NHR_7$)— or —CH($OR_8$) radical, or d) $R_1$, $R_4$, $R_5$ and $R_6$ each is a —CHOH— radical and —$R_2$—$R_3$— is a —CH=CH— radical, or (B) $R_1$, $R_2$, $R_4$, $R_5$ and $R_6$ each is a —CHOH— radical, $R_3$ is a methylene radical, $R_9$ is a —$CH_2F$ or —$CH_2OH$ radical, $R_{10}$ is a —$CH_2F$ or —$CH_2OH$ radical, $R_9$ and $R_{10}$ not both being a —$CH_2OH$ radical, $R_7$ is a hydrogen atom or an alkyl, —CO—alk, —CO—Ar or —CO—Het radical, $R_8$ is an alkyl, —alk—COOH or —alk—OH radical, alk being an alkyl radical, Ar is a phenyl radical or a phenyl radical substituted by one or more substituents selected from a halogen atom and alkyl, alkoxy, alkoxycarbonyl, amino, monoalkylamino and dialkylamino radicals, Het is a saturated or unsaturated, mono-, di- or tricyclic heterocycle comprising 1 to 9 carbon atoms and one or more heteroatoms selected from oxygen, sulphur and nitrogen, the alkyl and alkoxy radicals comprising 1 to 6 carbon atoms in a straight or branched chain, or its stereoisomers or, for a compound in which —$R_2$—$R_3$— represents a —CH=CH— radical, its cis or trans forms, or its salts with a pharmaceutically acceptable inorganic or organic acid.

2. A pharmaceutical composition according to claim 1, wherein Het is a heterocycle selected from the 2-, 3- and 4-pyridyl, imidazolyl, thiazolyl and oxazolyl rings.

3. A pharmaceutical composition according to claim 1, wherein said compound is selected from the group consisting of:

1-[5-(3R,4-Dihydroxy-2-oxobutyl)pyrazin-2-yl]butane-1R, 2S,3R,4-tetraol,

1-[5-(3S,4-Dihydroxybutyl)pyrazin-2-yl]butane-1R,2S,3R, 4-tetraol,

1-[5-(2S-Fluoro-3R,4-dihydroxybutyl)pyrazin-2-yl]butane-1R,2S,3R,4-tetraol,

1-[5-(2R-Fluoro-3R,4-dihydroxybutyl)pyrazin-2-yl]butane-1R,2S,3R,4-tetraol,

1-[5-(2S-Amino-3S,4-dihydroxybutyl)pyrazin-2-yl]butane-1R,2S,3R,4-tetraol,

1-[5-(2R-Amino-3S,4-dihydroxybutyl)pyrazin-2-yl]butane-1R,2S,3R,4-tetraol,

1-[5-(2S-(N-Methyl)amino-3S,4-dihydroxybutyl)pyrazin-2-yl]butane-1R,2S,3R,4-tetraol, 1-[5-(2R-(N-Methyl)amino-3S,4-dihydroxybutyl)pyrazin-2-yl]butane-1R,2S,3R,4-tetraol,
1-[5-(2S-(N-Ethyl)amino-3S,4-dihydroxybutyl)pyrazin-2-yl]butane-1R,2S,3R,4-tetraol,
1-[5-(2R-(N-Ethyl)amino-3S,4-dihydroxybutyl)pyrazin-2-yl]butane-1R,2S,3R,4-tetraol,
1-[5-(2S-(N-n-Butyl)amino-3S,4-dihydroxybutyl)pyrazin-2-yl]butane-1R,2S,3R,4-tetraol,
1-[5-(2R-(N-n-Butyl)amino-3S,4-dihydroxybutyl)pyrazin-2-yl]butane-1R,2S,3R,4-tetraol,
1-[5-(2S-(N-Benzyl)amino-3S,4-dihydroxybutyl)pyrazin-2-yl]butane-1R,2S,3R,4-tetraol,
1-[5-(2R-(N-Benzyl)amino-3S,4-dihydroxybutyl)pyrazin-2-yl]butane-1R,2S,3R,4-tetraol,
1-[5-(2S-(N-Acetyl)amino-3S,4-dihydroxybutyl)pyrazin-2-yl]butane-1R,2S,3R,4-tetraol,
1-[5-(2R-(N-Acetyl)amino-3S,4-dihydroxybutyl)pyrazin-2-yl]butane-1R,2S,3R,4-tetraol,
1-[5-(2S-(N-Butanoyl)amino-3S,4-dihydroxybutyl)pyrazin-2-yl]butane-1R,2S,3R,4-tetraol,
1-[5-(2R-(N-Butanoyl)amino-3S,4-dihydroxybutyl)pyrazin-2-yl]butane-1R,2S,3R,4-tetraol,
1-[5-(2S-(N-Benzoyl)amino-3S,4-dihydroxybutyl)pyrazin-2-yl]butane-1R,2S,3R,4-tetraol,
1-[5-(2R-(N-Benzoyl)amino-3S,4-dihydroxybutyl)pyrazin-2-yl]butane-1R,2S,3R,4-tetraol,
1-[5-(2S-Methoxy-3R,4-dihydroxybutyl)pyrazin-2-yl]butane-1R,2S,3R,4-tetraol,
1-[5-(2R-Methoxy-3R,4-dihydroxybutyl)pyrazin-2-yl]butane-1R,2S,3R,4-tetraol,
1-[5-(2S-Ethoxy-3R,4-dihydroxybutyl)pyrazin-2-yl]butane-1R,2S,3R,4-tetraol,
1-[5-(2R-Ethoxy-3R,4-dihydroxybutyl)pyrazin-2-yl]butane-1R,2S,3R,4-tetraol,
1-[5-(2S-n-Butoxy-3S,4-dihydroxybutyl)pyrazin-2-yl]butane-1R,2S,3R,4-tetraol,
1-[5-(2R-n-Butoxy-3S,4-dihydroxybutyl)pyrazin-2-yl]butane-1R,2S,3R,4-tetraol,
1-[5-(2S-(2-Hydroxyethyl)oxy-3R,4-dihydroxybutyl)pyrazin-2-yl]butane-1R,2S,3R,4-tetraol,
1-[5-(2R-(2-Hydroxyethyl)oxy-3R,4-dihydroxybutyl)pyrazin-2-yl]butane-1R,2S,3R,4-tetraol,
1-[5-(2S-(3-Hydroxy-n-propyl)oxy-3R,4-dihydroxybutyl)pyrazin-2-yl]butane-1R,2S,3R,4-tetraol,
1-[5-(2R-(3-Hydroxy-n-propyl)oxy-3R,4-dihydroxybutyl)pyrazin-2-yl]butane-1R,2S,3R,4-tetraol,
1-[5-(2S-(Carboxymethyl)oxy-3R,4-dihydroxybutyl)pyrazin-2-yl]butane-1R,2S,3R,4-tetraol,
1-[5-(2R-(Carboxymethyl)oxy-3R,4-dihydroxybutyl)pyrazin-2-yl]butane-1R,2S,3R,4-tetraol,
1-[5-(2S-(3-Carboxy-n-propyl)oxy-3R,4-dihydroxybutyl)pyrazin-2-yl]butane-1R,2S,3R,4-tetraol,
1-[5-(2R-(3-Carboxy-n-propyl)oxy-3R,4-dihydroxybutyl)pyrazin-2-yl]butane-1R,2S,3R,4-tetraol,
1-[5-(2S,4-Dihydroxy-3-oxobutyl)pyrazin-2-yl]butane-1R,2S,3R,4-tetraol,
1-[5-(2S,4-Dihydroxybutyl)pyrazin-2-yl]butane-1R,2S,3R,4-tetraol,
1-[5-(3R-Fluoro-2S,4-dihydroxybutyl)pyrazin-2-yl]butane-1R,2S,3R,4-tetraol,
1-[5-(3S-Fluoro-2S,4-dihydroxybutyl)pyrazin-2-yl]butane-1R,2S,3R,4-tetraol,
1-[5-(3R-Amino-2R,4-dihydroxybutyl)pyrazin-2-yl]butane-1R,2S,3R,4-tetraol,
1-[5-(3S-Amino-2R,4-dihydroxybutyl)pyrazin-2-yl]butane-1R,2S,3R,4-tetraol,
1-[5-(3R-(N-Methyl)amino-2R,4-dihydroxybutyl)pyrazin-2-yl]butane-1R,2S,3R,4-tetraol,
1-[5-(3S-(N-Methyl)amino-2R,4-dihydroxybutyl)pyrazin-2-yl]butane-1R,2S,3R,4-tetraol,
1-[5-(3R-(N-Ethyl)amino-2R,4-dihydroxybutyl)pyrazin-2-yl]butane-1R,2S,3R,4-tetraol,
1-[5-(3S-(N-Ethyl)amino-2R,4-dihydroxybutyl)pyrazin-2-yl]butane-1R,2S,3R,4-tetraol,
1-[5-(3R-(N-n-Butyl)amino-2R,4-dihydroxybutyl)pyrazin-2-yl]butane-1R,2S,3R,4-tetraol,
1-[5-(3S-(N-n-Butyl)amino-2R,4-dihydroxybutyl)pyrazin-2-yl]butane-1R,2S,3R,4-tetraol,
1-[5-(3R-(N-Benzyl)amino-2R,4-dihydroxybutyl)pyrazin-2-yl]butane-1R,2S,3R,4-tetraol,
1-[5-(3S-(N-Benzyl)amino-2R,4-dihydroxybutyl)pyrazin-2-yl]butane-1R,2S,3R,4-tetraol,
1-[5-(3R-(N-Acetyl)amino-2R,4-dihydroxybutyl)pyrazin-2-yl]butane-1R,2S,3R,4-tetraol,
1-[5-(3S-(N-Acetyl)amino-2R,4-dihydroxybutyl)pyrazin-2-yl]butane-1R,2S,3R,4-tetraol,
1-[5-(3R-(N-Butanoyl)amino-2R,4-dihydroxybutyl)pyrazin-2-yl]butane-1R,2S,3R,4-tetraol,
1-[5-(3S-(N-Butanoyl)amino-2R,4-dihydroxybutyl)pyrazin-2-yl]butane-1R,2S,3R,4-tetraol,
1-[5-(3R-(N-Benzoyl)amino-2R,4-dihydroxybutyl)pyrazin-2-yl]butane-1R,2S,3R,4-tetraol,
1-[5-(3S-(N-Benzoyl)amino-2R,4-dihydroxybutyl)pyrazin-2-yl]butane-1R,2S,3R,4-tetraol,
1-[5-(3R-Methoxy-2S,4-dihydroxybutyl)pyrazin-2-yl]butane-1R,2S,3R,4-tetraol,
1-[5-(3S-Methoxy-2S,4-dihydroxybutyl)pyrazin-2-yl]butane-1R,2S,3R,4-tetraol,
1-[5-(3R-Ethoxy-2S, 4-dihydroxybutyl)pyrazin-2-yl]butane-1R,2S,3R,4-tetraol,
1-[5-(3S-Ethoxy-2S,4-dihydroxybutyl)pyrazin-2-yl]butane-1R,2S,3R,4-tetraol,
1-[5-(3R-n-Butoxy-2S,4-dihydroxybutyl)pyrazin-2-yl]butane-1R,2S,3R,4-tetraol,
1-[5-(3S-n-Butoxy-2S,4-dihydroxybutyl)pyrazin-2-yl]butane-1R,2S,3R,4-tetraol,
1-[5-(3R-(2-Hydroxyethyl)oxy-2S,4-dihydroxybutyl)pyrazin-2-yl]butane-1R,2S,3R,4-tetraol,
1-[5-(3S-(2-Hydroxyethyl)oxy-2S,4-dihydroxybutyl)pyrazin-2-yl]butane-1R,2S,3R,4-tetraol,
1-[5-(3R-(3-Hydroxy-n-propyl)oxy-2S,4-dihydroxybutyl)pyrazin-2-yl]butane-1R,2S,3R,4-tetraol,
1-[5-(3S-(3-Hydroxy-n-propyl)oxy-2S,4-dihydroxybutyl)pyrazin-2-yl]butane-1R,2S,3R,4-tetraol,
1-[5-(3R-(Carboxymethyl)oxy-2S,4-dihydroxybutyl)pyrazin-2-yl]butane-1R,2S,3R,4-tetraol,
1-(5-(3S-(Carboxymethyl)oxy-2S,4-dihydroxybutyl)pyrazin-2-yl]butane-1R,2S,3R,4-tetraol,
1-[5-(3R-(3-Carboxy-n-propyl)oxy-2S,4-dihydroxybutyl)pyrazin-2-yl]butane-1R,2S,3R,4-tetraol,
1-[5-(3S-(3-Carboxy-n-propyl)oxy-2S,4-dihydroxybutyl)pyrazin-2-yl]butane-1R,2S,3R,4-tetraol,
4-[5-(2S,3R,4-Trihydroxybutyl)pyrazin-2-yl]-1,3S,4R-trihydroxybutane-2-one,
1-[5-(2S,3R,4-Trihydroxybutyl)pyrazin-2-yl]butane-1R,2R,4-triol,
1-[5-(2S,3R,4-Trihydroxybutyl)pyrazin-2-yl]-3R-fluorobutane-1R,2S,4-triol,
1-[5-(2S,3R,4-Trihydroxybutyl)pyrazin-2-yl]-3S-fluorobutane-1R,2S,4-triol,
1-[5-(2S,3R,4-Trihydroxybutyl)pyrazin-2-yl]-3R-aminobutane-1R,2R,4-triol,
1-[5-(2S,3R,4-Trihydroxybutyl)pyrazin-2-yl]-3S-aminobutane-1R,2R,4-triol,
1-[5-(2S,3R,4-Trihydroxybutyl)pyrazin-2-yl]-3R-(N-methyl)aminobutane-1R,2R,4-triol, 1-[5-(2S,3R,4-Trihydroxybutyl)pyrazin-2-yl]-3S-(N-methyl)aminobutane-1R,2R,4-triol,
1-[5-(2S,3R,4-Trihydroxybutyl)pyrazin-2-yl]-3R-(N-ethyl)aminobutane-1R,2R,4-triol,
1-[5-(2S,3R,4-Trihydroxybutyl)pyrazin-2-yl]-3S-(N-ethyl)aminobutane-1R,2R,4-triol,
1-[5-(2S,3R,4-Trihydroxybutyl)pyrazin-2-yl]-3R-(N-n-butyl)aminobutane-1R,2R,4-triol,
1-[5-(2S,3R,4-Trihydroxybutyl)pyrazin-2-yl]-3S-(N-n-butyl)aminobutane-1R,2R,4-triol,
1-[5-(2S,3R,4-Trihydroxybutyl)pyrazin-2-yl]-3R-(N-benzyl)aminobutane-1R,2R,4-triol,
1-[5-(2S,3R,4-Trihydroxybutyl)pyrazin-2-yl]-3S-(N-benzyl)aminobutane-1R,2R,4-triol,
1-[5-(2S,3R,4-Trihydroxybutyl)pyrazin-2-yl]-3R-(N-acetyl)aminobutane-1R,2R,4-triol,
1-[5-(2S,3R,4-Trihydroxybutyl)pyrazin-2-yl]-3S-(N-acetyl)aminobutane-1R,2R,4-triol,
1-[5-(2S,3R,4-Trihydroxybutyl)pyrazin-2-yl]-3R-(N-butanoyl)aminobutane-1R,2R,4-triol,
1-[5-(2S,3R,4-Trihydroxybutyl)pyrazin-2-yl]-3S-(N-butanoyl)aminobutane-1R,2R,4-triol,
1-[5-(2S,3R,4-Trihydroxybutyl)pyrazin-2-yl]-3R-(N-benzoyl)aminobutane-1R,2R,4-triol,
1-[5-(2S,3R,4-Trihydroxybutyl)pyrazin-2-yl]-3S-(N-benzoyl)aminobutane-1R,2R,4-triol,
1-[5-(2S,3R,4-Trihydroxybutyl)pyrazin-2-yl]-3R-methoxybutane-1R,2S,4-triol,
1-[5-(2S,3R,4-Trihydroxybutyl)pyrazin-2-yl]-3S-methoxybutane-1R,2S,4-triol,
1-[5-(2S,3R,4-Trihydroxybutyl)pyrazin-2-yl]-3R-ethoxybutane-1R,2S,4-triol,
1-[5-(2S,3R,4-Trihydroxybutyl)pyrazin-2-yl]-3S-ethoxybutane-1R,2S,4-triol,
1-[5-(2S,3R,4-Trihydroxybutyl)pyrazin-2-yl]-3R-n-butoxybutane-1R,2S,4-triol,
1-[5-(2S,3R,4-Trihydroxybutyl)pyrazin-2-yl]-3S-n-butoxybutane-1R,2S,4-triol,
1-[5-(2S,3R,4-Trihydroxybutyl)pyrazin-2-yl]-3R-[(2-hydroxyethyl)oxy]butane-1R,2S,4-triol,
1-[5-(2S,3R,4-Trihydroxybutyl)pyrazin-2-yl]-3S-[(2-hydroxyethyl)oxy]butane-1R,2S,4-triol,
1-[5-(2S,3R,4-Trihydroxybutyl)pyrazin-2-yl]-3R-[(3-hydroxy-n-propyl)oxy]butane-1R,2S,4-triol,
1-[5-(2S,3R,4-Trihydroxybutyl)pyrazin-2-yl]-3S-[(3-hydroxy-n-propyl)oxy]butane-1R,2S,4-triol,
1-[5-(2S,3R,4-Trihydroxybutyl)pyrazin-2-yl]-3R-[(carboxymethyl)oxy]butane-1R,2S,4-triol,
1-[5-(2S,3R,4-Trihydroxybutyl)pyrazin-2-yl]-3S-[(carboxymethyl)oxy]butane-1R,2S,4-triol,
1-[5-(2S,3R,4-Trihydroxybutyl)pyrazin-2-yl]-3R-[(3-carboxy-n-propyl)oxy]butane-1R,2S,4-triol,
1-[5-(2S,3R,4-Trihydroxybutyl)pyrazin-2-yl]-3S-[(3-carboxy-n-propyl)oxy]butane-1R,2S,4-triol,
1-[5-(2S,3R,4-Trihydroxybutyl)pyrazin-2-yl]-1R,3R,4-trihydroxybutane-2-one,
1-[5-(2S,3R,4-Trihydroxybutyl)pyrazin-2-yl]butane-1R,3R,4-triol,
1-[5-(2S,3R,4-Trihydroxybutyl)pyrazin-2-yl]-2R-fluorobutane-1R,3R,4-triol,
1-[5-(2S,3R,4-Trihydroxybutyl)pyrazin-2-yl]-2S-fluorobutane-1R,3R,4-triol,
1-[5-(2S,3R,4-Trihydroxybutyl)pyrazin-2-yl]-2R-aminobutane-1S,3S,4-triol,
1-[5-(2S,3R,4-Trihydroxybutyl)pyrazin-2-yl]-2S-aminobutane-1S,3S,4-triol,
1-[5-(2S,3R,4-Trihydroxybutyl)pyrazin-2-yl]-2R-(N-methyl)aminobutane-1S,3S,4-triol,
1-[5-(2S,3R,4-Trihydroxybutyl)pyrazin-2-yl]-2S-(N-methyl)aminobutane-1S,3S,4-triol,
1-[5-(2S,3R,4-Trihydroxybutyl)pyrazin-2-yl]-2R-(N-ethyl)aminobutane-1S,3S,4-triol,
1-[5-(2S,3R,4-Trihydroxybutyl)pyrazin-2-yl]-2S-(N-ethyl)aminobutane-1S,3S,4-triol,
1-[5-(2S,3R,4-Trihydroxybutyl)pyrazin-2-yl]-2R-(N-n-butyl)aminobutane-1S,3S,4-triol,
1-[5-(2S,3R,4-Trihydroxybutyl)pyrazin-2-yl]-2S-(N-n-butyl)aminobutane-1S,3S,4-triol,
1-[5-(2S,3R,4-Trihydroxybutyl)pyrazin-2-yl]-2R-(N-benzyl)aminbutane-1S,3S,4-triol,
1-[5-(2S,3R,4-Trihydroxybutyl)pyrazin-2-yl]-2S-(N-benzyl)aminobutane-1S,3S,4-triol,
1-[5-(2S,3R,4-Trihydroxybutyl)pyrazin-2-yl]-2R-(N-acetyl)aminobutane-1S,3S,4-triol,
1-[5-(2S,3R,4-Trihydroxybutyl)pyrazin-2-yl]-2S-(N-acetyl)aminobutane-1S,3S,4-triol,
1-[5-(2S,3R,4-Trihydroxybutyl)pyrazin-2-yl]-2R-(N-butanoyl)aminobutane-1S,3S,4-triol,
1-[5-(2S,3R,4-Trihydroxybutyl)pyrazin-2-yl]-2S-(N-butanoyl)aminobutane-1S,3S,4-triol,
1-[5-(2S,3R,4-Trihydroxybutyl)pyrazin-2-yl]-2R-(N-benzoyl)aminobutane-1S,3S,4-triol,
1-[5-(2S,3R,4-Trihydroxybutyl)pyrazin-2-yl]-2S-(N-benzoyl)aminobutane-1S,3S,4-triol,
1-[5-(2S,3R,4-Trihydroxybutyl)pyrazin-2-yl]-2R-methoxybutane-1R,3R,4-triol,
1-[5-(2S,3R,4-Trihydroxybutyl)pyrazin-2-yl]-2S-methoxybutane-1R,3R,4-triol,
1-[5-(2S,3R,4-Trihydroxybutyl)pyrazin-2-yl]-2R-ethoxybutane-1R,3R,4-triol,
1-[5-(2S,3R,4-Trihydroxybutyl)pyrazin-2-yl]-2S-ethoxybutane-1R,3R,4-triol,
1-[5-(2S,3R,4-Trihydroxybutyl)pyrazin-2-yl]-2R-n-butoxybutane-1R,3R,4-triol,
1-[5-(2S,3R,4-Trihydroxybutyl)pyrazin-2-yl]-2S-n-butoxybutane-1R,3R,4-triol,
1-[5-(2S,3R,4-Trihydroxybutyl)pyrazin-2-yl]-2R-[(2-hydroxyethyl)oxy]butane-1R,3R,4-triol,
1-[5-(2S,3R,4-Trihydroxybutyl)pyrazin-2-yl]-2S-[(2-hydroxyethyl)oxy]butane-1R,3R,4-triol,
1-[5-(2S,3R,4-Trihydroxybutyl)pyrazin-2-yl]-2R-[(3-hydroxy-n-propyl)oxy]butane-1R,3R,4-triol,
1-[5-(2S,3R,4-Trihydroxybutyl)pyrazin-2-yl]-2S-[(3-hydroxy-n-propyl)oxy]butane-1R,3R,4-triol,
1-[5-(2S,3R,4-Trihydroxybutyl)pyrazin-2-yl]-2R-[(carboxymethyl)oxy]butane-1R,3R,4-triol,
1-[5-(2S,3R,4-Trihydroxybutyl)pyrazin-2-yl]-2S-[(carboxymethyl)oxy]butane-1R,3R,4-triol,
1-[5-(2S,3R,4-Trihydroxybutyl)pyrazin-2-yl]-2R-[(3-carboxy-n-propyl)oxy]butane-1R,3R,4-triol,
1-[5-(2S,3R,4-Trihydroxybutyl)pyrazin-2-yl]-2S-[(3-carboxy-n-propyl)oxy]butane-1R,3R,4-triol,
1-[5-(2S,4-Dihydroxy-3-oxobutyl)pyrazin-2-yl]-2S,4-dihydroxybutane-1,3-diane,
4-[5-(2S,4-Dihydroxybutyl)pyrazin-2-yl]butane-1,3S-diol,
4-[5-(3R-Fluoro-2S,4-dihydroxybutyl)pyrazin-2-yl]-2R,4R-difluorobutane-1,3S-diol,
4-[5-(3S-Fluoro-2S,4-dihydroxybutyl)pyrazin-2-yl]-2S,4S-difluorobutane-1,3S-diol,
1-[5-(3R-Amino-2S,4-dihydroxybutyl)pyrazin-2-yl]-2R,4R-diaminobutane-1,3S-diol,
1-[5-(3S-Amino-2S,4-dihydroxybutyl)pyrazin-2-yl]-2S,4S-diaminobutane-1,3S-diol,
1-[5-(3R-(N-Methyl)amino-2S,4-dihydroxybutyl)pyrazin-2-yl]-2R,4R-di[(N-methyl)amino]butane-1,3S-diol, 1-[5-(3S-(N-Methyl)amino-2S,4-dihydroxybutyl)pyrazin-2-yl]-2S,4S-di[(N-methyl)amino]butane-1,3S-diol,
1-[5-(3R-(N-Ethyl)amino-2S,4-dihydroxybutyl)pyrazin-2-yl]-2R,4R-di[(N-ethyl)amino]butane-1,3S-diol,
1-[5-(3S-(N-Ethyl)amino-2S,4-dihydroxybutyl)pyrazin-2-yl]-2S,4S-di[(N-ethyl)amino]butane-1,3S-diol,
1-[5-(3R-(N-n-Butyl)amino-2S,4-dihydroxybutyl)pyrazin-2-yl]-2R,4R-di[(N-n-butyl)amino]butane-1,3S-diol,
1-[5-(3S-(N-n-Butyl)amino-2S,4-dihydroxybutyl)pyrazin-2-yl]-2S,4S-di[(N-n-butyl)amino]butane-1,3S-diol,
1-[5-(3R-(N-Benzyl)amino-2S,4-dihydroxybutyl)pyrazin-2-yl]-2R,4R-di[(N-benzyl)amino]butane-1,3S-diol,
1-[5-(3S-(N-Benzyl)amino-2S,4-dihydroxybutyl)pyrazin-2-yl]-2S,4S-di[(N-benzyl)amino]butane-1,3S-diol,
1-[5-(3R-(N-Acetyl)amino-2S,4-dihydroxybutyl)pyrazin-2-yl]-2R,4R-di[(N-acetyl)amino]butane-1,3S-diol,
1-[5-(3S-(N-Acetyl)amino-2S,4-dihydroxybutyl)pyrazin-2-yl]-2S,4S-di[(N-acetyl)amino]butane-1,3S-diol,
1-[5-(3R-(N-Butanoyl)amino-2S,4-dihydroxybutyl)pyrazin-2-yl]-2R,4R-di[(N-butanoyl)amino]butane-1,3S-diol,
1-[5-(3S-(N-Butanoyl)amino-2S,4-dihydroxybutyl)pyrazin-2-yl]-2S,4S-di[(N-butanoyl)amino]butane-1,3S-diol,
1-[5-(3R-(N-Benzoyl)amino-2S,4-dihydroxybutyl)pyrazin-2-yl]-2R,4R-di[(N-benzoyl)amino]butane-1,3S-diol,
1-[5-(3S-(N-Benzoyl)amino-2S,4-dihydroxybutyl)pyrazin-2-yl]-2S,4S-di[(N-benzoyl)amino]butane-1,3S-diol,
1-[5-(3R-Methoxy-2S,4-dihydroxybutyl)pyrazin-2-yl]-2R,4R-dimethoxybutane-1,3S-diol,
1-[5-(3S-Methoxy-2S,4-dihydroxybutyl)pyrazin-2-yl]-2S,4S-dimethoxybutane-1,3S-diol,
1-[5-(3R-Ethoxy-2S,4-dihydroxybutyl)pyrazin-2-yl]-2R,4R-diethoxybutane-1,3S-diol,
1-[5-(3S-Ethoxy-2S,4-dihydroxybutyl)pyrazin-2-yl]-2S,4S-diethoxybutane-1,3S-diol,
1-[5-(3R-n-Butoxy-2S,4-dihydroxybutyl)pyrazin-2-yl]-2R,4R-di-n-butoxybutane-1,3S-diol,
1-[5-(3S-n-Butoxy-2S,4-dihydroxybutyl)pyrazin-2-yl]-2S,4S-di-n-butoxybutane-1,3S-diol,
1-[5-(3R-(2-Hydroxyethyl)oxy-2S,4-dihydroxybutyl)pyrazin-2-yl]-2R,4R-di[(2-hydroxyethyl)oxy]butane-1,3S-diol,
1-[5-(3S-(2-Hydroxyethyl)oxy-2S,4-dihydroxybutyl)pyrazin-2-yl]-2S,4S-di[(2-hydroxyethyl)oxy]butane-1,3S-diol,
1-[5-(3R-(3-Hydroxy-n-propyl)oxy-2S,4-dihydroxybutyl)pyrazin-2-yl]-2R,4R-di[(3-hydroxy-n-propyl)oxy]butane-1,3S-diol,
1-[5-(3S-(3-Hydroxy-n-propyl)oxy-2S,4-dihydroxybutyl)pyrazin-2-yl]-2S,4S-di[(3-hydroxy-n-propyl)oxy]butane-1,3S-diol,
1-[5-(3R-(Carboxymethyl)oxy-2S,4-dihydroxybutyl)pyrazin-2-yl]-2R,4R-di[(carboxymethyl)oxy]butane-1,3S-diol,
1-[5-(3S-(Carboxymethyl)oxy-2S,4-dihydroxybutyl)pyrazin-2-yl]-2S,4S-di[(carboxymethyl)oxy]butane-1,3S-diol,
1-[5-(3R-(3-Carboxy-n-propyl)oxy-2S,4-dihydroxybutyl)pyrazin-2-yl]-2R,4R-di[(3-carboxy-n-propyl)oxy]butane-1,3S-diol,
1-[5-(3S-(3-Carboxy-n-propyl)oxy-2S,4-dihydroxybutyl)pyrazin-2-yl]-2S,4S-di[(3-carboxy-n-propyl)oxy]butane-1,3S-diol,
1-[5-(3R,4-Dihydroxy-2-oxobutyl)pyrazin-2-yl]-3R,4-dihydroxybutane-1,2-dione,
4-[5-(2S,4-Dihydroxybutyl)pyrazin-2-yl]butane-1,3S-diol,
4-[5-(3R-Fluoro-2S,4-dihydroxybutyl)pyrazin-2-yl]-2R,4R-difluorobutane-1,3S-diol,
4-[5-(3S-Fluoro-2S,4-dihydroxybutyl)pyrazin-2-yl]-2S,4S-difluorobutane-1,3S-diol,
4-[5-(3R-Amino-2S,4-dihydroxybutyl)pyrazin-2-yl]-2R,4R-diaminobutane-1,3S-diol,
4-[5-(3S-Amino-2S,4-dihydroxybutyl)pyrazin-2-yl]-2S,4S-diaminobutane-1,3S-diol,
4-[5-(3R-(N-Methyl)amino-2S,4-dihydroxybutyl)pyrazin-2-yl]-2R,4R-di[(N-methyl)amino]butane-1,3S-diol,
4-[5-(3S-(N-Methyl)amino-2S,4-dihydroxybutyl)pyrazin-2-yl]-2S,4S-di[(N-methyl)amino]butane-1,3S-diol,
4-[5-(3R-(N-Ethyl)amino-2S,4-dihydroxybutyl)pyrazin-2-yl]-2R,4R-di[(N-ethyl)amino]butane-1,3S-diol,
4-[5-(3S-(N-Ethyl)amino-2S,4-dihydroxybutyl)pyrazin-2-yl]-2S,4S-di[(N-ethyl)amino]butane-1,3S-diol,
4-[5-(3R-(N-n-Butyl)amino-2S,4-dihydroxybutyl)pyrazin-2-yl]-2R,4R-di[(N-n-butyl)amino]butane-1,3S-diol,
4-[5-(3S-(N-n-Butyl)amino-2S,4-dihydroxybutyl)pyrazin-2-yl]-2S,4S-di[(N-n-butyl)amino]butane-1,3S-diol,
4-[5-(3R-(N-Benzyl)amino-2S,4-dihydroxybutyl)pyrazin-2-yl]-2R,4R-di[(N-benzyl)amino]butane-1,3S-diol,
4-[5-(3S-(N-Benzyl)amino-2S,4-dihydroxybutyl)pyrazin-2-yl]-2S,4S-di[(N-benzyl)amino]butane-1,3S-diol,
4-[5-(3R-(N-Acetyl)amino-2S,4-dihydroxybutyl)pyrazin-2-yl]-2R,4R-di[(N-acetyl)amino]butane-1,3S-diol,
4-[5-(3S-(N-Acetyl)amino-2S,4-dihydroxybutyl)pyrazin-2-yl]-2S,4S-di[(N-acetyl)amino]butane-1,3S-diol,
4-[5-(3R-(N-Butanoyl)amino-2S,4-dihydroxybutyl)pyrazin-2-yl]-2R,4R-di[(N-butanoyl)amino]butane-1,3S-diol,
4-[5-(3S-(N-Butanoyl)amino-2S,4-dihydroxybutyl)pyrazin-2-yl]-2S,4S-di[(N-butanoyl)amino]butane-1,3S-diol,
4-[5-(3R-(N-Benzoyl)amino-2S,4-dihydroxybutyl)pyrazin-2-yl]-2R,4R-di[(N-benzoyl)amino]butane-1,3S-diol,
4-[5-(3S-(N-Benzoyl)amino-2S,4-dihydroxybutyl)pyrazin-2-yl]-2S,4S-di[(N-benzoyl)amino]butane-1,3S-diol,
4-[5-(3R-Methoxy-2S,4-dihydroxybutyl)pyrazin-2-yl]-2R,4R-dimethoxybutane-1,3S-diol,
4-[5-(3S-Methoxy-2S,4-dihydroxybutyl)pyrazin-2-yl]-2S,4S-dimethoxybutane-1,3S-diol,
4-[5-(3R-Ethoxy-2S,4-dihydroxybutyl)pyrazin-2-yl]-2R,4R-diethoxybutane-1,3S-diol,
4-[5-(3S-Ethoxy-2S,4-dihydroxybutyl)pyrazin-2-yl]-2S,4S-diethoxybutane-1,3S-diol,
4-[5-(3R-n-Butoxy-2S,4-dihydroxybutyl)pyrazin-2-yl]-2R,4R-di-n-butoxybutane-1,3S-diol,
4-[5-(3S-n-Butoxy-2S,4-dihydroxybutyl)pyrazin-2-yl]-2S,4S-di-n-butoxybutane-1,3S-diol,
4-[5-(3R-(2-Hydroxyethyl)oxy-2S,4-dihydroxybutyl)pyrazin-2-yl]-2R,4R-di[(2-hydroxyethyl)oxy]butane-1,3S-diol,
4-[5-(3S-(2-Hydroxyethyl)oxy-2S,4-dihydroxybutyl)pyrazin-2-yl]-2S,4S-di[(2-hydroxyethyl)oxy]butane-1,3S-diol,
4-[5-(3R-(3-Hydroxy-n-propyl)oxy-2S,4-dihydroxybutyl)pyrazin-2-yl]-2R,4R-di[(3-hydroxy-n-propyl)oxy]butane-1,3S-diol,
4-[5-(3S-(3-Hydroxy-n-propyl)oxy-2S,4-dihydroxybutyl)pyrazin-2-yl]-2S,4S-di[(3-hydroxy-n-propyl)oxy]butane-1,3S-diol,
4-[5-(3R-(Carboxymethyl)oxy-2S,4-dihydroxybutyl)pyrazin-2-yl]-2R,4R-di[(carboxymethyl)oxy]butane-1,3S-diol,
4-[5-(3S-(Carboxymethyl)oxy-2S,4-dihydroxybutyl)pyrazin-2-yl]-2S,4S-di[(carboxymethyl)oxy]butane-1,3S-diol,
4-[5-(3R-(3-Carboxy-n-propyl)oxy-2S,4-dihydroxybutyl)pyrazin-2-yl]-2R,4R-di[(3-carboxy-n-propyl)oxy]butane-1,3S-diol, 4-[5-(3S-(3-Carboxy-n-propyl)oxy-2S,4-dihydroxybutyl)pyrazin-2-yl]-2S,4S-di[[(3-carboxy-n-propyl)oxy]butane-1,3S-diol, 1-[5-(3S,4-Dihydroxy-1E-butenyl)pyrazin-2-yl]butane-1R,2S,3R,4-tetraol, 4-Fluoro-1-[5-(2S,3R,4-trihydroxybutyl)pyrazin-2-yl]butane-1R,2S,3S-triol, 1-[5-(4-Fluoro-2S,3S-dihydroxybutyl)pyrazin-2-yl]butane-1R,2S,3R,4-tetraol and their salts with a pharmaceutically acceptable inorganic or organic acid.

4. A pharmaceutical composition according to claim 1 in which, either (A) $R_9$ and $R_{10}$ each is a —$CH_2OH$ radical, and either a) $R_3$ is a methylene radical, $R_4$ is a —CHOH— radical and one of the $R_1$, $R_2$, $R_5$ and $R_6$ radicals is a —CHF— or —CH(OR$_8$) radical and each of the others is a —CHOH— radical, or b) $R_2$ and $R_5$ each is a —CHOH— radical, $R_3$ is a methylene radical and $R_1$, $R_4$ and $R_6$ are identical and each is a —CH(OR$_8$) radical, or c) $R_1$ and $R_6$ each is a —CHOH— radical, $R_3$ is a methylene radical and $R_2$, $R_4$ and $R_5$ are identical and each is a —CH(OR$_8$) radical, or d) $R_1$, $R_4$, $R_5$ and $R_6$ each is a —CHOH— radical and —$R_2$—$R_3$— is a —CH=CH— radical, or (B) $R_1$, $R_2$, $R_4$, $R_5$ and $R_6$ each is a —CHOH— radical, $R_3$ is a methylene radical, $R_9$ is a —$CH_2OH$ radical, $R_{10}$ is a —$CH_2F$ radical, and $R_8$ is an alkyl radical.

5. A pharmaceutical composition comprising, as an active ingredient, at least one compound according to claim 1 selected from the group consisting of:

1-[5-(3S,4-Dihydroxybutyl)pyrazin-2-yl]butane-1R,2S,3R,4-tetraol,

1-[5-(3S,4-Dihydroxy-1E-butenyl)pyrazin-2-yl]butane-1R,2S,3R,4-tetraol,

1-[5-(2S-Methoxy-3R,4-dihydroxybutyl)pyrazin-2-yl]butane-1R,2S,3R,4-tetraol,

1-[5-(2R-Fluoro-3R,4-dihydroxybutyl)pyrazin-2-yl]butane-1R,2S,3R,4-tetraol,

1-[5-(2S,4-Dihydroxy-3R-methoxybutyl)pyrazin-2-yl]butane-1R,2S,3R,4-tetraol,

4-[5-(3R,4-Dihydroxy-2S-methoxybutyl)]pyrazin-2-yl]-3R,4R-dimethoxybutane-1,2-diol, 4-Fluoro-1-[5-(2S,3R,4-trihydroxybutyl)pyrazin-2-yl]butane-1R,2S,3R-triol, and their salts with a pharmaceutically acceptable inorganic or organic acid.

6. A compound of formula:

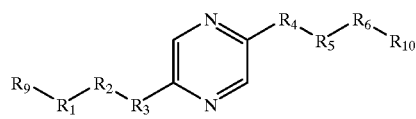

(I)

in which either (A) $R_9$ and $R_{10}$ each is a —$CH_2OH$ radical, and either a) $R_3$ is a methylene radical, $R_4$ is a —CHOH— radical and one of the $R_1$, $R_2$, $R_5$ and $R_6$ radicals is a carbonyl, methylene, —CHF—, —CH(NHR$_7$)— or —CH(OR$_8$) radical and each of the others is a —CHOH— radical, or b) $R_2$ and $R_5$ each is a —CHOH— radical, $R_3$ is a methylene radical and $R_1$, $R_4$ and $R_6$ are identical and each is a carbonyl, methylene, —CHF—, —CH(NHR$_7$)— or —CH(OR$_8$) radical, or c) $R_1$ and $R_6$ each is a —CHOH— radical, $R_3$ is a methylene radical and $R_2$, $R_4$ and $R_5$ are identical and each is a carbonyl, methylene, —CHF—, —CH(NHR$_7$)— or —CH(OR$_8$) radical, or d) $R_1$, $R_4$, $R_5$ and $R_6$ each is a —CHOH— radical and —$R_2$—$R_3$— is a —CH=CH— radical, or (B) $R_1$, $R_2$, $R_4$, $R_5$ and $R_6$ each is a —CHOH— radical, $R_3$ is a methylene radical, $R_9$ is a —$CH_2F$ or —$CH_2OH$ radical, $R_{10}$ is a —$CH_2F$ or —$CH_2OH$ radical, $R_9$ and $R_{10}$ not both being a —$CH_2OH$ radical, $R_7$ is a hydrogen atom or an alkyl, —CO—alk, —CO—Ar or —CO—Het radical, $R_8$ is an alkyl, —alk—COOH or —alk—OH radical, alk is an alkyl radical, Ar is a phenyl radical or a phenyl radical substituted by one or more substituents selected from a halogen atom and the alkyl, alkoxy, alkoxycarbonyl, amino, monoalkylamino and dialkylamino radicals, Het is a saturated or unsaturated, mono-, di- or tricyclic heterocycle comprising 1 to 9 carbon atoms and one or more heteroatoms selected from oxygen, sulphur and nitrogen, the alkyl and alkoxy radicals comprising 1 to 6 carbon atoms in a straight or branched chain, or one of its stereoisomers or, for a compound in which —$R_2$—$R_3$— represents a —CH=CH— radical, its cis or trans forms, or one of its salts with an organic or inorganic acid, provided, however, that said compound is not the compound of formula:

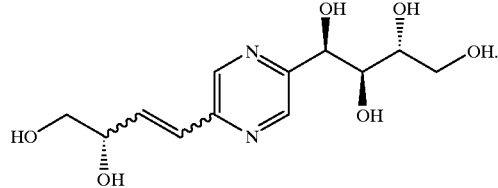

7. A process for the preparation of a compound according to claim 6 in which $R_9$ and $R_{10}$ each is a —$CH_2OH$ radical and either $R_3$ is a methylene radical, $R_4$ is a —CHOH— radical and one of the $R_1$, $R_2$, $R_5$ and $R_6$ radicals is a carbonyl radical and each of the others is a —CHOH— radical or $R_1$ and $R_6$ each is a —CHOH— radical, $R_3$ is a methylene radical and $R_2$, $R_4$ and $R_5$ are identical and each is a carbonyl radical or $R_2$ and $R_5$ each is a —CHOH— radical, $R_3$ is a methylene radical and $R_1$, $R_4$ and $R_6$ are identical and each is a carbonyl radical, in which process a compound selected from compounds of the formulae:

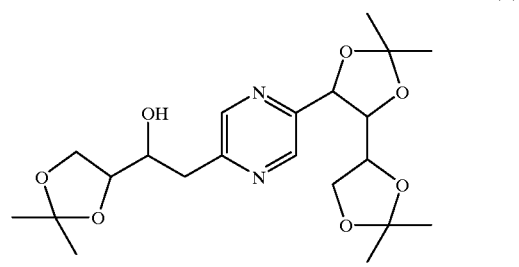

(II)

(III)
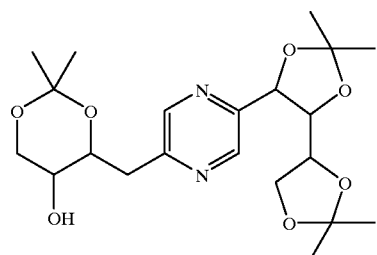

(IV)
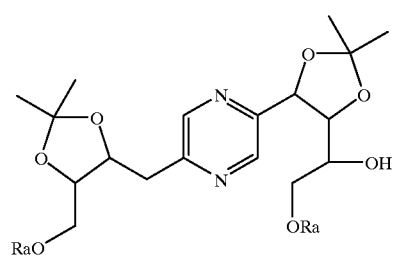

(V)
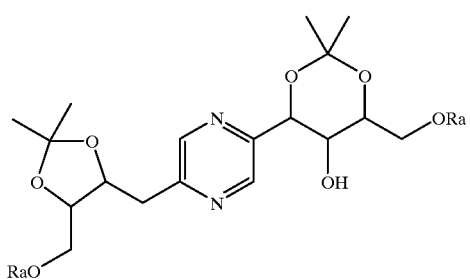

(VI)
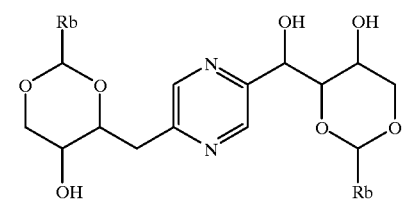

(VII)
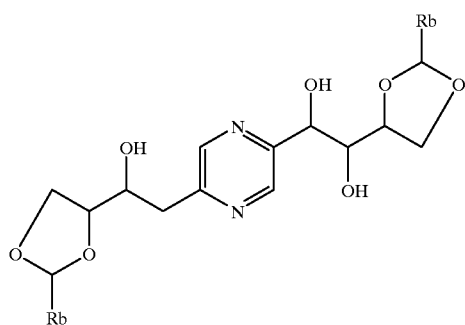

(VIII)
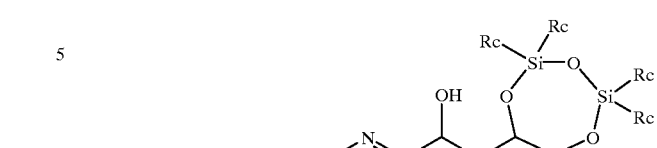

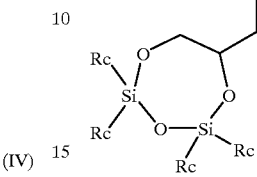

(IX)
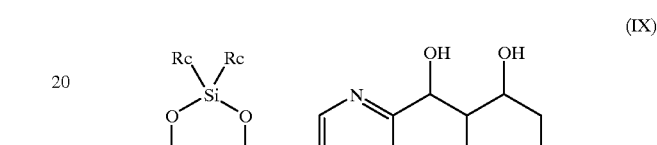

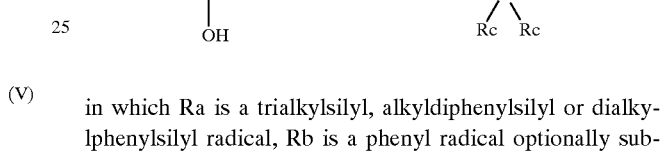

in which Ra is a trialkylsilyl, alkyldiphenylsilyl or dialkylphenylsilyl radical, Rb is a phenyl radical optionally substituted with least one alkoxy radical and Rc is an alkyl or phenyl radical, the alkyl and alkoxy radicals comprising 1 to 6 carbon atoms in a straight or branched chain, or a stereoisomer of such a derivative, is oxidized, the hydroxyls are then deprotected and the product is isolated and optionally converted to a salt.

8. A process for the preparation of a compound according to claim 6 in which (i) $R_9$ and $R_{10}$ each is a —CH$_2$OH radical and $R_3$ is a methylene radical, $R_4$ is a —CHOH— radical and one of the $R_1$, $R_2$, $R_5$ and $R_6$ radicals is a methylene radical and each of the others is a —CHOH— radical or (ii) $R_1$ and $R_6$ each is a —CHOH— radical, $R_3$ is a methylene radical and $R_2$, $R_4$ and $R_5$ are identical and each is a methylene radical or (iii) $R_2$ and $R_5$ each is a —CHOH— radical and $R_1$, $R_3$, $R_4$ and $R_6$ each is a methylene radical, in which process an alkyl or phenyl chlorothionocarbonate is condensed with a compound selected from compounds of the following formulae:

(II)
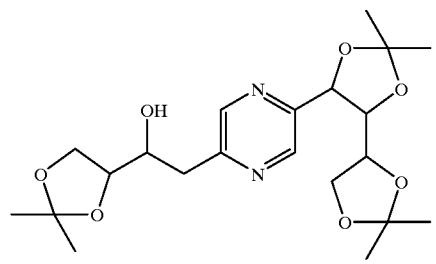

(III) 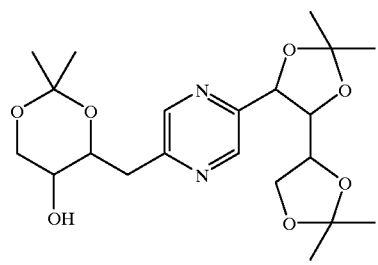

(IV) 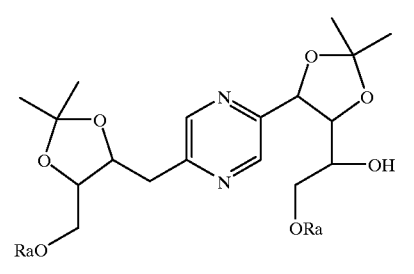

(V) 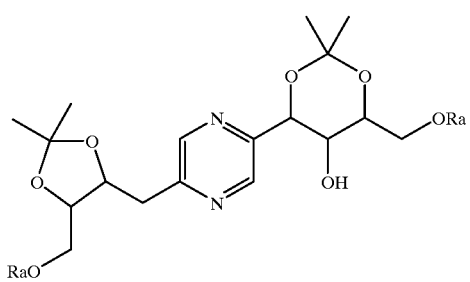

(VI) 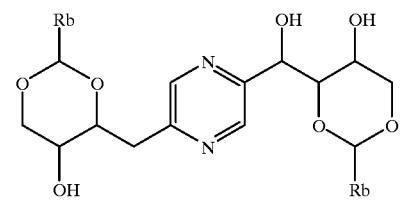

(VII) 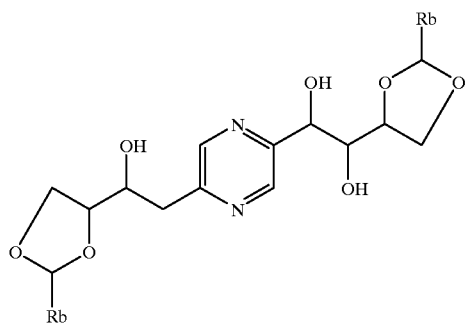

(VIII) 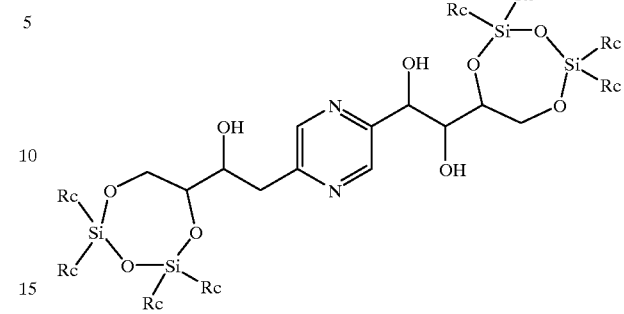

(IX) 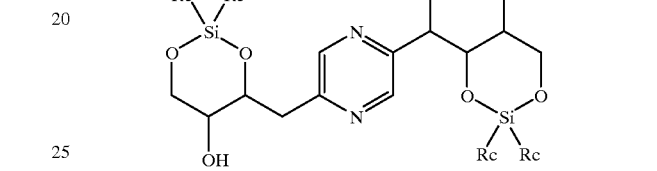

in which Ra is a trialkylsilyl, alkyldiphenylsilyl or dialkylphenylsilyl radical, Rb is a phenyl radical optionally substituted by at least one alkoxy radical and Rc is an alkyl or phenyl radical, the alkyl and alkoxy radicals comprising 1 to 6 carbon atoms in a straight or branched chain, or a stereoisomer of such a compound, the hydroxyls are then deprotected and the product is isolated and optionally converted to a salt.

9. A process for the preparation of a compound obtained product is reduced and the according to claim 6 in which either (A) $R_9$ and $R_{10}$ each is a —$CH_2OH$ radical and either $R_3$ is a methylene radical, $R_4$ is a —CHOH— radical and one of the $R_1$, $R_2$, $R_5$ and $R_6$ radicals is a —CHF— radical and each of the others is a —CHOH— radical or $R_1$ and $R_6$ each is a —CHOH— radical, $R_3$ is a methylene radical and $R_2$, $R_4$ and $R_5$ are identical and each is a —CHF— radical or $R_2$ and $R_5$ each is a —CHOH— radical, $R_3$ is a methylene radical and $R_1$, $R_4$ and $R_6$ are identical and each is a —CHF— radical or (B) $R_1$, $R_2$, $R_4$, $R_5$ and $R_6$ each is a —CHOH— radical, $R_3$ is a methylene radical, $R_9$ is a —$CH_2F$ or —$CH_2OH$ radical, $R_{10}$ is a —$CH_2F$ or —$CH_2OH$ radical, $R_9$ and $R_{10}$ not both being a —$CH_2OH$ radical, in which process a compound selected from compounds of the formulae:

(II) 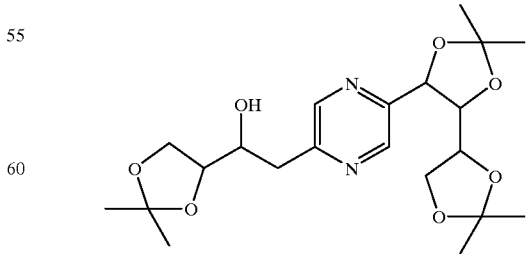

(III) 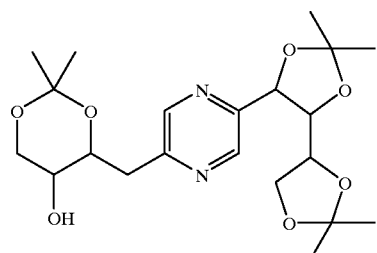

(IV) 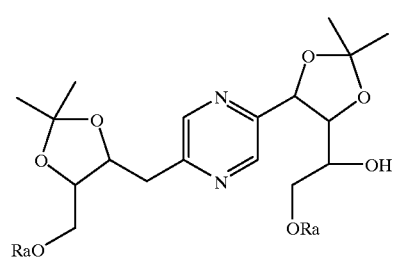

(V) 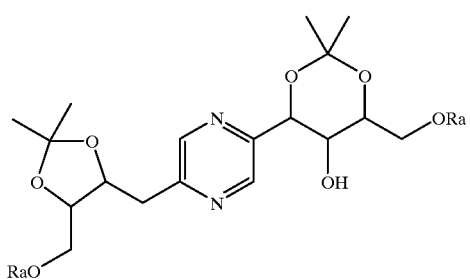

(VI) 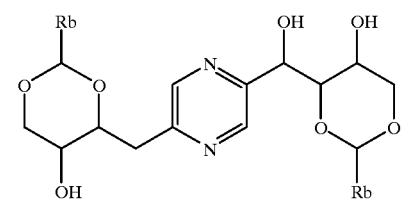

(VII) 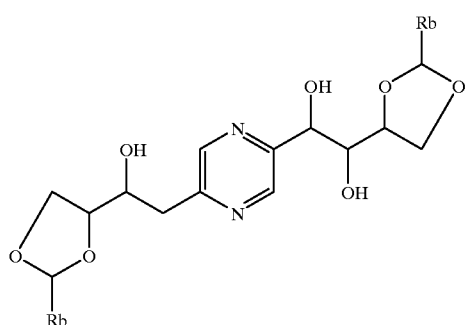

(VIII) 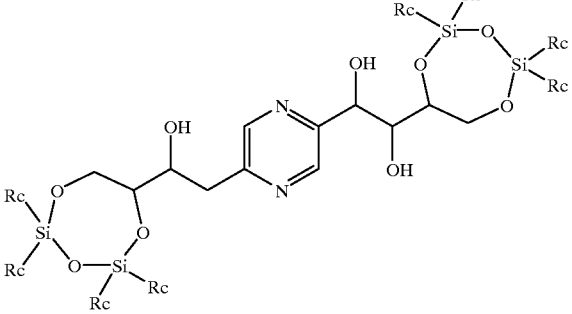

(IX) 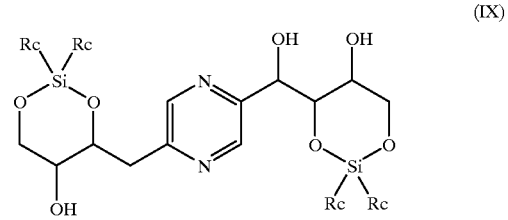

in which Ra is a trialkylsilyl, alkyldiphenylsilyl or dialkylphenylsilyl radical, Rb is a phenyl radical optionally substituted with at least one alkoxy radical and Rc is an alkyl or phenyl radical, the alkyl and alkoxy radicals comprising 1 to 6 carbon atoms in a straight or branched chain, or a stereoisomer of such a derivative is fluorinated, the hydroxyls are then deprotected and the product is isolated and optionally converted to a salt.

10. A process for the preparation of a compound according to claim 6 in which $R_9$ and $R_{10}$ each is a —$CH_2OH$ radical and either $R_3$ is a methylene radical, $R_4$ is a —CHOH— radical and one of the $R_1$, $R_2$, $R_5$ and $R_6$ radicals is a —CH(NHR$_7$)— radical and each of the others is a —CHOH— radical or $R_1$ and $R_6$ each is a —CHOH— radical, $R_3$ is a methylene radical and $R_2$, $R_4$ and $R_5$ are identical and each is a —CH(NHR$_7$)— radical or $R_2$ and $R_5$ each is a —CHOH— radical, $R_3$ is a methylene radical and $R_1$, $R_4$ and $R_6$ are identical and each is a —CH(NHR$_7$)— radical, said process comprising reducing a compound selected from compounds of the formulae:

(IIa) 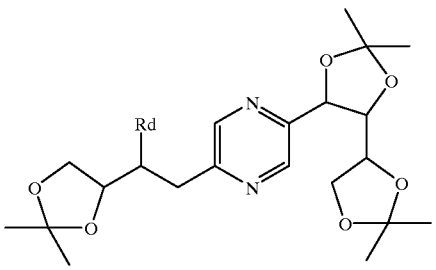

(IIIa)
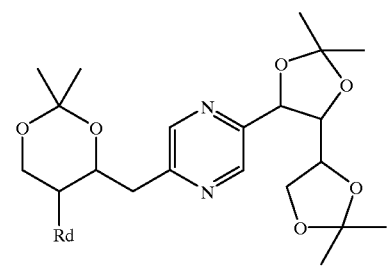

(IVa)
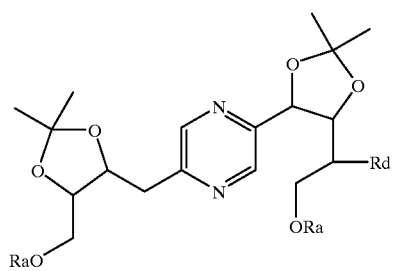

(Va)
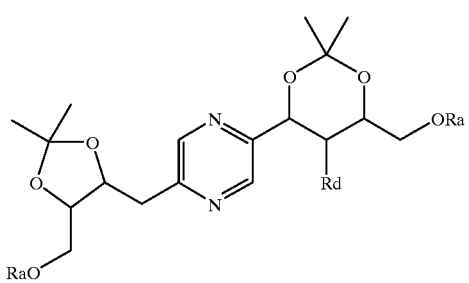

(VIa)
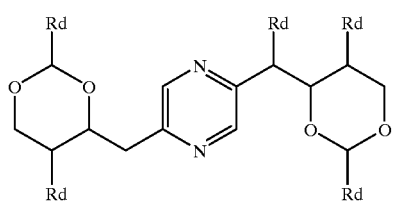

(VIIa)
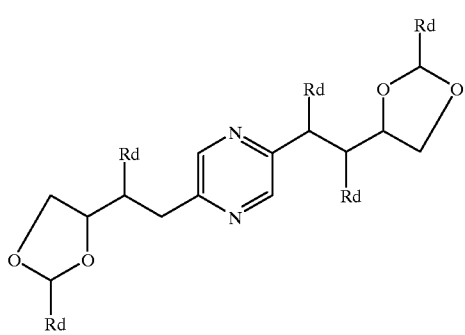

(VIIIa)
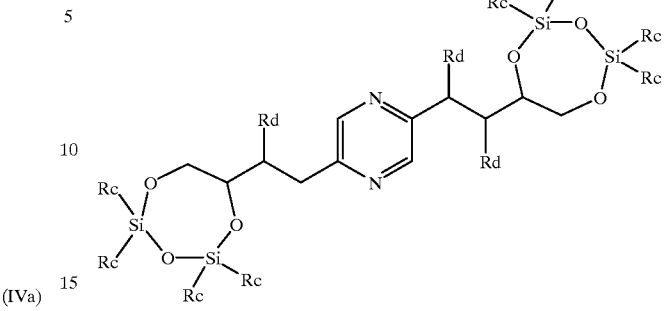

(IXa)

in which Ra is a trialkylsilyl, alkyldiphenylsilyl or dialkylphenylsilyl radical, Rb is a phenyl radical optionally substituted with at least one alkoxy radical, Rc is an alkyl or phenyl radical and Rd is an azido radical, the alkyl and alkoxy radicals comprising 1 to 6 carbon atoms in a straight or branched chain, or a stereoisomer of such a compound, optionally followed by reacting the product with a compound of formula HalR$_7$, in which R$_7$ has the same meanings as in claim 6, except that R$_7$ is not hydrogen, and Hal is a halogen atom, deprotecting the hydroxyls and isolating the product and optionally converting it to a salt.

11. A process for the preparation of a compound according to claim 6 in which R$_9$ and R$_{11}$ each is a —CH$_2$OH radical and either R$_3$ is a methylene radical, R$_4$ is a —CHOH— radical and one of the R$_1$, R$_2$, R$_5$ and R$_6$ radicals is a —CH(OR$_8$) radical and each of the others is a —CHOH— radical or R$_1$ and R$_6$ each is a —CHOH— radical, R$_3$ is a methylene radical and R$_2$, R$_4$ and R$_5$ are identical and each is a —CH(OR$_8$) radical or R$_2$ and R$_5$ each is a —CHOH— radical, R$_3$ is a methylene radical and R$_1$, R$_4$ and R$_6$ are identical and each is a —CH(OR$_8$) radical, said process comprising reacting a compound of formula:

(II)
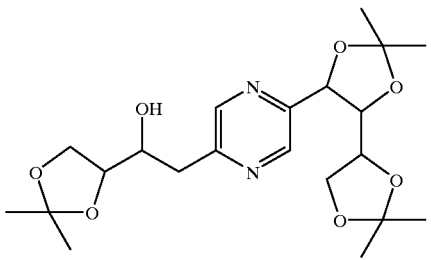

-continued (III) 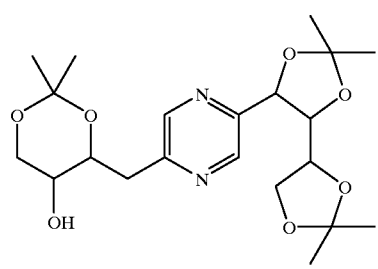

(IV) 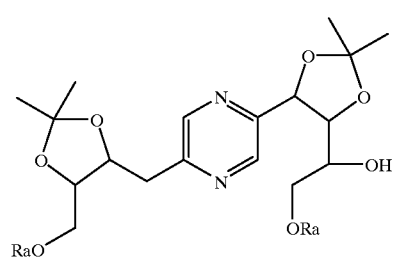

(V) 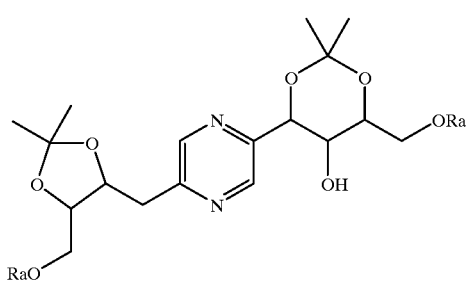

(VI) 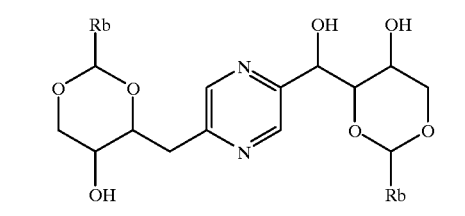

(VII) 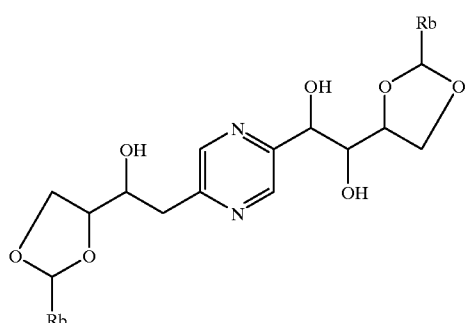

-continued (VIII) 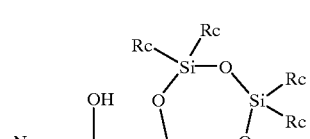

(IX) 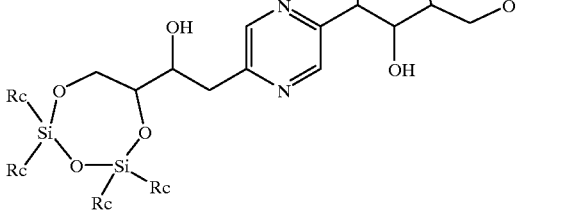

in which Ra is a trialkylsilyl, alkyldiphenylsilyl or dialkylphenylsilyl radical, Rb is a phenyl radical optionally substituted with at least one alkoxy radical and Rc is an alkyl or phenyl radical, the alkyl and alkoxy radicals comprising 1 to 6 carbon atoms in a straight or branched chain, or a stereoisomer of such a derivative, with a compound of formula $HalR_8$, in which $R_8$ has the same meanings as in claim 6, and Hal is a halogen, then deprotecting the hydroxyls and isolating the product and optionally converting it to a salt.

12. A process for the preparation of a compound according to claim 6 in which $R_9$ and $R_{10}$ each is a —$CH_2OH$ radical and $R_1$, $R_4$, $R_5$ and $R_6$ each is a —CHOH— radical and —$R_2$—$R_3$— is a —CH=CH— radical, in which process a compound of formula:

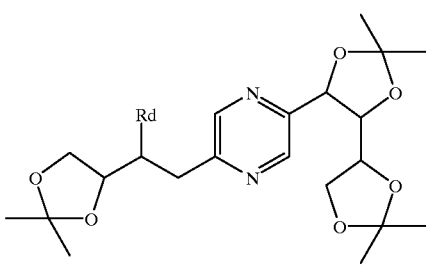

in which Rd is an —$OSO_2$—Re radical and Re is a methyl, trifluoromethyl or 4-methylphenyl radical, or a stereoisomer of such a derivative, is dehydrated, the hydroxyls are then deprotected and the product is isolated and optionally converted to a salt.

13. A method for the treatment or prevention of diabetes, or complications thereof, this method comprising administering to a patient in need of such treatment an effective amount of a compound of general formula:

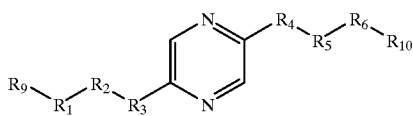

(I)

in which either (A) $R_9$ and $R_{10}$ are identical and each is a —$CH_2OH$ radical and either a) $R_3$ is a methylene radical, $R_4$ is a —CHOH— radical and one of the $R_1$, $R_2$, $R_5$ and $R_6$ radicals is a carbonyl, methylene, —CHF—, —CH($NHR_7$)— or —CH($OR_8$) radical and each of the others each is a —CHOH— radical, or b) $R_2$ and $R_5$ each is a —CHOH— radical, $R_3$ is a methylene radical and $R_1$, $R_4$ and $R_6$ are identical and each is a carbonyl, methylene, —CHF—, —CH($NHR_7$)— or —CHOR($OR_8$) radical, or c) $R_1$ and $R_6$ each is a —CHOH— radical, $R_3$ is a methylene radical and $R_2$, $R_4$ and $R_5$ are identical and each is a carbonyl, methylene, —CHF—, —CH($NHR_7$)— or —CH($OR_8$) radical, or d) $R_1$, $R_4$, $R_5$ and $R_6$ each is a —CHOH— radical and —$R_2$—$R_3$— is a —CH=CH— radical, or (B) $R_1$, $R_2$, $R_4$, $R_5$ and $R_6$ each is a —CHOH— radical, $R_3$ is a methylene radical, $R_9$ is a —$CH_2F$ or —$CH_2OH$ radical and $R_{10}$ is a —$CH_2F$ or —$CH_2OH$ radical, $R_9$ and $R_{10}$ not both being a —$CH_2OH$ radical, $R_7$ is a hydrogen atom or an alkyl, —CO—alk, —CO—Ar or —CO—Het radical, $R_8$ is an alkyl, —alk—COOH or —alk—OH radical, alk is an alkyl radical, Ar is a phenyl radical or a phenyl radical substituted with one or more substituents selected from a halogen atom and the alkyl, alkoxy, alkoxycarbonyl, amino, monoalkylamino and dialkylamino radicals, Het is a saturated or unsaturated, mono-, di- or tricyclic heterocycle comprising 1 to 9 carbon atoms and one or more heteroatoms selected from oxygen, sulphur and nitrogen, the alkyl and alkoxy radicals comprising 1 to 6 carbon atoms in a straight or branched chain, or one of its stereoisomers or, for a compound in which —$R_2$—$R_3$— represents a —CH=CH— radical, its cis or trans forms, or its salt with a pharmaceutically acceptable inorganic or organic acid in a pharmaceutically acceptable vehicle.

* * * * *